(12) United States Patent
Berger et al.

(10) Patent No.: US 7,335,775 B2
(45) Date of Patent: Feb. 26, 2008

(54) EFFECTOR CONJUGATES, PROCESS FOR THEIR PRODUCTION AND THEIR PHARMACEUTICAL USE

(75) Inventors: Markus Berger, Berlin (DE); Gerhard Siemeister, Berlin (DE); Ulrich Klar, Berlin (DE); Jorg Willuda, Berlin (DE); Andreas Menrad, Oranienburg (DE); Klaus Bosslet, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 11/509,557

(22) Filed: Aug. 25, 2006

(65) Prior Publication Data

US 2007/0088060 A1    Apr. 19, 2007

Related U.S. Application Data

(62) Division of application No. 10/631,011, filed on Jul. 31, 2003, now Pat. No. 7,129,254.

(60) Provisional application No. 60/451,673, filed on Mar. 5, 2003.

(30) Foreign Application Priority Data

Jul. 31, 2002 (DE) ............... 102 34 975
Feb. 7, 2003 (DE) ............... 103 05 098

(51) Int. Cl.
  *C07D 277/20* (2006.01)
  *C07D 417/08* (2006.01)
(52) U.S. Cl. .............. 546/268.1; 548/146; 548/206; 548/215; 549/357
(58) Field of Classification Search ......... 546/268.1; 548/146, 206, 215; 549/357
See application file for complete search history.

(56) References Cited

U.S. PATENT DOCUMENTS

| 4,552,893 A | 11/1985 | Gleason et al. |
| 5,942,555 A | 8/1999 | Swanson et al. |
| 6,075,120 A | 6/2000 | Cheronis et al. |
| 6,410,301 B1 | 6/2002 | Julien et al. |
| 6,441,213 B1 | 8/2002 | Musa et al. |
| 6,864,330 B2 | 3/2005 | Schneider et al. |
| 2002/0045609 A1 | 4/2002 | Ashley et al. |
| 2002/0058286 A1 | 5/2002 | Danishefsky et al. |
| 2002/0058817 A1 | 5/2002 | Danishefsky et al. |
| 2004/0242854 A1 | 12/2004 | Osborn et al. |

FOREIGN PATENT DOCUMENTS

| EP | 0121350 | 10/1984 |
| EP | 1156053 | 11/2001 |
| WO | WO 94/11021 | 5/1994 |
| WO | WO 01/64650 | 9/2001 |
| WO | WO 01/83800 | 11/2001 |
| WO | WO 01/92255 | 12/2001 |
| WO | WO 03/005026 | 1/2003 |

OTHER PUBLICATIONS

Bersuker I B et al: "Improved Electron-Conformational Method of Pharmacophore Identification and Bioactivity Prediction. Application to Angiotensin Converting Enzyme Inhibitors" Journal of Chemical Information and Computer Sciences. Nov.-Dec. 2000, vol. 40, No. 6, Nov. 2000 pp. 1363-1376.

Wang Lai-Xi et al: "Carbohydrate-Centered Maleimide Cluster as a New Type of Templates for Multivalent Peptide Assembling: Synthesis of Multivalent HIV-1 gp41 Peptides." Bioorganic and Medicinal Chemistry, vol. 11, No. 1, Jan. 2, 2003, pp. 159-166.

Reghunadhan Nair C P et al.: "Free Readical Copolymerisation of N-(4-Hydroxy Phenyl) Maleimide With Vinyl Monomers: Solvent and Penultimate-Unit Effects" European Polymer Journal, Pergamon Press Ltd. Oxford, GB., vol. 35, No. 10, Jul. 28, 1999, pp. 1829-1840.

Kalgutkar A S et al.: "Inactivation of Prostaglandin Endoperoxide Snythase (PGHS) by N-(Substituted) Maleimides" Advances in Experimental Medicine and Biology. 1997, vol. 407, 1997, pp. 79-85.

*Primary Examiner*—Taofiq Solola
(74) *Attorney, Agent, or Firm*—Millen, White, Zelano & Branigan, P.C.

(57) ABSTRACT

Conjugates of epothilones and epothilone derivatives (as effectors) with suitable biomolecules (as recognition units) are described. Their production is carried out by the effectors being reacted with suitable linkers, and the compounds that are produced are conjugated to the recognition units. The pharmaceutical use of the conjugates for treating proliferative or angiogenesis-associated processes is described.

7 Claims, No Drawings

SEQUENCE LISTING

```
<160> NUMBER OF SEQ ID NOS: 1

<210> SEQ ID NO 1
<211> LENGTH: 241
<212> TYPE: PRT
<213> ORGANISM: Homo sapiens
<220> FEATURE:
<223> OTHER INFORMATION: anti-(ED-B) scFV Antibody fragment; Name: AP39

<400> SEQUENCE: 1

Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Phe Ser Met Ser Trp Val Arg Gln Ala Pro Gly Lys Gly Leu
                35                  40                  45

Glu Trp Val Ser Ser Ile Ser Gly Ser Ser Gly Thr Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Lys Pro Phe Pro Tyr Phe Asp Tyr
                95                  100                 105

Trp Gly Gln Gly Thr Leu Val Thr Val Ser Ser Gly Asp Gly Ser
                110                 115                 120

Ser Gly Gly Ser Gly Gly Ala Ser Glu Ile Val Leu Thr Gln Ser
                125                 130                 135

Pro Gly Thr Leu Ser Leu Ser Pro Gly Glu Arg Ala Thr Leu Ser
                140                 145                 150

Cys Arg Ala Ser Gln Ser Val Ser Ser Ser Phe Leu Ala Trp Tyr
                155                 160                 165

Gln Gln Lys Pro Gly Gln Ala Pro Arg Leu Leu Ile Tyr Tyr Ala
                170                 175                 180

Ser Ser Arg Ala Thr Gly Ile Pro Asp Arg Phe Ser Gly Ser Gly
                185                 190                 195

Ser Gly Thr Asp Phe Thr Leu Thr Ile Ser Arg Leu Glu Pro Glu
                200                 205                 210
```

```
Asp Phe Ala Val Tyr Tyr Cys Gln Gln Thr Gly Arg Ile Pro Pro
            215             220                     225

Thr Phe Gly Gln Gly Thr Lys Val Glu Ile Lys Gly Gly Gly Cys
            230             235                     240

Ala
```

EFFECTOR CONJUGATES, PROCESS FOR THEIR PRODUCTION AND THEIR PHARMACEUTICAL USE

This application is a divisional of U.S. patent application Ser. No. 10/631,011 filed on Jul. 31, 2003, which claims the benefit of U.S. patent application Ser. No. 60/451,673 filed on Mar. 5, 2003, both of which are fully incorporated by reference herein.

The development of the understanding relating to the recognition of binding regions, especially in the field of monoclonal antibodies or fragments thereof against specific tumor antigens, makes it possible to consider a selective tumor therapy by specific release of an anti-tumor active agent at the target site.

A precondition for such an approach, in which a highly active (toxic) active agent (effector) is coupled to a high-molecular, tumor-specific recognition unit, such as, for example, to an antibody, is a substantial inactivity of the conjugate, whose minimum components are represented by a recognition unit and an effector, until it has reached the target site (tumor). Arriving at the target site, the conjugate binds to the cell surface and the active ingredient, optionally after the preceding internalization of the entire complex, can be released.

The successful therapy of solid tumors, especially with monoclonal antibodies, can be limited, however, by an inadequate penetration of the antibody into the tumor as well as the heterogeneous dispersion of the corresponding tumor-associated antigens in the tumor tissue.

These limitations could be avoided in that the tumor-vascular system is attacked in a specific way. The growth of tumors below a volume of about 2 mm³ depends on a neoangiogenesis. The subsequent tumor growth is based on an intact vascular system, which ensures the supply with nutrients or the removal of waste products. The selective destruction of this system should therefore result in a necrosis of the tumor. The attack on the vascular system of the tumor promises a number of advantages relative to the direct attack on the tumor itself. In comparison to tumor cells, endothelial cells are easier to access, since no tumor tissue has to be penetrated. The damage of an individual tumor vessel should result in a necrosis of thousands of tumor cells. To damage a tumor vessel, it is not necessary to kill all endothelial cells. The specific attack of endothelial cells in or close to the tumors minimizes systemic side effects. Endothelial cells are genetically very stable, so that the probability of a development of resistance against the tumor therapeutic agent is low.

Within the scope of this invention, surprisingly enough, a possibility has now been found to link the chemically very sensitive, highly-functionalized class of active agents of epothilones and analogs thereof to a high-molecular recognition unit via different linkers in different positions of the active agent.

The object of this invention is thus, inter alia,
1. to find a method to link highly active agents from the structural class of the epothilones and epothilone derivatives with suitable linkers,
2. to synthesize suitable linkers,
3. to develop a method to link these epothilone-linker conjugates to recognition units, such as, for example, monoclonal antibodies or fragments thereof, to form immune conjugates that are both chemically and metabolically sufficiently stable for the development of a pharmaceutical, and that are superior to the epothilones or epothilone derivatives that are taken as a basis with respect to their therapeutic range, their selectivity of action and/or undesirable toxic side effects and/or the degree of their activity.

This invention accordingly comprises effector conjugates of general formula I

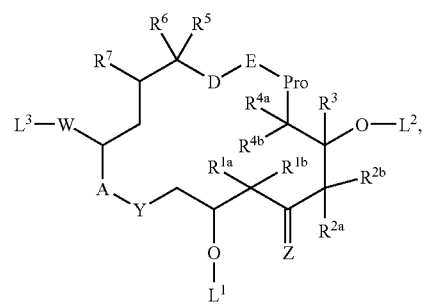

in which
$R^{1a}$, $R^{1b}$, independently of one another, are hydrogen, $C_1$-$C_{10}$ alkyl, aryl, aralkyl, or together a —$(CH_2)_m$— group, in which m is 2 to 5, $R^{2a}$, $R^{2b}$, independently of one another, are hydrogen, $C_1$-$C_{10}$ alkyl, aryl, aralkyl, or together a —$(CH_2)_n$— group, in which n is 2 to 5, or $C_2$-$C_{10}$ alkenyl, or $C_2$-$C_{10}$ alkynyl, $R^3$ is hydrogen, $C_1$-$C_{10}$ alkyl, aryl or aralkyl, and $R^{4a}$, $R^{4b}$, independently of one another, are hydrogen, $C_1$-$C_{10}$ alkyl, aryl, aralkyl, or together a —$(CH_2)_p$— group, in which p is 2 to 5, $R^5$ is hydrogen, $C_1$-$C_{10}$ alkyl, aryl, aralkyl, $CO_2H$, $CO_2$alkyl, $CH_2OH$, $CH_2OAlkyl$, $CH_2OAcyl$, CN, $CH_2NH_2$, $CH_2N(alkyl, acyl)_{1,2}$, or $CH_2Hal$, Hal is a halogen atom, $R^6$, $R^7$ in each case are hydrogen, or together an additional bond, or together an oxygen atom, or together an NH group, or together an N-alkyl group, or together a $CH_2$ group, and G is an oxygen atom or $CH_2$, D-E is a group $H_2C$—$CH_2$, HC=CH, C≡C, CH(OH)—CH(OH), CH(OH)—$CH_2$, $CH_2$—CH(OH),

O—$CH_2$, or, if G represents a $CH_2$ group, D-E is $CH_2$—O,

W is a group C(=X)$R^8$, or a bi- or tricyclic aromatic or heteroaromatic radical, $L^3$ is hydrogen, or, if a radical in W contains a hydroxyl group, forms a group O-$L^4$ with the latter, or, if a radical in W contains an amino group, forms a group N$R^{25}$-$L^4$ with the latter, $R^{25}$ is hydrogen or $C_1$-$C_{10}$ alkyl, X is an oxygen atom, or two $OR^{20}$ groups, or a $C_2$-$C_{10}$ alkylenedioxy group that may be straight-chain or branched, or H/O$R^9$, or a $CR^{10}R^{11}$ group, $R^8$ is hydrogen, $C_1$-$C_{10}$ alkyl, aryl, aralkyl, halogen or CN, and $R^9$ is hydrogen or a protective group $PG^X$, $R^{10}$, $R^{11}$ in each case independently of one another, are hydrogen, $C_1$-$C_{20}$ alkyl, aryl, aralkyl, or together with a methylene carbon atom form a 5- to 7-membered carbocyclic ring, Z can represent oxygen or H/O$R^{12}$, $R^{12}$ can represent hydrogen or a protective group $PG^Z$, A-Y can represent a group O—C(=O), O—CH$_2$, CH$_2$—C(=O), N$R^{21}$—C(=O) or N$R^{21}$—SO$_2$, $R^{20}$ can represent $C_1$-$C_{20}$ alkyl, $R^{21}$ can represent a hydrogen atom or $C_1$-$C_{10}$ alkyl, $PG^X$, $PG^Y$, and $PG^Z$ can represent a protective group PG, and $L^1$, $L^2$, and $L^4$, independently of one another, can represent hydrogen, a group C(=O) Cl, a group C(=S)Cl, a group $PG^Y$ or a linker of general formula (III) or (IV); provided that at least one substituent $L^1$, $L^2$ or $L^4$ represents a linker of general formula (III) or (IV);

the linker of general formula (III) has the following structure,

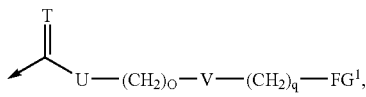
III in which

T can represent oxygen or sulfur,

U can represent oxygen, CH$R^{22}$, CH$R^{22}$—N$R^{23}$—C(=O)—, CH$R^{22}$—N$R^{23}$—C(=S)—, O—C(=O)—CH$R^{22}$—N$R^{23}$—C(=O)—, O—C(=O)—CH$R^{22}$—N$R^{23}$—C(=S)— or N$R^{24a}$, o can represent 0 to 15, V can represent a bond, aryl, a group

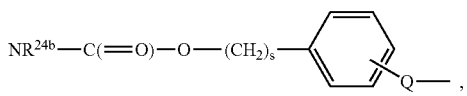

or a group

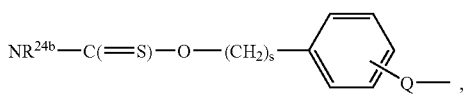

s can represent 0 to 4,

Q can represent a bond, O—C(=O)—N$R^{24c}$, O—C(=S)—N$R^{24c}$,

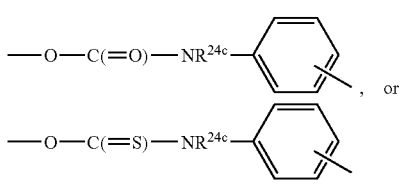, or $R^{22}$ can represent hydrogen, $C_1$-$C_{10}$ alkyl, aryl or aralkyl, $R^{23}$ can represent hydrogen or $C_1$-$C_{10}$ alkyl, $R^{24a}$, $R^{24b}$, and $R^{24c}$, independently of one another, can represent hydrogen or $C_1$-$C_{10}$ alkyl, q can represent 0 to 15, $FG^1$ can represent $C_1$-$C_{10}$ alkyl-$S_3$,

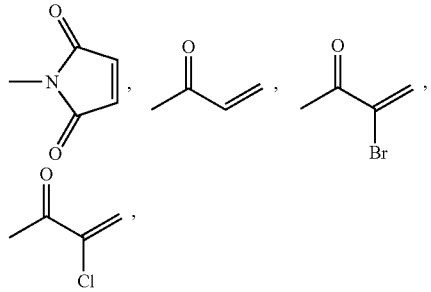

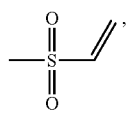

or CO$_2$H; and the linker of general formula (IV) has the following structure,

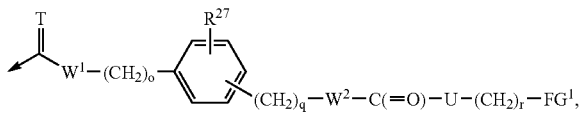
IV in which

T can represent oxygen or sulfur, $W^1$, $W^2$ are the same or different and can represent oxygen or N$R^{24a}$, o can represent 0 to 5, $R^{22}$ can represent hydrogen, $C_1$-$C_{10}$ alkyl, aryl or aralkyl, $R^{23}$ can represent hydrogen, or $C_1$-$C_{10}$ alkyl, $R^{24a}$ can represent hydrogen or $C_1$-$C_{10}$ alkyl, $R^{27}$ can represent halogen, CN, NO$_2$, CO$_2R^{28}$, or O$R^{28}$, $R^{28}$ can represent hydrogen, $C_1$-$C_{10}$ alkyl, aryl or aralkyl, q can represent 0 to 5, U can represent oxygen, CH$R^{22}$, CH$R^{22}$—N$R^{23}$—C(=O)—, CH$R^{22}$—N$R^{23}$—C(=S)— or $C_1$-$C_{20}$ alkyl, r can represent 0 to 20, $FG^1$ can represent $C_1$-$C_{10}$ alkyl-$S_3$,

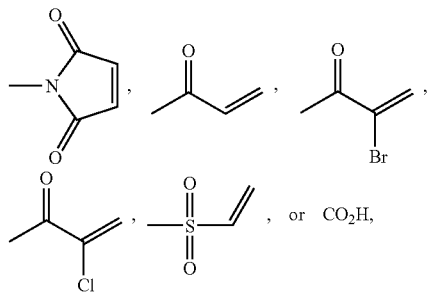, or CO$_2$H, as a single isomer or a mixture of different isomers and/or as a pharmaceutically acceptable salt thereof.

In addition, the invention describes the production of effector recognition unit conjugates of general formula (I), wherein the substituents therein have the above-mentioned meanings, but at least one group $FG^1$ replaced by a group $FG^{2a}$ or $FG^{2b}$, wherein $FG^{2a}$ or $FG^{2b}$ can have the following meanings:

$FG^{2a}$:

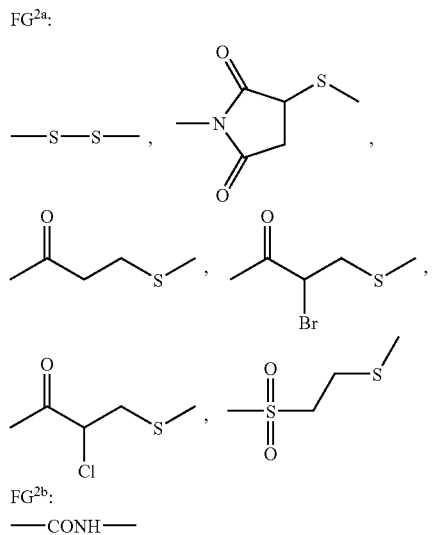

$FG^{2b}$:

—CONH— and wherein a recognition unit is conjugated via a sulfur atom with the group $FG^{2a}$, wherein the indicated sulfur atom is a component of the recognition unit, or via an amide function of group $FG^{2b}$, wherein the indicated nitrogen atom is a component of the recognition unit;

wherein the recognition unit can be, for example, a peptide, a soluble receptor, a cytokine, a lymphokine, an aptamer, a spiegelmer, a recombinant protein, a framework structure, a monoclonal antibody or a fragment of a monoclonal antibody.

According to this invention, the above-mentioned effector recognition unit conjugates can comprise one or more recognition units; in this case, the recognition units that belong to a conjugate can be identical or different. It is preferred that the recognition units of a conjugate be identical.

The effector recognition unit conjugates according to the invention can be used in the form of their α-, β- or γ-cyclodextrin-clathrates or in the form of liposomal or pegylated compositions.

The conjugates according to the invention are preferably used for the treatment of diseases that are associated with proliferative processes. For example, the therapy of different tumors, the therapy of inflammatory and/or neurodegenerative diseases, such as multiple sclerosis or Alzheimer's disease, the therapy of angiogenesis-associated diseases such as the growth of solid tumors, rheumatoid arthritis or diseases of the ocular fundus, can be mentioned.

The production of epothilones, their precursors and derivatives of general formula I is carried out according to the methods that are known to one skilled in the art, as they are described in, for example, DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. Nos. 6,204,388, 6,387,927, 6,380,394, U.S 02/52028, U.S 02/58286, U.S 02/62030, WO 02/32844, WO 02/30356, WO 02/32844, WO 02/14323, and WO 02/8440.

As alkyl groups $R^{1a}$, $R^{1b}$, $R^{2a}$, $R^{2b}$, $R^3$, $R^{4a}$, $R^{4b}$, $R^5$, $R^8$, $R^{10}$, $R^{11}$, $R^{20}$, $R^{21}$, $R^{22}$, $R^{23}$, $R^{24a}$, $R^{24b}$, $R^{24c}$, $R^{25}$ and $R^{26}$, straight-chain or branched-chain alkyl groups with 1-20 carbon atoms can be considered, such as, for example, methyl, ethyl, propyl, isopropyl, butyl, isobutyl, tert.-butyl, pentyl, isopentyl, neopentyl, heptyl, hexyl, and decyl.

Alkyl groups $R^{1a}$, $R^{1b}$, $R^{2a}$, $R^{2b}$, $R^3$, $R^{4a}$, $R^{4b}$, $R^5$, $R^8$, $R^{10}$, $R^{11}$, $R^{20}$, $R^{21}$, $R^{22}$, $R^{23}$, $R^{24a}$, $R^{24b}$, $R^{24c}$, $R^{25}$ and $R^{26}$ can also be perfluorinated or substituted by 1-5 halogen atoms, hydroxy groups, $C_1$-$C_4$-alkoxy groups or $C_6$-$C_{12}$-aryl groups (which can be substituted by 1-3 halogen atoms).

As aryl radicals $R^{1a}$, $R^{1b}$, $R^{2a}$, $R^{2b}$, $R^3$, $R^{4a}$, $R^{4b}$, $R^5$, $R^8$, $R^{10}$, $R^{11}$, $R^{22}$, $R^{26}$ and V, substituted and unsubstituted carbocyclic or heterocyclic radicals with one or more heteroatoms, such as phenyl, naphthyl, furyl, thienyl, pyridyl, pyrazolyl, pyrimidinyl, oxazolyl, pyridazinyl, pyrazinyl, quinolyl, thiazolyl, benzothiazolyl or benzoxazolyl, which can be substituted in one or more places by halogen, OH, O-alkyl, $CO_2H$, $CO_2$-alkyl, —$NH_2$, —$NO_2$, —$N_3$, —CN, $C_1$-$C_{20}$-alkyl, $C_1$-$C_{20}$-acyl or $C_1$-$C_{20}$-acyloxy groups, are suitable. The heteroatoms can be oxidized provided that this does not cause the aromatic character to be lost, such as, for example, the oxidation of a pyridyl to a pyridyl-N-oxide.

As bicyclic and tricyclic aryl radicals W, substituted and unsubstituted, carbocyclic or heterocyclic radicals with one or more heteroatoms such as naphthyl, anthryl, benzothiazolyl, benzoxazolyl, benzimidazolyl, quinolyl, isoquinolyl, benzoxazinyl, benzofuranyl, indolyl, indazolyl, quinoxalinyl, tetrahydroisoquinolinyl, tetrahydroquinolinyl, thienopyridinyl, pyridopyridinyl, benzopyrazolyl, benzotriazolyl, or dihydroindolyl, which can be substituted in one or more places by halogen, OH, O-alkyl, $CO_2H$, $CO_2$-alkyl, —$NH_2$, —$NO_2$, —$N_3$, —CN, $C_1$-$C_{20}$-alkyl, $C_1$-$C_{20}$-acyl or $C_1$-$C_{20}$-acyloxy groups, are suitable. The heteroatoms can be oxidized provided that this does not cause the aromatic character to be lost, such as, for example, the oxidation of a quinolyl to a quinolyl-N-oxide.

The aralkyl groups in $R^{1a}$, $R^{1b}$, $R^{2a}$, $R^{2b}$, $R^3$, $R^{4a}$, $R^{4b}$, $R^5$, $R^8$, $R^{10}$, $R^{11}$, $R^{22}$ and $R^{26}$ can contain in the ring up to 14 C atoms, preferably 6 to 10 C atoms, and in the alkyl chain 1 to 8 atoms, preferably 1 to 4 atoms. As an aralkyl radical, for example, benzyl, phenylethyl, naphthylmethyl, naphthylethyl, furylmethyl, thienylethyl or pyridylpropyl is suitable. The rings can be substituted in one or more places by halogen, OH, O-alkyl, $CO_2H$, $CO_2$-alkyl, —$NO_2$, —$N_3$, —CN, $C_1$-$C_{20}$-alkyl, $C_1$-$C_{20}$-acyl or $C_1$-$C_{20}$-acyloxy groups.

As representatives of protective groups PG, tris($C_1$-$C_{20}$ alkyl)silyl, bis($C_1$-$C_{20}$ alkyl)-arylsilyl, ($C_1$-$C_{20}$ alkyl)-diarylsilyl, tris(aralkyl)-silyl, $C_1$-$C_{20}$-alkyl, $C_2$-$C_{20}$-alkenyl, $C_4$-$C_7$-cycloalkyl, which in addition can contain an oxygen atom in the ring, aryl, $C_7$-$C_{20}$-aralkyl, $C_1$-$C_{20}$-acyl, aroyl, $C_1$-$C_{20}$-alkoxycarbonyl, $C_1$-$C_{20}$-alkylsulfonyl as well as arylsulfonyl can be cited.

As alkyl-, silyl- and acyl radicals for the protective groups PG, especially the radicals that are known to one skilled in the art are considered. Preferred are the alkyl or silyl radicals that can be easily cleaved from the corresponding alkyl and silyl ethers, such as, for example, the methoxymethyl, methoxyethyl, ethoxyethyl, tetrahydropyranyl, tetrahydrofuranyl, trimethylsilyl, triethylsilyl, tert.-butyldimethylsilyl, tert.-butyldiphenylsilyl, tribenzylsilyl, triisopropylsilyl, benzyl, para-nitrobenzyl, and para-methoxybenzyl radicals, as well as alkylsulfonyl and arylsulfonyl radicals. As an alkoxycarbonyl radical, e.g., trichloroethyloxycarbonyl (Troc) is suitable. As an acyl radical, e.g., formyl, acetyl, propionyl, isopropionyl, trichloromethylcarbonyl, pivalyl, butyryl or benzoyl, which radical can be substituted with an amino and/or hydroxy group, is suitable.

As amino protective groups PG, the radicals that are known to one skilled in the art are suitable. For example, the Alloc, Boc, Z, benzyl, f-Moc, Troc, stabase or benzostabase group can be mentioned.

As halogen atoms, fluorine, chlorine, bromine or iodine can be considered.

The acyl groups can contain 1 to 20 carbon atoms, wherein formyl, acetyl, propionyl, isopropionyl and pivalyl groups are preferred.

The $C_2$-$C_{10}$-alkylene-$\alpha,\omega$-dioxy group that is possible for X is preferably an ethylene ketal or neopentyl ketal group.

Preferred compounds of general formula I are those in which A-Y represents O—C(=O) or $NR^{21}$—C(=O); D-E represents an $H_2C$—$CH_2$ group; G represents a $CH_2$ group; Z represents an oxygen atom; $R^{1a}$, $R^{1b}$ in each case represent $C_1$-$C_{10}$ alkyl or together a —$(CH_2)_p$ group with p equal to 2 or 3 or 4; $R^{2a}$, $R^{2b}$, independently of one another, represent hydrogen, $C_1$-$C_{10}$ alkyl, $C_2$-$C_{10}$ alkenyl, or $C_2$-$C_{10}$ alkynyl; $R^3$ represents hydrogen; $R^{4a}$, $R^{4b}$, independently of one another, represent hydrogen or $C_1$-$C_{10}$ alkyl; $R^5$ represents hydrogen, or $C_1$-$C_4$ alkyl or $CH_2OH$ or $CH_2NH_2$ or $CH_2N$(alkyl, acyl)$_{1,2}$ or $CH_2Hal$; $R^6$ and $R^7$ together represent an additional bond or together an NH group or together an N-alkyl group or together a $CH_2$ group or together an oxygen atom; W represents a group C(=X)$R^8$ or a 2-methyl-benzothiazol-5-yl radical or a 2-methylbenzoxazol-5-yl radical or a quinolin-7-yl radical or a 2-aminomethylbenzothiazol-5-yl radical or a 2-hydroxymethylbenzothiazol-5-yl radical or a 2-aminomethylbenzoxazol-5-yl radical or a 2-hydroxymethylbenzoxazol-5-yl radical; X represents a $CR^{10}R^{11}$ group; $R^8$ represents hydrogen or $C_1$-$C_4$ alkyl or a fluorine atom or a chlorine atom or a bromine atom; $R^{10}/R^{11}$ represent hydrogen/2-methylthiazol-4-yl or hydrogen/2-pyridyl or hydrogen/2-methyloxazol-4-yl or hydrogen/2-aminomethylthiazol-4-yl or hydrogen/2-aminomethyloxazol-4-yl or hydrogen/2-hydroxymethylthiazol-4-yl or hydrogen/2-hydroxymethyloxazol-4-yl.

As linkers of general formula (III), compounds are preferred in which V represents a bond or an aryl radical, o is equal to zero, and T represents an oxygen atom.

As linkers of general formula (III), in addition compounds are preferred in which V represents a bond or an aryl radical or a group

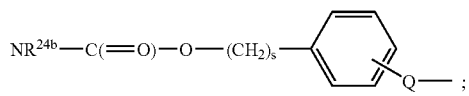

Q represents a bond or a group

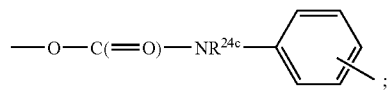

and o is 0 to 4. Especially preferred are compounds of general formula (III), wherein V represents a bond or a group

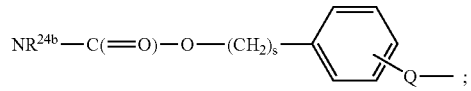

Q represents a bond or a group

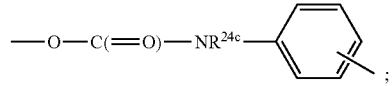

o is equal to 0, 2 or 3; s is equal to 1; and T is an oxygen atom.

As linkers of general formula (IV), compounds are preferred in which o is zero to four, and q is zero to three. Especially preferred are compounds of general formula (IV), wherein o is 0, 2 or 3; $W^1$ is an oxygen atom; q is equal to 0; $R^{22}$ is hydrogen, $C_1$-$C_3$ alkyl or aralkyl; $R^{23}$ is hydrogen or $C_1$-$C_3$ alkyl; $R^{24a}$ is hydrogen or $C_1$-$C_3$ alkyl; $R^{27}$ is fluorine, chlorine, CN, $NO_2$, $CO_2R^{28}$ or $OR^{28}$; $R^{28}$ is hydrogen or $C_1$-$C_5$ alkyl; and U is oxygen, $CHR^{22}$ or $CHR^{22}$—$NR^{23}C(=O)$—.

As recombinant proteins for use as recognition units, for example, binding regions derived from antibodies, so-called CDRs, are suitable.

As framework structures for use as recognition units, for example, high-molecular structures that are not derived from antibodies are suitable. For example, structures of the fibronectin type 3 and of crystallins can be mentioned.

As fragments of monoclonal antibodies for use as recognition units, for example, single-chain Fv, Fab, F(ab)$_2$ as well as recombinant multimers can be mentioned.

As preferred recognition units, those are considered that are suitable for, for example, the recognition and/or diagnosis and/or therapy of solid tumors and malignant diseases of the hematopoietic system.

As recognition units that are additionally preferred, those are considered that allow a selective recognition of the disease-specific vascular system, preferably of the angiogenesis.

Table 1 cites examples of especially preferred recognition units for treating solid tumors.

TABLE 1

| Tumor | Antigen Identity/Characteristics | Monoclonal Antibodies | References |
| --- | --- | --- | --- |
| Gynecol. (GY) | CA 125' >200 kD mucin GP | OC 125 | Kabawat et al., 1983; Szymendera, 1986 |

TABLE 1-continued

| Tumor | Antigen Identity/ Characteristics | Monoclonal Antibodies | References |
|---|---|---|---|
| Ovarian | 80 Kd GP | OC 133 | Masuko et al., Cancer Res, 1984 |
| Ovarian | 'SGA' 360 Kd GP | OMI | de Krester et al., 1986 |
| Ovarian | High $M_r$ mucin | Mo v1 | Miotti et al., Cancer Res, 1985 |
| Ovarian | High $M_r$ mucin/ glycolipid | Mo v2 | Miotti et al., Cancer Res, 1985 |
| Ovarian | NS | 3C2 | Tsuji et al., Cancer Res, 1985 |
| Ovarian | NS | 4C7 | Tsuji et al., Cancer Res, 1985 |
| Ovarian | High $M_r$ mucin | ID3 | Gangopadhyay et al., 1985 |
| Ovarian | High $M_r$ mucin | DU-PAN-2 | Lan et al., 1985 |
| GY | 7700 Kd GP | F 36/22 | Croghan et al., 1984 |
| Ovarian | 'gp 68' 48 Kd GP | $4F_7/7A_{10}$ | Bhattacharya et al., 1984 |
| GY | 40, 42 kD GP | OV-TL3 | Poels et al., 1986 |
| GY | 'TAG-72' High $M_r$ mucin | B72.3 | Thor et al., 1986 |
| Ovarian | 300-400 Kd GP | $DF_3$ | Kufe et al., 1984 |
| Ovarian | 60 Kd GP | $2C_8/2F_7$ | Bhattacharya et al., 1985 |
| GY | 105 Kd GP | MF 116 | Mattes et al., 1984 |
| Ovarian | 38-40 kD GP | Mov18 | Miotti et al., 1987 |
| GY | 'CEA' 180 Kd GP | CEA 11-H5 | Wagener et al., 1984 |
| Ovarian | CA 19-9 or GICA | CA 19-9 (1116NS 19-9) | Atkinson et al., 1982 |
| Ovarian | 'FLAP' 67 Kd GP | H17-E2 | McDicken et al., 1985 |
| Ovarian | 72 Kd | 791T/36 | Perkins et al., 1985 |
| Ovarian | 69 Kd PLAP | $NDOG_2$ | Sunderland et al., 1984 |
| Ovarian | unknown $M_r$ PLAP | H317 | Johnson et al., 1981 |
| Ovarian | $p185^{HER2}$ | 4D5, 3H4, 7C2, 6E9, 2C4, 7F3, 2H11, 3E8, 5B8, 7D3, SB8 | Shepard et al., 1991 |
| Uterus, Ovary | HMFG-2 | HMFG2 | Epenetos et al., 1982 |
| GY | HMFG-2 | 3.14.A3 | Burchell et al., 1983 |
| Breast | 330-450 Kd GP | DF3 | Hayes et al., 1985 |
| Breast | NS | NCRC-11 | Ellis et al., 1984 |
| Breast | 37 kD | 3C6F9 | Mandeville et al., 1987 |
| Breast | NS | MBE6 | Teramoto et al., 1982 |
| Breast | NS | CLNH5 | Glassy et al., 1983 |
| Breast | 47 Kd GP | MAC 40/43 | Kjeldsen et al., 1986 |
| Breast | High $M_r$ GP | EMA | Sloane et al., 1981 |
| Breast | High $M_r$ GP | HMFG1 HFMG2 | Arklie et al., 1981 |
| Breast | NS | 3.15.C3 | Arklie et al., 1981 |
| Breast | NS | M3, M8, M24 | Foster et al., 1982 |
| Breast | 1 (Ma) Blood Group Ags | M18 | Foster et al., 1984 |
| Breast | NS | 67-D-11 | Rasmussen et al., 1982 |
| Breast | Estrogen Receptor | D547Sp, D75P3, H222 | Kinsel et al., 1989 |
| Breast | EGF Receptor | Anti EGF | Sainsbury et al., 1985 |
| Breast | Laminine Receptor | LR-3 | Horan Hand et al., 1985 |
| Breast | erb B-2 p185 | TA1 | Gusterson et al., 1988 |
| Breast | NS | H59 | Hendler et al., 1981 |
| Breast | 126 Kd GP | 10-3D-2 | Soule et al., 1983 |
| Breast | NS | HmAB1,2 | Imam et al., 1984; Schlom et al., 1985 |
| Breast | NS | MBR 1, 2, 3 | Menard et al., 1983 |
| Breast | 95 Kd | 24-17-1 | Thompson et al., 1983 |
| Breast | 100 Kd | 24-17-2 (3E1-2) | Croghan et al., 1983 |
| Breast | NS | F36/22.M7/105 | Croghan et al., 1984 |
| Breast | 24 Kd | C11, G3, H7 | Adams et al., 1983 |
| Breast | 90 Kd GP | B6-2 | Colcher et al., 1981 |
| Breast | CEA & 180 Kd GP | B1-1 | Colcher et al., 1983 |
| Breast | Colon & pancreas, mucin-like Ca 19-9 | Cam 17-1 | Imperial Cancer Research Technology MAb listing |
| Breast | Milk mucin, nuclear protein | SM3 | Imperial Cancer Research Technology Mab listing |
| Breast | Milk mucin, nuclear protein | SM4 | Imperial Cancer Research Technology Mab listing |

TABLE 1-continued

| Tumor | Antigen Identity/ Characteristics | Monoclonal Antibodies | References |
|---|---|---|---|
| Breast | Affinity-purified milk mucin | C-Mul (566) | Imperial Cancer Research Technology Mab listing |
| Breast | P185$^{HER2}$ | 4D5 3H4, 7C2, 6E9, 2C4, 7F3, 2H11, 3E8, 5B8, 7D3, 5B8 | Shepard et al., 1991 |
| Breast | CA 125 >200 Kd GP | OC 125 | Kabawat et al., 1985 |
| Breast | High $M_r$ mucin/ glycolipid | MO v2 | Miotti et al., 1985 |
| Breast | High $M_r$ mucin | DU-PAN-2 | Lan et al., 1984 |
| Breast | 'gp48' 48 Kd GP | $4F_7/7A_{10}$ | Bhattacharya et al., 1984 |
| Breast | 300-400 Kd GP | $DF_3$ | Kufe et al., 1984 |
| Breast | 'TAG-72' high $M_r$ mucin | B72-3 | Thor et al., 1986 |
| Breast | 'CEA' 180 Kd GP | cccccCEA 11 | Wagener et at., 1984 |
| Breast | 'PLAP' 67 Kd GP | H17-E2 | McDicken et al., 1985 |
| Breast | HMFG-2 >400 Kd GP | 3-14-A3 | Burchell et at., 1983 |
| Breast | NS | FO23C5 | Riva et at., 1988 |
| Colorectal | TAG-72 High $M_r$ mucin | B72-3 | Colcher et at., 1987 |
| Colorectal | GP37 | (17-1A) 1038-17-1A | Paul et al., 1986 |
| Colorectal | Surface GP | CO17-1A | LoBuglio et al., 1988 |
| Colorectal | CEA | ZCE-025 | Patt et al., 1988 |
| Colorectal | CEA | AB2 | Griffin et al., 1988a |
| Colorectal | Cell surface AG | HT-29-15 | Cohn et al., 1987 |
| Colorectal | Secretory epithelium | 250-30.6 | Leydem et al., 1986 |
| Colorectal | Surface glycoprotein | 44X14 | Gallagher et al., 1986 |
| Colorectal | NS | A7 | Takahashi et al., 1988 |
| Colorectal | NS | GA73-3 | Munz et al., 1986 |
| Colorectal | NS | 791T/36 | Farrans et al., 1982 |
| Colorectal | Cell Membrane & Cytoplasmatic Ag | 28A32 | Smith et al., 1987 |
| Colorectal | CEA & Vindesin | 28.19.8 | Corvalen, 1987 |
| Colorectal | gp72 | X MMCO-791 | Byers et al., 1987 |
| Colorectal | high $M_r$ mucin | DU-PAN-2 | Lan et al., 1985 |
| Colorectal | high $M_r$ mucin | $ID_3$ | Gangopadhyay et al., 1985 |
| Colorectal | CEA 180 Kd GP | CEA 11-H5 | Wagener et al., 1984 |
| Colorectal | 60 Kd GP | $2C_8/2F_7$ | Bhattacharya et al., 1985 |
| Colorectal | CA-19-9 (or GICA) | CA-19-9 (1116NS 19-9) | Atkinson et al., 1982 |
| Colorectal | Lewis a | PR5C5 | Imperial Cancer Research Technology Mab Listing |
| Colorectal | Lewis a | PR4D2 | Imperial Cancer Research Technology Mab Listing |
| Colorectal | Colon mucus | PR4D1 | Imperial Cancer Research Technology Mab Listing |
| Melanoma | P97$^a$ | 4-1 | Woodbury et al., 1980 |
| Melanoma | P97$^a$ | 8-2 $M_{17}$ | Brown, et al., 1981a |
| Melanoma | P97$^b$ | 96-5 | Brown, et al., 1981a |
| Melanoma | P97$^c$ | 118-1, 133-2, (113-2) | Brown, et al., 1981a |
| Melanoma | P97$^c$ | $L_1, L_{10}, R_{10}$ ($R_{19}$) | Brown et al., 1981b |
| Melanoma | P97$^d$ | $I_{12}$ | Brown et al., 1981b |
| Melanoma | P97$^e$ | $K_5$ | Brown et al., 1981b |
| Melanoma | P155 | 6-1 | Loop et al., 1981 |
| Melanoma | $G_{D3}$ disialogangliosides | R24 | Dippold et al., 1980 |
| Melanoma | P210, p60, p250 | 5-1 | Loop et al., 1981 |
| Melanoma | P280 p440 | 225.28S | Wilson et al., 1981 |
| Melanoma | GP 94, 75, 70 & 25 | 465.12S | Wilson et al., 1981 |
| Melanoma | P240-P250, P450 | 9-2-27 | Reisfeld et al., 1982 |
| Melanoma | 100, 77, 75 Kd | F11 | Chee et al., 1982 |
| Melanoma | 94 Kd | 376.96S | Imai et al., 1982 |
| Melanoma | 4 GP Chains | 465.12S | Imai et al., 1982; Wilson et al., 1981 |
| Melanoma | GP 74 | 15-75 | Johnson & Reithmuller, 1982 |
| Melanoma | GP 49 | 15-95 | Johnson & Reithmuller, 1982 |

TABLE 1-continued

| Tumor | Antigen Identity/ Characteristics | Monoclonal Antibodies | References |
|---|---|---|---|
| Melanoma | 230 Kd | Mel-14 | Carrel et al., 1982 |
| Melanoma | 92 Kd | Mel-12 | Carrel et al., 1982 |
| Melanoma | 70 Kd | Me3-TB7 | Carrel et al., 1: 387, 1982 |
| Melanoma | HMW MAA similar to 9-2-27 AG | 225.28SD | Kantor et al., 1982 |
| Melanoma | HMW MAA similar to 9-2-27 AG | 763.24TS | Kantor et al., 1982 |
| Melanoma | GP95 similar to 376-96S 465-12S | 705F6 | Stuhlmiller et al., 1982 |
| Melanoma | GP125 | 436910 | Saxton et al., 1982 |
| Melanoma | CD41 | M148 | Imperial Cancer Research Technology Mab listing |
| Gastrointestinal (GI) | high $M_r$ mucin | ID3 | Gangopadhyay et al., 1985 |
| Gallbladder, Pancreas, Stomach | high $M_r$ mucin | DU-PAN-2 | Lan et al., 1985 |
| Pancreas | NS | OV-TL3 | Poels et al., 1984 |
| Pancreas, Stomach, Esophagus | 'TAG-72' high $M_r$ mucin | B72-3 | Thor et al., 1986 |
| Stomach | 'CEA' 180 Kd GP | CEA 11-H5 | Wagener et al., 1984 |
| Pancreas | HMFG-2 >400 Kd GP | 3-14-A3 | Burchell et al., 1983 |
| GI | NS | C COLI | Lemkin et al., 1984 |
| Pancreas, Stomach | CA 19-9 (or GICA) | CA-19-9 (1116NS 19-9) and CA50 | Szymendera, 1986 |
| Pancreas | CA125 GP | OC125 | Szymendera, 1986 |
| Lung Non-small-cell lung cancer (NSCLC) | $p185^{HER2}$ | 4D5, 3H4, 7C2, 6E9, 2C4, 7F3, 2H11, 3E8, 5B8, 7D3, SB8 | Shepard et al., 1991 |
| NSCLC | high $M_r$ mucin/glycolipid | MO v2 | Miotti et al., 1985 |
| NSCLC | 'TAG -72' high $M_r$ mucin | B72-3 | Thor et al., 1986 |
| NSCLC | High $M_r$ mucin | DU-PAN-2 | Lan et al., 1985 |
| NSCLC | 'CEA' 180 kD GP | CEA 11-H5 | Wagener et al., 1984 |
| Malignant Glioma | Cytoplastic antigen that consists of 85HG-22 cells | MUG 8-22 | Stavrou, 1990 |
| Malignant Glioma | Cell surface Ag that consists of 85HG-\63 cells | MUC 2-63 | Stavrou, 1990 |
| Malignant Glioma | Cell surface Ag that consists of 86HG-39 cells | MUC 2-39 | Stavrou, 1990 |
| Malignant Glioma | Cell surface Ag that consists of 86HG-39 cells | MUG 7-39 | Stavrou, 1990 |
| GC, Other | P53 | PAb 240, PAb 246, PAb 1801 | Imperial Cancer Research Technology MaB Listing |
| Small, Round-Cell Tumors | Neural cell adhesion molecules | ERIC-1 | Imperial Cancer Research Technology MaB Listing |
| Medulloblastomas, Neuroblastomas, Rhabdomyo-sarcomas | | M148 | Imperial Cancer Research Technology MaB Listing |
| Neuroblastomas | | FMH25 | Imperial Cancer Research Technology MaB Listing |
| Kidneys & Glioblastomas | P155 | 6-1 | Loop et al., 1981 |
| Bladders & Laryngeal Tumors | "Ca Antigen" 350-390 kD | CA1 | Ashall et al., 1982 |
| Neuroblastoma | GD2 | 3F8 | Cheung et al., 1986 |
| Prostate | Gp48 48 kD GP | $4F_7/7A_{10}$ | Bhattacharya et al., 1984 |
| Prostate | 60 kD GP | $2C_8/2F_7$ | Bhattacharya et al., 1985 |
| Thyroid | 'CEA' 180 kD GP | CEA 11-H5 | Wagener et al., 1984 |

TABLE 1-continued

| Tumor | Antigen Identity/ Characteristics | Monoclonal Antibodies | References |
|---|---|---|---|
| Prostata | Neurocellin-2 (NC-2), TMEFF2, TENB2, tomoregulin, TMP-2 | 2H8, 10G6 | Berlex |

As especially preferred recognition units for treating hematological tumors, antibodies or antibody fragments, such as CD19, CD20, CD40, CD22, CD25, CD5, CD52, CD10, CD2, CD7, CD33, CD38, CD40, CD72, CD4, CD21, CD5, CD37 and CD30, can also be mentioned.

As especially preferred recognition units for anti-angiogenic therapy, antibodies or fragments thereof, such as VCAM, CD31, ELAM, endoglin, VEGFRI/II, $\alpha_v\beta_3$, Tie1/2, TES23 (CD44ex6), phosphatidylserine, PSMA, VEGFR/VEGF complex or ED-B-fibronectin, can be mentioned.

The compounds that are mentioned below are especially preferred according to the invention as effector elements:

(4S,7R,8S,9S,13Z,16S(E))-4,8-Dihydroxy-5,5,7,9,13-pentamethyl-16-[1-methyl-2-(2-methyl-thiazol-4-yl)-vinyl]-oxacyclohexadec-13-ene-2,6-dione, (4S,7R,8S,9S,13Z,16S(E))-4,8-Dihydroxy-16-[2-(2-hydroxymethyl-thiazol-4-yl)-1-methyl-vinyl]-5,5,7,9,13-pentamethyl-oxacyclohexadec-13-ene-2,6-dione, (4S,7R,8S,9S,13Z,16S(E))-16-[2-(2-Aminomethyl-thiazol-4-yl)-1-methyl-vinyl]-4,8-dihydroxy-5,5,7,9,13-pentamethyl-oxacyclohexadec-13-ene-2,6-dione, (1S,3S(E),7S,10R,11S,12S,16R)-7,11-Dihydroxy-8,8,10,12,16-pentamethyl-3-[1-methyl-2-(2-methyl-thiazol-4-yl)-vinyl]-4,17-dioxa-bicyclo[14.1.0]heptadecane-5,9-dione, (1S,3S(E),7S,10R,11S,12S,16R)-7,11-Dihydroxy-3-[2-(2-hydroxymethyl-thiazol-4-yl)-1-methyl-vinyl]-8,8,10,12,16-pentamethyl-4,17-dioxa-bicyclo[14.1.0]heptadecane-5,9-dione, (1S,3S(E),7S,10R,11S,12S,16R)-3-[2-(2-Aminomethyl-thiazol-4-yl)-1-methyl-vinyl]-7,11-dihydroxy-8,8,10,12,16-pentamethyl-4,17-dioxa-bicyclo[14.1.0]heptadecane-5,9-dione, (4S,7R,8S,9S,13Z,16S(E))-4,8-Dihydroxy-7-ethyl-5,5,9,13-tetramethyl-16-[1-methyl-2-(2-methyl-thiazol-4-yl)-vinyl]-oxacyclohexadec-13-ene-2,6-dione, (4S,7R,8S,9S,13Z,16S(E))-4,8-Dihydroxy-16-[2-(2-hydroxymethyl-thiazol-4-yl)-1-methyl-vinyl]-7-ethyl-5,5,9,13-tetramethyl-oxacyclohexadec-13-ene-2,6-dione, (4S,7R,8S,9S,13Z,16S(E))-16-[2-(2-Aminomethyl-thiazol-4-yl)-1-methyl-vinyl]-4,8-dihydroxy-7-ethyl-5,5,9,13-tetramethyl-oxacyclohexadec-13-ene-2,6-dione, (1S,3S(E),7S,10R,11S,12S,16R)-7,11-Dihydroxy-10-ethyl-8,8,12,16-tetramethyl-3-[1-methyl-2-(2-methyl-thiazol-4-yl)-vinyl]-4,17-dioxa-bicyclo[14.1.0]heptadecane-5,9-dione, (1S,3S(E),7S,10R,11S,12S,16R)-7,11-Dihydroxy-3-[2-(2-hydroxymethyl-thiazol-4-yl)-1-methyl-vinyl]-10-ethyl-8,8,12,16-tetramethyl-4,17-dioxa-bicyclo[14.1.0]heptadecane-5,9-dione, (1S,3S(E),7S,10R,11S,12S,16R)-3-[2-(2-Aminomethyl-thiazol-4-yl)-1-methyl-vinyl]-7,11-dihydroxy-10-ethyl-8,8,12,16-tetramethyl-4,17-dioxa-bicyclo[14.1.0]heptadecane-5,9-dione, (4S,7R,8S,9S,13Z,16S(Z))-4,8-Dihydroxy-5,5,7,9,13-pentamethyl-16-[1-fluoro-2-(2-methyl-thiazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-thiazol-4-yl)-1-fluoro-vinyl]-5,5,7,9,13-pentamethyl-oxacyclohexadec-13-ene-2,6-dione, (4S,7R,8S,9S,13Z,16S(Z))-16-[2-(2-Aminomethyl-thiazol-4-yl)-1-fluoro-vinyl]-4,8-dihydroxy-5,5,7,9,13-pentamethyl-oxacyclohexadec-13-ene-2,6-dione, (1S,3S(Z),7S,10R,11S,12S,16R)-7,11-Dihydroxy-8,8,10,12,16-pentamethyl-3-[1-fluoro-2-(2-methyl-thiazol-4-yl)-vinyl]-4,17-dioxa-bicyclo [14.1.0]heptadecane-5,9-dione, (1S,3S(Z),7S,10R,11S,12S,16R)-7,11-Dihydroxy-3-[2-(2-hydroxymethyl-thiazol-4-yl)-1-fluoro-vinyl]-8,8,10,12,16-pentamethyl-4,17-dioxa-bicyclo[14.1.0]heptadecane-5,9-dione, (1S,3S(Z),7S,10R,11S,12S,16R)-3-[2-(2-Aminomethyl-thiazol-4-yl)-1-fluoro-vinyl]-7,11-dihydroxy-8,8,10,12,16-pentamethyl-4,17-dioxa-bicyclo[14.1.0]heptadecane-5,9-dione, (4S,7R,8S,9S,13Z,16S(Z))-4,8-Dihydroxy-5,5,7,9,13-pentamethyl-16-[1-chloro-2-(2-methyl-thiazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-thiazol-4-yl)-1-chloro-vinyl]-5,5,7,9,13-pentamethyl-oxacyclohexadec-13-ene-2,6-dione, (4S,7R,8S,9S,13Z,16S(Z))-16-[2-(2-Aminomethyl-thiazol-4-yl)-1-chloro-vinyl]-4,8-dihydroxy-5,5,7,9,13-pentamethyl-oxacyclohexadec-13-ene-2,6-dione, (1S,3S(Z),7S,10R,11S,12S,16R)-7,11-Dihydroxy-8,8,10,12,16-pentamethyl-3-[1-chloro-2-(2-methyl-thiazol-4-yl)-vinyl]-4,17-dioxa-bicyclo[14.1.0]heptadecane-5,9-dione, (1S,3S(Z),7S,10R,11S,12S,16R)-7,11-Dihydroxy-3-[2-(2-hydroxymethyl-thiazol-4-yl)-1-chloro-vinyl]-8,8,10,12,16-pentamethyl-4,17-dioxa-bicyclo[14.1.0]heptadecane-5,9-dione, (1S,3S(Z),7S,10R,11S,12S,16R)-3-[2-(2-Aminomethyl-thiazol-4-yl)-1-chloro-vinyl]-7,11-dihydroxy-8,8,10,12,16-pentamethyl-4,17-dioxa-bicyclo[14.1.0]heptadecane-5,9-dione, (4S,7R,8S,9S,13Z,16S(Z))-4,8-Dihydroxy-7-ethyl-5,5,9,13-tetramethyl-16-[1-fluoro-2-(2-methyl-thiazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-thiazol-4-yl)-1-fluoro-vinyl]-7-ethyl-5,5,9,13-tetramethyl-oxacyclohexadec-13-ene-2,6-dione, (4S,7R,8S,9S,13Z,16S(Z))-16-[2-(2-Aminomethyl-thiazol-4-yl)-1-fluoro-vinyl]-4,8-dihydroxy-7-ethyl-5,5,9,13-tetramethyl-oxacyclohexadec-13-ene-2,6-dione, (1S,3S(Z),7S,10R,11S,12S,16R)-7,11-Dihydroxy-10-ethyl-8,8,12,16-tetramethyl-3-[1-fluoro-2-(2-methyl-thiazol-4-yl)-vinyl]-4,17-dioxa-bicyclo[14.1.0]heptadecane-5,9-dione, (1S,3S(Z),7S,10R,11S,12S,16R)-7,11-Dihydroxy-3-[2-(2-hydroxymethyl-thiazol-4-yl)-1-fluoro-vinyl]-10-ethyl-8,8,12,16-tetramethyl-4,17-dioxa-bicyclo[14.1.0]heptadecane-5,9-dione, (1S,3S(Z),7S,10R,11S,12S,16R)-3-[2-(2-Aminomethyl-thiazol-4-yl)-1-fluoro-vinyl]-7,11-dihydroxy-10-ethyl-8,8,12,16-tetramethyl-4,17-dioxa-bicyclo[14.1.0]heptadecane-5,9-dione, (4S,7R,8S,9S,13Z,16S(Z))-4,8-Dihydroxy-7-ethyl-5,5,9,13-tetramethyl-16-[1-chloro-2-(2-methyl-thiazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-thiazol-4-yl)-1-chloro-vinyl]-7-ethyl-5,5,9,13-tetramethyl-oxacyclohexadec-13-ene-2,6-dione, (4S,7R,8S,9S,13Z,16S(Z))-16-[2-(2-Aminomethyl-thiazol-4-yl)-1-chloro-vinyl]-4,8-dihydroxy-7-ethyl-5,5,9,13-tetramethyl-oxacyclohexadec-13-ene-2,6-dione, (1S,3S(Z),7S,10R,11S,12S,16R)-7,11-Dihydroxy-10-ethyl-8,8,12,16-tetramethyl-3-[1-chloro-2-(2-methyl-thiazol-4-yl)-vinyl]-4,17-dioxa-bicyclo[14.1.0]heptadecane-5,9-dione, (1S,3S(Z),7S,10R,11S,12S,16R)-7,11-Dihydroxy-3-[2-(2-hydroxymethyl-thiazol-4-yl)-1-chloro-vinyl]-10-ethyl-8,8,12,16-tetramethyl-4,17-dioxa-bicyclo[14.1.0]heptadecane-5,9-dione, (1S,3S(Z),7S,10R,11S,12S,16R)-3-[2-(2-Aminomethyl-thiazol-4-yl)-1-chloro-vinyl]-7,11-dihydroxy-10-ethyl-8,8,12,16-tetramethyl-4,17-dioxa-bicyclo [14.1.0]heptadecane-5,9-dione, (4S,7R,8S,9S,13Z,16S(E))-4,8-Dihydroxy-5,5,7,9,13-pentamethyl-16-[1-methyl-2-(2-pyridyl)-vinyl]-oxacyclohexadec-13-ene-2,6-dione, (1S,3S(E),7S,10R,11S,12S,16R)-7,11-Dihydroxy-8,8,10,12,16-pentamethyl-3-[1-methyl-2-(2-pyridyl)-vinyl]-4,17-dioxa-bicyclo[14.1.0]heptadecane-5,9-dione, (4S,7R,8S,9S,13Z,16S(E))-4,8-Dihydroxy-7-ethyl-5,5,9,13-tetramethyl-16-[1-methyl-2-(2-pyridyl)-vinyl]-oxacyclohexadec-13-ene-2,6-dione, (1S,3S(E),7S,10R,11S,12S,16R)-7,11-Dihydroxy-10-ethyl-8,8,12,16-tetramethyl-3-[1-methyl-2-(2-pyridyl)-vinyl]-4,17-dioxa-bicyclo [14.1.0]heptadecane-5,9-dione, (4S,7R,8S,9S,13Z,16S(Z))-4,8-Dihydroxy-5,5,7,9,13-pentamethyl-16-[1-fluoro-2-(2-pyridyl)-vinyl]-oxacyclohexadec-13-ene-2,6-dione, (1S,3S(Z),7S,10R,11S,12S,16R)-7,11-Dihydroxy-8,8,10,12,16-pentamethyl-3-[1-fluoro-2-(2-pyridyl)-vinyl]-4,17-dioxa-bicyclo[14.1.0]heptadecane-5,9-dione, (4S,7R,8S,9S,13Z,16S(Z))-4,8-Dihydroxy-5,5,7,9,13-pentamethyl-16-[1-chloro-2-(2-pyridyl)-vinyl]-oxacyclohexadec-13-ene-2,6-dione, (1S,3S(Z),7S,10R,11S,12S,16R)-7,11-Dihydroxy-8,8,10,12,16-pentamethyl-3-[1-chloro-2-(2-pyridyl)-vinyl]-4,17-dioxa-bicyclo[14.1.0]heptadecane-5,9-dione, (4S,7R,8S,9S,13Z,16S(Z))-4,8-Dihydroxy-7-ethyl-5,5,9,13-tetramethyl-16-[1-fluoro-2-(2-pyridyl)-vinyl]-oxacyclohexadec-13-ene-2,6-dione, (1S,3S(Z),7S,10R,11S,12S,16R)-7,11-Dihydroxy-10-ethyl-8,8,12,16-tetramethyl-3-[1-fluoro-2-(2-pyridyl)-vinyl]-4,17-dioxa-bicyclo[14.1.0]heptadecane-5,9-dione, (4S,7R,8S,9S,13Z,16S(Z))-4,8-Dihydroxy-7-ethyl-5,5,9,13-tetramethyl-16-[1-chloro-2-(2-pyridyl)-vinyl]-oxacyclohexadec-13-ene-2,6-dione, (1S,3S(Z),7S,10R,11S,12S,16R)-7,11-Dihydroxy-10-ethyl-8,8,12,16-tetramethyl-3-[1-chloro-2-(2-pyridyl)-vinyl]-4,17-dioxa-bicyclo[14.1.0]heptadecane-5,9-dione, (4S,7R,8S,9S,13Z,16S(E))-4,8-Dihydroxy-5,5,7,9,13-pentamethyl-16-[1-methyl-2-(2-methyl-oxazol-4-yl)-vinyl]-oxacyclohexadec-13-ene-2,6-dione, (4S,7R,8S,9S,13Z,16S(E))-4,8-Dihydroxy-16-[2-(2-hydroxymethyl-oxazol-4-yl)-1-methyl-vinyl]-5,5,7,9,13-pentamethyl-oxacyclohexadec-13-ene-2,6-dione, (4S,7R,8S,9S,13Z,16S(E))-16-[2-(2-Aminomethyl-oxazol-4-yl)-1-methyl-vinyl]-4,8-dihydroxy-5,5,7,9,13-pentamethyl-oxacyclohexadec-13-ene-2,6-dione, (1S,3S(E),7S,10R,11S,12S,16R)-7,11-Dihydroxy-8,8,10,12,16-pentamethyl-3-[1-methyl-2-(2-methyl-oxazol-4-yl)-vinyl]-4,17-dioxa-bicyclo[14.1.0]heptadecane-5,9-dione, (1S,3S(E),7S,10R,11S,12S,16R)-7,11-Dihydroxy-3-[2-(2-hydroxymethyl-oxazol-4-yl)-1-methyl-vinyl]-8,8,10,12,16-pentamethyl-4,17-dioxa-bicyclo[14.1.0]heptadecane-5,9-dione, (1S,3S(E),7S,10R,11S,12S,16R)-3-[2-(2-Aminomethyl-oxazol-4-yl)-1-methyl-vinyl]-7,11-dihydroxy-8,8,10,12,16-pentamethyl-4,17-dioxa-bicyclo[14.1.0]heptadecane-5,9-dione, (4S,7R,8S,9S,13Z,16S(E))-4,8-Dihydroxy-7-ethyl-5,5,9,13-tetramethyl-16-[1-methyl-2-(2-methyl-oxazol-4-yl)-vinyl]-oxacyclohexadec-13-ene-2,6-dione, (4S,7R,8S,9S,13Z,16S(E))-4,8-Dihydroxy-16-[2-(2-hydroxymethyl-oxazol-4-yl)-1-methyl-vinyl]-7-ethyl-5,5,9,13-tetramethyl-oxacyclohexadec-13-ene-2,6-dione, (4S,7R,8S,9S,13Z,16S(E))-16-[2-(2-Aminomethyl-oxazol-4-yl)-1-methyl-vinyl]-4,8-dihydroxy-7-ethyl-5,5,9,13-tetramethyl-oxacyclohexadec-13-ene-2,6-dione, (1S,3S(E),7S,10R,11S,12S,16R)-7,11-Dihydroxy-10-ethyl-8,8,12,16-tetramethyl-3-[1-methyl-2-(2-methyl-oxazol-4-yl)-vinyl]-4,17-dioxa-bicyclo[14.1.0]heptadecane-5,9-dione, (1S,3S(E),7S,10R,11S,12S,16R)-7,11-Dihydroxy-3-[2-(2-hydroxymethyl-oxazol-4-yl)-1-methyl-vinyl]-10-ethyl-8,8,12,16-tetramethyl-4,17-dioxa-bicyclo[14.1.0]heptadecane-5,9-dione, (1S,3S(E),7S,10R,11S,12S,16R)-3-[2-(2-Aminomethyl-oxazol-4-yl)-1-methyl-vinyl]-7,11-dihydroxy-10-ethyl-8,8,12,16-tetramethyl-4,17-dioxa-bicyclo[14.1.0]heptadecane-5,9-dione, (4S,7R,8S,9S,13Z,16S(Z))-4,8-Dihydroxy-5,5,7,9,13-pentamethyl-16-[1-fluoro-2-(2-methyl-oxazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-oxazol-4-yl)-1-fluoro-vinyl]-5,5,7,9,13-pentamethyl-oxacyclohexadec-13-ene-2,6-dione, (4S,7R,8S,9S,13Z,16S(Z))-16-[2-(2-Aminomethyl-oxazol-4-yl)-1-fluoro-vinyl]-4,8-dihydroxy-5,5,7,9,13-pentamethyl-oxacyclohexadec-13-ene-2,6-dione, (1S,3S(Z),7S,10R,11S,12S,16R)-7,11-Dihydroxy-8,8,10,12,16-pentamethyl-3-[1-fluoro-2-(2-methyl-oxazol-4-yl)-vinyl]-4,17-dioxa-bicyclo[14.1.0]heptadecane-5,9-dione, (1S,3S(Z),7S,10R,11S,12S,16R)-7,11-Dihydroxy-3-[2-(2-hydroxymethyl-oxazol-4-yl)-1-fluoro-vinyl]-8,8,10,12,16-pentamethyl-4,17-dioxa-bicyclo[14.1.0]heptadecane-5,9-dione, (1S,3S(Z),7S,10R,11S,12S,16R)-3-[2-(2-Aminomethyl-oxazol-4-yl)-1-fluoro-vinyl]-7,11-dihydroxy-8,8,10,12,16-pentamethyl-4,17-dioxa-bicyclo[14.1.0]heptadecane-5,9-dione, (4S,7R,8S,9S,13Z,16S(Z))-4,8-Dihydroxy-5,5,7,9,13-pentamethyl-16-[1-chloro-2-(2-methyl-oxazol-4-yl)-vinyl]-oxacyclohexadec-13-ene-2,6-dione, (4S,7R,8S,9S,13Z,16S(Z))-4,8-Dihydroxy-16-[2-(2-hydroxymethyl-oxazol-4-yl)-1-chloro-vinyl]-5,5,7,9,13-pentamethyl-oxacyclohexadec-13-ene-2,6-dione, (4S,7R,8S,9S,13Z,16S(Z))-16-[2-(2-Aminomethyl-oxazol-4-yl)-1-chloro-vinyl]-4,8-dihydroxy-5,5,7,9,13-pentamethyl-oxacyclohexadec-13-ene-2,6-dione, (1S,3S(Z),7S,10R,11S,12S,16R)-7,11-Dihydroxy-8,8,10,
12,16-pentamethyl-3-[1-chloro-2-(2-methyl-oxazol-4-
yl)-vinyl]-4,17-dioxa-bicyclo [14.1.0]heptadecane-5,9-
dione,
(1S,3S(Z),7S,10R,11S,12S,16R)-7,11-Dihydroxy-3-[2-(2-
hydroxymethyl-oxazol-4-yl)-1-chloro-vinyl]-8,8,10,12,
16-pentamethyl-4,17-dioxa-bicyclo[14.1.0]heptadecane-
5,9-dione,
(1S,3S(Z),7S,10R,11S,12S,16R)-3-[2-(2-Aminomethyl-ox-
azol-4-yl)-1-chloro-vinyl]-7,11-dihydroxy-8,8,10,12,16-
pentamethyl-4,17-dioxa-bicyclo[14.1.0]heptadecane-5,9-
dione,
(4S,7R,8S,9S,13Z,16S(Z))-4,8-Dihydroxy-7-ethyl-5,5,9,
13-tetramethyl-16-[1-fluoro-2-(2-methyl-oxazol-4-yl)-vi-
nyl]-oxacyclohexadec-13-ene-2,6-dione,
(4S,7R,8S,9S,13Z,16S(Z))-4,8-Dihydroxy-16-[2-(2-hy-
droxymethyl-oxazol-4-yl)-1-fluoro-vinyl]-7-ethyl-5,5,9,
13-tetramethyl-oxacyclohexadec-13-ene-2,6-dione,
(4S,7R,8S,9S,13Z,16S(Z))-16-[2-(2-Aminomethyl-oxazol-
4-yl)-1-fluoro-vinyl]-4,8-dihydroxy-7-ethyl-5,5,9,13-tet-
ramethyl-oxacyclohexadec-13-ene-2,6-dione,
(1S,3S(Z),7S,10R,11S,12S,16R)-7,11-Dihydroxy-10-ethyl-
8,8,12,16-tetramethyl-3-[1-fluoro-2-(2-methyl-oxazol-4-
yl)-vinyl]-4,17-dioxa-bicyclo[14.1.0]heptadecane-5,9-di-
one,
(1S,3S(Z),7S,10R,11S,12S,16R)-7,11-Dihydroxy-3-[2-(2-
hydroxymethyl-oxazol-4-yl)-1-fluoro-vinyl]-10-ethyl-8,
8,12,16-tetramethyl-4,17-dioxa-bicyclo[14.1.0]heptade-
cane-5,9-dione,
(1S,3S(Z),7S,10R,11S,12S,16R)-3-[2-(2-Aminomethyl-ox-
azol-4-yl)-1-fluoro-vinyl]-7,11-dihydroxy-10-ethyl-8,8,
12,16-tetramethyl-4,17-dioxa-bicyclo[14.1.0]heptade-
cane-5,9-dione,
(4S,7R,8S,9S,13Z,16S(Z))-4,8-Dihydroxy-7-ethyl-5,5,9,
13-tetramethyl-16-[1-chloro-2-(2-methyl-oxazol-4-yl)-
vinyl]-oxacyclohexadec-13-ene-2,6-dione,
(4S,7R,8S,9S,13Z,16S(Z))-4,8-Dihydroxy-16-[2-(2-hy-
droxymethyl-oxazol-4-yl)-1-chloro-vinyl]-7-ethyl-5,5,9,
13-tetramethyl-oxacyclohexadec-13-ene-2,6-dione,
(4S,7R,8S,9S,13Z,16S(Z))-16-[2-(2-Aminomethyl-oxazol-
4-yl)-1-chloro-vinyl]-4,8-dihydroxy-7-ethyl-5,5,9,13-tet-
ramethyl-oxacyclohexadec-13-ene-2,6-dione,
(1S,3S(Z),7S,10R,11S,12S,16R)-7,11-Dihydroxy-10-ethyl-
8,8,12,16-tetramethyl-3-[1-chloro-2-(2-methyl-oxazol-4-
yl)-vinyl]-4,17-dioxa-bicyclo[14.1.0]heptadecane-5,9-di-
one,
(1S,3S(Z),7S,10R,11S,12S,16R)-7,11-Dihydroxy-3-[2-(2-
hydroxymethyl-oxazol-4-yl)-1-chloro-vinyl]-10-ethyl-8,
8,12,16-tetramethyl-4,17-dioxa-bicyclo[14.1.0]heptade-
cane-5,9-dione,
(1S,3S(Z),7S,10R,11S,12S,16R)-3-[2-(2-Aminomethyl-ox-
azol-4-yl)-1-chloro-vinyl]-7,11-dihydroxy-10-ethyl-8,8,
12,16-tetramethyl-4,17-dioxa-bicyclo[14.1.0]heptade-
cane-5,9-dione,
(4S,7R,8S,9S,13Z,16S(E))-4,8-Dihydroxy-5,5,7,9,13-pen-
tamethyl-16-[2-(2-methyl-thiazol-4-yl)-vinyl]-oxacyclo-
hexadec-13-ene-2,6-dione,
(4S,7R,8S,9S,13Z,16S(E))-4,8-Dihydroxy-16-[2-(2-hy-
droxymethyl-thiazol-4-yl)-vinyl]-5,5,7,9,13-pentam-
ethyl-oxacyclohexadec-13-ene-2,6-dione,
(4S,7R,8S,9S,13Z,16S(E))-16-[2-(2-Aminomethyl-thiazol-
4-yl)-vinyl]-4,8-dihydroxy-5,5,7,9,13-pentamethyl-ox-
acyclohexadec-13-ene-2,6-dione,
(1S,3S(E),7S,10R,11S,12S,16R)-7,11-Dihydroxy-8,8,10,
12,16-pentamethyl-3-[2-(2-methyl-thiazol-4-yl)-vinyl]-4,
17-dioxa-bicyclo[14.1.0]heptadecane-5,9-dione,
(1S,3S(E),7S,10R,11S,12S,16R)-7,11-Dihydroxy-3-[2-(2-
hydroxymethyl-thiazol-4-yl)-vinyl]-8,8,10,12,16-pen-
tamethyl-4,17-dioxa-bicyclo[14.1.0]heptadecane-5,9-di-
one,
(1S,3S(E),7S,10R,11S,12S,16R)-3-[2-(2-Aminomethyl-
thiazol-4-yl)-vinyl]-7,11-dihydroxy-8,8,10,12,16-pen-
tamethyl-4,17-dioxa-bicyclo[14.1.0]heptadecane-5,9-di-
one,
(4S,7R,8S,9S,13Z,16S(E))-4,8-Dihydroxy-7-ethyl-5,5,9,
13-tetramethyl-16-[2-(2-methyl-thiazol-4-yl)-vinyl]-ox-
acyclohexadec-13-ene-2,6-dione,
(4S,7R,8S,9S,13Z,16S(E))-4,8-Dihydroxy-16-[2-(2-hy-
droxymethyl-thiazol-4-yl)-vinyl]-7-ethyl-5,5,9,13-tet-
ramethyl-oxacyclohexadec-13-ene-2,6-dione,
(4S,7R,8S,9S,13Z,16S(E))-16-[2-(2-Aminomethyl-thiazol-
4-yl)-vinyl]-4,8-dihydroxy-7-ethyl-5,5,9,13-tetramethyl-
oxacyclohexadec-13-ene-2,6-dione,
(1S,3S(E),7S,10R,11S,12S,16R)-7,11-Dihydroxy-10-ethyl-
8,8,12,16-tetramethyl-3-[2-(2-methyl-thiazol-4-yl)-vi-
nyl]-4,17-dioxa-bicyclo[14.1.0]heptadecane-5,9-dione,
(1S,3S(E),7S,10R,11S,12S,16R)-7,11-Dihydroxy-3-[2-(2-
hydroxymethyl-thiazol-4-yl)-vinyl]-10-ethyl-8,8,12,16-
tetramethyl-4,17-dioxa-bicyclo[14.1.0]heptadecane-5,9-
dione,
(1S,3S(E),7S,10R,11S,12S,16R)-3-[2-(2-Aminomethyl-
thiazol-4-yl)-vinyl]-7,11-dihydroxy-10-ethyl-8,8,12,16-
tetramethyl-4,17-dioxa-bicyclo[14.1.0]heptadecane-5,9-
dione,
(4S,7R,8S,9S,13Z,16S(E))-4,8-Dihydroxy-5,5,7,9,13-pen-
tamethyl-16-[2-(2-pyridyl)-vinyl]-oxacyclohexadec-13-
ene-2,6-dione,
(1S,3S(E),7S,10R,11S,12S,16R)-7,11-Dihydroxy-8,8,10,
12,16-pentamethyl-3-[2-(2-pyridyl)-vinyl]-4,17-dioxa-
bicyclo[14.1.0]heptadecane-5,9-dione,
(4S,7R,8S,9S,13Z,16S(E))-4,8-Dihydroxy-7-ethyl-5,5,9,
13-tetramethyl-16-[2-(2-pyridyl)-vinyl]-oxacyclohexa-
dec-13-ene-2,6-dione,
(1S,3S(E),7S,10R,11S,12S,16R)-7,11-Dihydroxy-10-ethyl-
8,8,12,16-tetramethyl-3-[2-(2-pyridyl)-vinyl]-4,17-di-
oxa-bicyclo [14.1.0]heptadecane-5,9-dione,
(4S,7R,8S,9S,13Z,16S)-4,8-Dihydroxy-5,5,7,9,13-pentam-
ethyl-16-(2-methyl-benzothiazol-5-yl)-oxacyclohexadec-
13-ene-2,6-dione,
(4S,7R,8S,9S,13Z,16S)-4,8-Dihydroxy-16-(2-hydroxym-
ethyl-benzothiazol-5-yl)-5,5,7,9,13-pentamethyl-oxacy-
clohexadec-13-ene-2,6-dione,
(4S,7R,8S,9S,13Z,16S)-16-(2-Aminomethyl-benzothiazol-
5-yl)-4,8-dihydroxy-5,5,7,9,13-pentamethyl-oxacyclo-
hexadec-13-ene-2,6-dione,
(1S,3S,7S,10R,11S,12S,16R)-7,11-Dihydroxy-8,8,10,12,
16-pentamethyl-3-(2-methyl-benzothiazol-5-yl)-4,17-di-
oxa-bicyclo[14.1.0]heptadecane-5,9-dione,
(1S,3S,7S,10R,11S,12S,16R)-7,11-Dihydroxy-3-(2-hy-
droxymethyl-benzothiazol-5-yl)-8,8,10,12,16-pentam-
ethyl-4,17-dioxa-bicyclo[14.1.0]heptadecane-5,9-dione,
(1S,3S,7S,10R,11S,12S,16R)-3-(2-Aminomethyl-ben-
zothiazol-5-yl)-7,11-dihydroxy-8,8,10,12,16-pentam-
ethyl-4,17-dioxa-bicyclo[14.1.0]heptadecane-5,9-dione,
(4S,7R,8S,9S,13Z,16S)-4,8-Dihydroxy-7-ethyl-5,5,9,13-
tetramethyl-16-(2-methyl-benzothiazol-5-yl)-oxacyclo-
hexadec-13-ene-2,6-dione,
(4S,7R,8S,9S,13Z,16S)-4,8-Dihydroxy-16-(2-hydroxym-
ethyl-benzothiazol-5-yl)-7-ethyl-5,5,9,13-tetramethyl-
oxacyclohexadec-13-ene-2,6-dione,
(4S,7R,8S,9S,13Z,16S)-16-(2-Aminomethyl-benzothiazol-
5-yl)-4,8-dihydroxy-7-ethyl-5,5,9,13-tetramethyl-oxacy-
clohexadec-13-ene-2,6-dione, (1S,3S,7S,10R,11S,12S,16R)-7,11-Dihydroxy-10-ethyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-ethyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzothiazol-5-yl)-7,11-dihydroxy-10-ethyl-8,8,12,16-tetramethyl-4,17-dioxa-bicyclo[14.1.0]heptadecane-5,9-dione, (4S,7R,8S,9S,13Z,16S)-4,8-Dihydroxy-7-propyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-propyl-5,5,9,13-tetramethyl-oxacyclohexadec-13-ene-2,6-dione, (4S,7R,8S,9S,13Z,16S)-16-(2-Aminomethyl-benzothiazol-5-yl)-4,8-dihydroxy-7-propyl-5,5,9,13-tetramethyl-oxacyclohexadec-13-ene-2,6-dione, (1S,3S,7S,10R,11S,12S,16R)-7,11-Dihydroxy-10-propyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-propyl-8,8,12,16-tetramethyl-4,17-dioxa-bicyclo[14.1.0]heptadecane-5,9-dione, (1S,3 S,7S,10R,11S,12S,16R)-3-(2-Aminomethyl-benzothiazol-5-yl)-7,11-dihydroxy-10-propyl-8,8,12,16-tetramethyl-4,17-dioxa-bicyclo[14.1.0]heptadecane-5,9-dione, (4S,7R,8S,9S,13Z,16S)-4,8-Dihydroxy-7-butyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-butyl-5,5,9,13-tetramethyl-oxacyclohexadec-13-ene-2,6-dione, (4S,7R,8S,9S,13Z,16S)-6-(2-Aminomethyl-benzothiazol-5-yl)-4,8-dihydroxy-7-butyl-5,5,9,13-tetramethyl-oxacyclohexadec-13-ene-2,6-dione, (1S,3S,7S,10R,11S,12S,16R)-7,11-Dihydroxy-10-butyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-butyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzothiazol-5-yl)-7,11-dihydroxy-10-butyl-8,8,12,16-tetramethyl-4,17-dioxa-bicyclo[14.1.0]heptadecane-5,9-dione, (4S,7R,8S,9S,13Z,16S)-4,8-Dihydroxy-7-allyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-allyl-5,5,9,13-tetramethyl-oxacyclohexadec-13-ene-2,6-dione, (4S,7R,8S,9S,13Z,16S)-16-(2-Aminomethyl-benzothiazol-5-yl)-4,8-dihydroxy-7-allyl-5,5,9,13-tetramethyl-oxacyclohexadec-13-ene-2,6-dione, (1S,3S,7S,10R,11S,12S,16R)-7,11-Dihydroxy-10-allyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-allyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzothiazol-5-yl)-7,11-dihydroxy-10-allyl-8,8,12,16-tetramethyl-4,17-dioxa-bicyclo[14.1.0]heptadecane-5,9-dione, (4S,7R,8S,9S,13Z,16S)-4,8-Dihydroxy-7-prop-2-inyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-prop-2-inyl-5,5,9,13-tetramethyl-oxacyclohexadec-13-ene-2,6-dione, (4S,7R,8S,9S,13Z,16S)-16-(2-Aminomethyl-benzothiazol-5-yl)-4,8-dihydroxy-7-prop-2-inyl-5,5,9,13-tetramethyl-oxacyclohexadec-13-ene-2,6-dione, (1S,3S,7S,10R,11S,12S,16R)-7,1-Dihydroxy-10-prop-2-inyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-prop-2-inyl-8,8,12,16-tetramethyl-4,17-dioxa-bicyclo [14.1.0]heptadecane-5,9-dione, (1S,3S,7S,10R,11S,12S,16R)-3-(2-Aminomethyl-benzothiazol-5-yl)-7,11-dihydroxy-10-prop-2-inyl-8,8,12,16-tetramethyl-4,17-dioxa-bicyclo[14.1.0]heptadecane-5,9-dione, (4S,7R,8S,9S,13Z,16S)-4,8-Dihydroxy-7-but-3-enyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-but-3-enyl-5,5,9,13-tetramethyl-oxacyclohexadec-13-ene-2,6-dione, (4S,7R,8S,9S,13Z,16S)-6-(2-Aminomethyl-benzothiazol-5-yl)-4,8-dihydroxy-7-but-3-enyl-5,5,9,13-tetramethyl-oxacyclohexadec-13-ene-2,6-dione, (1S,3S,7S,10R,11S,12S,16R)-7,11-Dihydroxy-10-but-3-enyl-8,8,12,16-tetramethyl-3-(2-methyl-benzothiazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzothiazol-5-yl)-10-but-3-enyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzothiazol-5-yl)-7,11-dihydroxy-10-but-3-enyl-8,8,12,16-tetramethyl-4,17-dioxa-bicyclo[14.1.0]heptadecane-5,9-dione, (4S,7R,8S,9S,13Z,16S)-4,8-Dihydroxy-7-but-3-inyl-5,5,9,13-tetramethyl-16-(2-methyl-benzothiazol-5-yl)-oxacyclohexadec-13-ene-2,6-dione, (4S,7R,8S,9S,13Z,16S)-4,8-Dihydroxy-16-(2-hydroxymethyl-benzothiazol-5-yl)-7-but-3-inyl-5,5,9,13-tetramethyl-oxacyclohexadec-13-ene-2,6-dione, (4S,7R,8S,9S,13Z,16S)-16-(2-Aminomethyl-benzothiazol-5-yl)-4,8-dihydroxy-7-but-3-inyl-5,5,9,13-tetramethyl-oxacyclohexadec-13-ene-2,6-dione, (1S,3S,7S,10R,11S,12S,16R)-7,11-Dihydroxy-10-but-3-inyl-8,8,12,16-tetramethyl-3-(2-methyl-benzothiazol-5-yl)-4,17-dioxa-bicyclo [14.1.0]heptadecane-5,9-dione, (1S,3S,7S,10R,11S,12S,16R)-7,11-Dihydroxy-3-(2-hydroxymethyl-benzothiazol-5-yl)-10-but-3-inyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzothiazol-5-yl)-7,11-dihydroxy-10-but-3-inyl-8,8,12,16-tetramethyl-4,17-dioxa-bicyclo[14.1.0]heptadecane-5,9-dione, (4S,7R,8S,9S,13Z,16S)-4,8-Dihydroxy-5,5,7,9,13-pentamethyl-16-(2-methylbenzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-5,5,7,9,13-pentamethyl-oxacyclohexadec-13-ene-2,6-dione, (4S,7R,8S,9S,13Z,16S)-16-(2-Aminomethyl-benzoxazol-5-yl)-4,8-dihydroxy-5,5,7,9,13-pentamethyl-oxacyclohexadec-13-ene-2,6-dione, (1S,3S,7S,10R,11S,12S,16R)-7,11-Dihydroxy-8,8,10,12,16-pentamethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-8,8,10,12,16-pentamethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-8,8,10,12,16-pentamethyl-4,17-dioxa-bicyclo[14.1.0]heptadecane-5,9-dione, (4S,7R,8S,9S,13Z,16S)-4,8-Dihydroxy-7-ethyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-ethyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-ethyl-5,5,9,13-tetramethyl-oxacyclohexadec-13-ene-2,6-dione, (1S,3S,7S,10R,11S,12S,16R)-7,11-Dihydroxy-10-ethyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-ethyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-ethyl-8,8,12,16-tetramethyl-4,17-dioxa-bicyclo[14.1.0]heptadecane-5,9-dione, (4S,7R,8S,9S,13Z,16S)-4,8-Dihydroxy-7-propyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-propyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-propyl-5,5,9,13-tetramethyl-oxacyclohexadec-13-ene-2,6-dione, (1S,3S,7S,10R,11S,12S,16R)-7,11-Dihydroxy-10-propyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-propyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-propyl-8,8,12,16-tetramethyl-4,17-dioxa-bicyclo[14.1.0]heptadecane-5,9-dione, (4S,7R,8S,9S,13Z,16S)-4,8-Dihydroxy-7-butyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-butyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-butyl-5,5,9,13-tetramethyl-oxacyclohexadec-13-ene-2,6-dione, (1S,3S,7S,10R,11S,12S,16R)-7,11-Dihydroxy-10-butyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-butyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-butyl-8,8,12,16-tetramethyl-4,17-dioxa-bicyclo[14.1.0]heptadecane-5,9-dione, (4S,7R,8S,9S,13Z,16S)-4,8-Dihydroxy-7-allyl-5,5,9,13-tetramethyl-16-(2-methylbenzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-allyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-allyl-5,5,9,13-tetramethyl-oxacyclohexadec-13-ene-2,6-dione, (1S,3S,7S,10R,11S,12S,16R)-7,11-Dihydroxy-10-allyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-allyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-allyl-8,8,12,16-tetramethyl-4,17-dioxa-bicyclo[14.1.0]heptadecane-5,9-dione, (4S,7R,8S,9S,13Z,16S)-4,8-Dihydroxy-7-prop-2-inyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-prop-2-inyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-prop-2-inyl-5,5,9,13-tetramethyl-oxacyclohexadec-13-ene-2,6-dione, (1S,3S,7S,10R,11 S,12S,16R)-7,11-Dihydroxy-10-prop-2-inyl-8,8,12,16-tetramethyl-3-(2-methyl-benzoxazol-5-yl)-4,17-dioxa-bicyclo [14.1.0]heptadecane-5,9-dione, (1S,3S,7S,10R,11S,12S,16R)-7,11-Dihydroxy-3-(2-hydroxymethyl-benzoxazol-5-yl)-10-prop-2-inyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-prop-2-inyl-8,8,12,16-tetramethyl-4,17-dioxa-bicyclo[14.1.0]heptadecane-5,9-dione, (4S,7R,8S,9S,13Z,16S)-4,8-Dihydroxy-7-but-3-enyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-but-3-enyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-but-3-enyl-5,5,9,13-tetramethyl-oxacyclohexadec-13-ene-2,6-dione, (1S,3S,7S,10R,11S,12S,16R)-7,11-Dihydroxy-10-but-3-enyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-but-3-enyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-but-3-enyl-8,8,12,16-tetramethyl-4,17-dioxa-bicyclo[14.1.0]heptadecane-5,9-dione, (4S,7R,8S,9S,13Z,16S)-4,8-Dihydroxy-7-but-3-inyl-5,5,9,13-tetramethyl-16-(2-methyl-benzoxazol-5-yl)-oxacyclohexadec-13-ene-2,6-dione, (4S,7R,8S,9S,13Z,16S)-4,8-Dihydroxy-16-(2-hydroxymethyl-benzoxazol-5-yl)-7-but-3-inyl-5,5,9,13-tetramethyl-oxacyclohexadec-13-ene-2,6-dione, (4S,7R,8S,9S,13Z,16S)-16-(2-Aminomethyl-benzoxazol-5-yl)-4,8-dihydroxy-7-but-3-inyl-5,5,9,13-tetramethyl-oxacyclohexadec-13-ene-2,6-dione, (1S,3S,7S,10R,11S,12S,16R)-7,11-Dihydroxy-10-but-3-inyl-8,8,12,16-tetramethyl-3-(2-methyl-benzoxazol-5-yl)-4,17-dioxa-bicyclo[14.1.0]heptadecane-5,9-dione, (1S,3S,7S,10R,11S,12S,16R)-7,11-Dihydroxy-3-(2-hydroxymethyl-benzoxazol-5-yl)-10-but-3-inyl-8,8,12,16-tetramethyl-4,17-dioxa-bicyclo[14.1.0]heptadecane-5,9-dione, (1S,3S,7S,10R,11S,12S,16R)-3-(2-Aminomethyl-benzoxazol-5-yl)-7,11-dihydroxy-10-but-3-inyl-8,8,12,16-tetramethyl-4,17-dioxa-bicyclo[14.1.0]heptadecane-5,9-dione.

In a compound of general formula (I) according to the invention that contains one of the above-mentioned elements, the hydrogen atoms in the above-mentioned elements are replaced in the positions indicated in formula (I) by radicals $L^1$-$L^3$, wherein radicals $L^1$-$L^3$ have the above-indicated meanings.

The invention also relates to linkers of general formula $III^1$

 $III^1$, in which $RG^1$ can be an O=C=N group or an S=C=N group, and o, V, q and $FG^1$ have the meanings that are already mentioned above, as well as linkers of general formula $III^2$

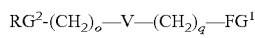 $III^2$, in which $RG^2$ can be a Hal-C(=T)-$CHR^{22}$ group or a Hal-C(=T)-$CHR^{22}$—$NR^{23}$—C(=T) group or an $R^{26}$—C(=O)—O—C(=T)-$CHR^{22}$ group or an $R^{26}$—C(=O)—O—C(=T)-$CHR^{22}$—$NR^{23}$—C(=T) group; $R^{26}$ can be $C_1$-$C_{10}$ alkyl, aryl, or aralkyl, and o, V, q, T and $FG^1$ have the meanings that are already mentioned above, as well as linkers of general formula $III^3$

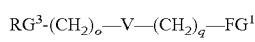 $III^3$, in which $RG^3$ can be an OH group or an $NHR^{24a}$ group or a COOH group, and o, V, q and $FG^1$ have the meanings that are already mentioned above;

but with the proviso that the compound 1-(4-amino-phenyl)-pyrrole-2,5-dione is not included.

The invention also relates to linkers of general formula ($IV^1$):

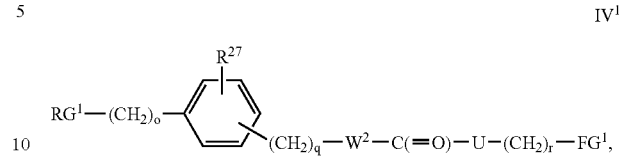 $IV^1$ in which $RG^1$ is an O=C=N group or an S=C=N group, and o, q, r, $W^2$, $R^{27}$, U and $FG^1$ have the meanings that are mentioned in claim 1;

or linkers of general formula ($IV^2$):

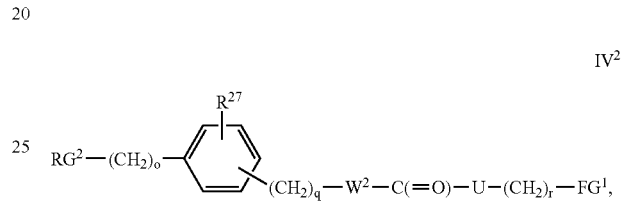 $IV^2$ in which $RG^2$ is a Hal-C(=T)-$CHR^{22}$ group or a Hal-C(=T)-$CHR^{22}$—$NR^{23}$—C(=T) group or an $R^{26}$—C(=O)—O—C(=T)-$CHR^{22}$ group or an $R^{26}$—C(=O)—O—C(=T)-$CHR^{22}$—$NR^{23}$—C(=T) group, wherein $R^{26}$ is $C_1$-$C_{10}$ alkyl, aryl, or aralkyl, and $R^{22}$, $R^{23}$, T, o, q, r, $W^2$, $R^{27}$, U and $FG^1$ have the meanings that are mentioned in claim 1;

or linkers of general formula ($IV^3$):

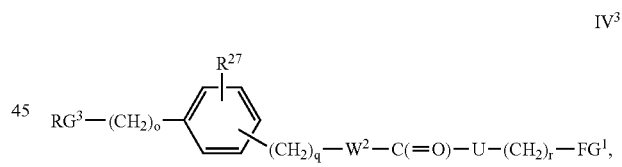 $IV^3$ in which $RG^3$ is an OH group or an $NHR^{24a}$ group or a COOH group, and $R^{24a}$, o, q, r, $W^2$, $R^{27}$, U and $FG^1$ have the meanings that are mentioned in claim 1.

According to the invention, linkers of general formulas $III^1$, $III^2$ or $III^3$ are preferred, wherein V represents a bond or an aryl radical, o is equal to zero, and T is an oxygen atom.

In addition, linkers of general formulas $III^1$, $III^2$ or $III^3$ according to the invention are preferred, in which V represents a bond or an aryl radical or a group

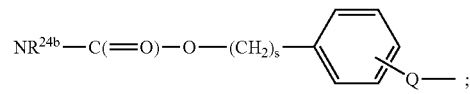 ;

Q represents a bond or a group

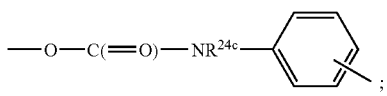

and o is 0 to 4. Especially preferred from the above are those linkers in which V represents a bond or a group

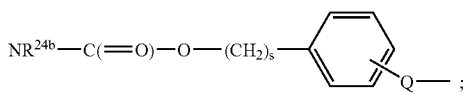

Q represents a bond or a group

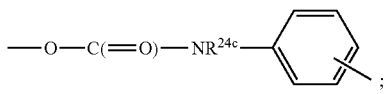

o is equal to 0, 2 or 3; s is equal to 1; and T is an oxygen atom.

In addition, preferred according to the invention are linkers of general formulas $IV^1$, $IV^2$ or $IV^3$, in which o is zero to four and q is zero to three. Especially preferred from the above are those linkers in which o is 0, 2 or 3; $W^1$ is an oxygen atom; q is equal to 0; $R^{22}$ is hydrogen, $C_1$-$C_3$ alkyl or aralkyl; $R^{23}$ is hydrogen or $C_1$-$C_3$ alkyl; $R^{24a}$ is hydrogen or $C_1$-$C_3$ alkyl; $R^{27}$ is fluorine, chlorine, CN, $NO_2$, $CO_2R^{28}$ or $OR^{28}$; $R^{28}$ is hydrogen or $C_1$-$C_5$ alkyl; and U is oxygen, $CHR^{22}$ or $CHR^{22}$—$NR^{23}$—$C(=O)$.

Additionally, the invention relates to methods to react a linker of general formula $III^1$ or $IV^1$ with a compound of general formula I, in which the condition that at least one group $L^1$, $L^2$ or $L^4$ represent a linker need not be met, and in which $L^1$ and/or $L^2$ and/or $L^4$ have the meaning of a hydrogen atom, and free hydroxyl groups and/or amino groups that are not required for the reaction optionally are protected, to react a linker of general formula $III^2$ or $IV^2$ with a compound of general formula I, in which the condition that at least one group $L^1$, $L^2$ or $L^4$ represent a linker need not be met, and $L^1$ and/or $L^2$ and/or $L^4$ have the meaning of a hydrogen atom, and free hydroxyl groups and/or amino groups that are not required for the reaction are optionally protected, or to react a linker of general formula $III^3$ or $IV^3$ with a compound of general formula I, in which the condition that at least one group $L^1$, $L^2$ or $L^4$ represent a linker need not be met, and $L^1$ and/or $L^2$ and/or $L^4$ have the meaning of a $C(=O)$Hal group or a $C(=S)$Hal group, and free hydroxyl groups and/or amino groups that are not required for the reaction are optionally protected.

The invention also relates to the use of a compound of general formula I, wherein the substituents have the above-mentioned meanings, but the condition that at least one substituent $L^1$, $L^2$ or $L^4$ represents a linker of general formula III or IV need not be met, and at least one substituent $L^1$, $L^2$ or $L^4$ represents hydrogen, a group $C(=O)$Cl, or a group $C(S)$Cl, in a method as described above.

The invention also relates to the use of a compound of general formula I, wherein the substituents have the above-mentioned meanings, but the condition that at least one substituent $L^1$, $L^2$ or $L^4$ represent a linker of general formula III or IV need not be met, and at least one substituent $L^1$, $L^2$ or $L^4$ represents hydrogen, a group $C(=O)$Cl, or a group $C(S)$Cl, for the production of an effector recognition unit conjugate as described above.

The invention also relates to the use of a linker of general formula $III^1$, $III^2$, $III^3$, $IV^1$, $IV^2$ or $IV^3$ for the production of an effector conjugate, as described above.

The invention also relates to the use of a linker of general formula $III^1$, $III^2$, $III^3$, $IV^1$, $IV^2$ or $IV^3$ for the production of an effector recognition unit conjugate as described above.

The invention also relates to the use of a recognition unit, as described above, in a process according to the invention for the production of an effector recognition unit conjugate, as described above.

The invention also relates to the effector recognition unit conjugates according to the invention for use as a medicament or for the production of a medicament or a pharmaceutical composition.

The invention relates finally to the use of the effector recognition unit conjugates according to the invention for the production of medicaments for the treatment of diseases that are associated with proliferative processes, such as tumors, inflammatory and/or neurodegenerative diseases, multiple sclerosis, Alzheimer's disease, or for the treatment of angiogenesis-associated diseases, such as tumor growth, rheumatoid arthritis or diseases of the ocular fundus.

EXAMPLES OF THE SYNTHESIS OF LINKERS
(L)

Example L1

(S)2-[(3-Methyltrisulfanyl-propionyl)-methyl-amino]-propanoic acid

Example L1a (S)2-[(3-Acetylsulfanyl-propionyl)-methyl-amino]-propanoic acid ethyl ester The solution of 15 g (89.5 mmol) of N-methylalanine ethyl ester-hydrochloride in 850 ml of anhydrous tetrahydrofuran is mixed at 23° C. with 4.1 g of an approximately 60% sodium hydride dispersion and, after 3 hours, with 23.5 g of 3-acetylsulfanyl-propanoic acid chloride. It is allowed to react for two days, mixed with saturated sodium bicarbonate solution, and extracted several times with ethyl acetate. The combined organic extracts are washed with saturated sodium chloride solution, dried over sodium sulfate, and the residue that is obtained after filtration and removal of the solvent is purified by chromatography on fine silica gel. 17.6 g (67.3 mmol, 75%) of the title compound is isolated as a colorless oil.

Example L1b (S)2-[(3-Mercapto-propionyl)-methyl-amino]-propanoic acid

The solution of 17.6 g (67.3 mmol) of the compound prepared according to Example L1a in 150 ml of methanol is mixed at 23° C. with 44 ml of a 5M sodium hydroxide solution, and it is stirred for 5 hours. By adding 4N hydrochloric acid, a pH of 2 is set, and it is extracted with dichloromethane. The combined organic extracts are washed with saturated sodium chloride solution and dried over sodium sulfate. The residue that is obtained after filtration and removal of the solvent (13.0 g, maximum 67.3 mmol) is further reacted without purification.

Example L1c (S)2-[(3-Mercapto-propionyl)-methyl-amino]-propanoic acid methyl ester The solution of 4.53 g (maximum 23.7 mol) of the crude product, prepared according to Example L1b, in 135 ml of diethyl ether is esterified at 0° C. with an ethereal solution of diazomethane. After removal of the solvent, 4.59 g (22.4 mmol, 94%) of the title compound is isolated as a pale yellow oil, which is further reacted without purification.

Example L1d (S)2-[(3-Methyltrisulfanyl-propionyl)-methyl-amino]-propanoic acid methyl ester The solution of 14 g (68.2 mmol) of the compound, prepared according to Example L1c, in 180 ml of trichloromethane is added to the solution of 21 g of 2-methyldisulfanyl-isoindole-1,3-dione in 420 ml of trichloromethane, and it is stirred for 16 hours at 23° C. It is concentrated by evaporation, dissolved in dichloromethane, and stirred for 0.5 hour. Solid is filtered off, the filtrate is concentrated by evaporation, and the residue is purified by chromatography on fine silica gel. 16.2 g (57.2 mmol, 84%) of the title compound is isolated as a colorless oil.

Example L1

(S)2-[(3-Methyltrisulfanyl-propionyl)-methyl-amino]-propanoic acid

The solution of 10 g (35.3 mmol) of the compound, prepared according to Example L1d, in 20 ml of ethanol is mixed with 11 of phosphate puffer with a pH of 7, pig liver esterase, and it is incubated at 27° C. for 46 hours. By adding a 4N hydrochloric acid, the pH is adjusted to 1, it is extracted with dichloromethane, dried over sodium sulfate, and after filtration and removal of the solvent, 8.3 g (30.8 mmol, 87%) of the title compound is isolated as a colorless oil, which is reacted without further purification.

$^1$H-NMR (CDCl$_3$): δ=1.43+1.51 (3H), 2.55+2.63 (3H), 2.87 (2H), 2.88+3.00 (3H), 3.08-3.26 (2H), 4.63+5.19 (1H), 7.90 (1H) ppm.

Example L2

[(3-Methyltrisulfanyl-propionyl)-methyl-amino]-acetic acid

Example L2a

2-[(3-Acetylsulfanyl-propionyl)-methyl-amino]-acetic acid ethyl ester 7.13 g (46.4 mmol) of N-methylglycine ethyl ester-hydrochloride is reacted analogously to Example L1a, and 6.9 g (27.9 mmol, 60%) of the title compound is isolated as a colorless oil.

Example L2b

[(3-Mercapto-propionyl)-methyl-amino]-acetic acid 7.6 g (30.7 mmol) of the compound that is prepared according to Example L2a is reacted analogously to Example L1b, and 4.92 g (27.8 mmol, 90%) of the title compound is isolated as a colorless oil.

Example L2c

[(3-Mercapto-propionyl)-methyl-amino]-acetic acid methyl ester 4.92 g (27.8 mmol) of the compound that is prepared according to Example L2b is reacted analogously to Example L1c, and 5.01 g (26.2 mmol, 94%) of the title compound is isolated as a colorless oil.

Example L2d

[(3-Methyltrisulfanyl-propionyl)-methyl-amino]-acetic acid methyl ester 2.00 g (10.5 mmol) of the compound that is prepared according to Example L2c is reacted analogously to Example L1d, and 2.33 g (8.65 mmol, 82%) of the title compound is isolated as a colorless oil.

Example L2

[(3-Methyltrisulfanyl-propionyl)-methyl-amino]-acetic acid 2.00 g (7.83 mmol) of the compound that is prepared according to Example L2d is reacted analogously to Example L1, and 0.64 g (2.51 mmol, 32%) of the title compound is isolated as a colorless oil.

$^1$H-NMR (CDCl$_3$): δ=2.41+2.56 (3H), 2.61-3.27 (7H), 3.98 (2H), 4.38 (1H) ppm.

Example L3

(S)2-[(3-Methyltrisulfanyl-propionyl)-methyl-amino]-3-phenyl-propionic acid

Example L3a (S)2-[(3-Acetylsulfanyl-propionyl)-methyl-amino]-3-phenyl-propanoic acid ethyl ester 7.73 g (31.7 mmol) of N-methylphenylalanine ethyl ester-hydrochloride is reacted analogously to Example L1a, and 2.3 g (6.82 mmol, 22%) of the title compound is isolated as a colorless oil.

Example L3b (S)2-[(3-Mercapto-propionyl)-methyl-amino]-3-phenyl-propanoic acid 1.09 g (3.23 mmol) of the compound that is prepared according to Example L3a is reacted analogously to Example L1b, and 0.744 g (2.78 mmol, 86%) of the title compound is isolated as a colorless oil.

Example L3c (S)2-[(3-Mercapto-propionyl)-methyl-amino]-3-phenyl-propanoic acid methyl ester 0.74 g (2.77 mmol) of the compound that is prepared according to Example L3b is reacted analogously to Example L1c, and 0.77 g (2.74 mmol, 99%) of the title compound is isolated as a colorless oil.

Example L3d (S)2-[(3-Methyltrisulfanyl-propionyl)-methyl-amino]-3-phenyl-propanoic acid methyl ester 0.77 g (2.74 mmol) of the compound that is prepared according to Example L3c is reacted analogously to Example L1d, and 0.72 g (2.00 mmol, 73%) of the title compound is isolated as a colorless oil.

Example L3

(S)2-[(3-Methyltrisulfanyl-propionyl)-methyl-amino]-3-phenyl-propanoic acid 0.72 g (2.00 mmol) of the compound that is prepared according to Example L3d is reacted analogously to Example L1, and 0.49 g (1.42 mmol, 71%) of the title compound is isolated as a colorless oil.

Example L4

4-(2,5-Dioxo-2,5-dihydro-pyrrol-1-yl)-butanoic acid 20.0 g (193.9 mmol) of 4-aminobutyric acid is mixed with 19 g of maleic acid anhydride, 290 ml of acetic acid, and it is heated for 4 hours in an oil bath at 130° C. It is azeotropically concentrated by evaporation with repeated addition of toluene, the residue is dissolved in dichloromethane and purified by chromatography on fine silica gel. 17.1 g (93.4 mmol, 48%) of the title compound is isolated as a crystalline solid.
$^1$H-NMR (CDCl$_3$): δ=1.93 (2H), 2.38 (2H), 3.60 (2H), 6.71 (2H) ppm.

Example L4a 1-(3-Isocyanato-propyl)-pyrrole-2,5-dione 5.0 g (27.3 mmol) of the compound that is prepared according to Example L4 is dissolved in 90 ml of tetrahydrofuran, mixed with 8 ml of triethylamine and 6.17 ml of phosphoric acid diphenylester azide, and it is stirred for 1.5 hours at 23° C. Then, it is mixed with 110 ml of toluene, the tetrahydrofuran is distilled off, and it is heated for 2 hours to 70° C. The crude product is purified by chromatography on fine silica gel. 1.77 g (9.82 mmol, 36%) of the title compound is isolated.

Example L5

6-(2,5-Dioxo-2,5-dihydro-pyrrol-1-yl)-hexanoic acid 100 g (762 mmol) of 6-aminocaproic acid is reacted analogously to Example L5, and 93.8 g (444 mmol, 58%) of the title compound is isolated as a crystalline solid.
$^1$H-NMR (CDCl$_3$): δ=1.34 (2H), 1.55-1.70 (4H), 2.34 (2H), 3.51 (2H), 6.69 (2H) ppm.

Example L5a 1-(5-Isocyanato-pentyl)-pyrrole-2,5-dione 10.0 g (47.3 mmol) of the compound that is prepared according to Example L5 is reacted analogously to Example L4a, and 3.19 g (15.3 mmol, 32%) of the title compound is isolated as a colorless oil.

Example L6

11-(2,5-Dioxo-2,5-dihydro-pyrrol-1-yl)-undecanoic acid 10 g (49.7 mmol) of 11-aminoundecanoic acid is reacted analogously to Example L5, and 6.29 g (22.4 mmol, 45%) of the title compound is isolated as a crystalline solid.
$^1$H-NMR (CDCl$_3$): δ=1.19-1.36 (12H), 1.51-1.67 (4H), 2.34 (2H), 3.49 (2H), 6.68 (2H) ppm.

Example L6a 1-(10-Isocyanato-decyl)-pyrrole-2,5-dione 5.28 g (18.8 mmol) of the compound that is prepared according to Example L6 is reacted analogously to Example L4a, and 3.37 g (12.1 mmol, 64%) of the title compound is isolated as a colorless oil.

Example L7

1-(4-Amino-phenyl)-pyrrole-2,5-dione

The solution of 21.6 g (200 mmol) of 1,4-phenylenediamine in 200 ml of tetrahydrofuran is mixed over 1.5 hours with the solution of 19.6 g of maleic acid anhydride, and it is stirred for 22 hours at 23° C. It is filtered, rewashed with tetrahydrofuran, and the filtrate is dried. 37.1 g (197 mmol, 98%) of the title compound is isolated as a crystalline solid.
$^1$H-NMR (d6-DMSO): δ=6.28 (1H), 6.48 (1H), 6.53 (2H), 7.30 (2H), 7.50-9.00 (2H) ppm.

Example L8

1-(4-Hydroxy-phenyl)-pyrrole-2,5-dione

The suspension that consists of 5.0 g (45.8 mmol) of 4-aminophenol, 4.49 g of maleic acid anhydride and 40 ml of acetic acid is refluxed for 3 hours. It is concentrated by evaporation, residual acetic acid is removed azeotropically by repeated distillation with acetic acid, and the residue is purified by chromatography on fine silica gel. 2.83 g (15.0 mmol, 33%) of the title compound is isolated.
$^1$H-NMR (d6-DMSO): δ=6.83 (2H), 7.09 (2H), 7.13 (2H), 9.71 (1H) ppm.

Example L9

4-(2,5-Dioxo-2,5-dihydro-pyrrol-1-yl)-butanoic acid 4-hydroxymethyl-2-nitro-phenyl ester The solution of 5.0 g (29.6 mmol) of 4-hydroxymethyl-2-nitro-phenol in 250 ml of dichloromethane is mixed with 6.1 g of N,N'-dicyclohexylcarbodiimide and 2.4 ml of pyridine, and the solution of 5.5 g of the compound, prepared according to Example L4, in 250 ml of dichloromethane, is added dropwise within 15 minutes. It is stirred for one more hour at 23° C., filtered, the filtrate is concentrated by evaporation and purified by chromatography on fine silica gel. 1.73 g (5.2 mmol, 18%) of the title compound is isolated.

$^1$H-NMR (CDCl$_3$): δ=2.07 (3H), 2.67 (2H), 3.67 (2H), 4.79 (2H), 6.72 (2H), 7.28 (1H), 7.66 (1H), 8.10 (1H) ppm.

Example L10

6-(2,5-Dioxo-2,5-dihydro-pyrrol-1-yl)-hexanoic acid 4-hydroxymethyl-2-nitro-phenyl ester Analogously to Example L9, 5.0 g (29.6 mmol) of 4-hydroxymethyl-2-nitro-phenol is reacted with 6.34 g of the compound that is prepared according to Example L5, and after working-up and purification, 3.78 g (10.4 mmol, 35%) of the title compound is isolated.

$^1$H-NMR (CDCl$_3$): δ=1.42 (2H), 1.66 (2H), 1.88 (2H), 2.64 (2H), 3.55 (2H), 4.78 (2H), 6.69 (2H), 7.21 (1H), 7.64 (1H), 8.09 (1H) ppm.

Example L11

11-(2,5-Dioxo-2,5-dihydro-pyrrol-1-yl)-undecanoic acid 4-hydroxymethyl-2-nitro-phenyl ester Analogously to Example L9, 5.0 g (29.6 mmol) of 4-hydroxymethyl-2-nitro-phenol is reacted with 8.44 g of the compound that is prepared according to Example L6, and after working-up and purification, 3.78 g (10.4 mmol, 35%) of the title compound is isolated.

$^1$H-NMR (CDCl$_3$): δ=1.21-1.63 (14H), 1.76 (2H), 1.99 (1H), 2.63 (2H), 3.51 (2H), 4.78 (2H), 6.68 (2H), 7.21 (1H), 7.65 (1H), 8.10 (1H) ppm.

Example L12

4-(2,5-Dioxo-2,5-dihydro-pyrrol-1-yl)-butanoic acid 4-hydroxymethyl-phenyl ester 5.5 g (23.1 mmol) 4-tert-Butyldimethylsilanyloxymethyl-phenol, 20 mg N,N-Dimethyl-4-aminopyridine and 4.23 g (23.1 mmol) of the compound prepared according to Example L4 are dissolved in 92 ml of dichloromethane and cooled to 0° C. 4.77 g (23.1 mmol) N,N'-Dicyclohexylcarbodiimide in 24 ml dichloromethane are added dropwise to the cooled solution over a period of 15 min. The mixture is stirred for 16 hours at 23° C., filtered, the filtrate is concentrated and purified by chromatography on fine silica gel. 7.18 g (17.8 mmol, 77%) 4-(2,5-Dioxo-2,5-dihydro-pyrrol-1-yl)-butanoic acid-4-tert-butyldimethylsilanyloxymethyl-phenyl ester are isolated. 1.42 g thereof are dissolved in 63 ml THF and 7 ml water, and 0.67 g (3.52 mmol) p-toluenesulfonic acid are added at room temperature. After 16 hours, a saturated sodium bicarbonate solution is added and the mixture is extracted several times with ethyl acetate. The combined organic layers are washed with a saturated solution of sodium chloride, dried over sodium sulfate and purified by chromatography on fine silica gel. 0.43 g (1.5 mmol, 42%) of the title compound are isolated.

$^1$H-NMR (CDCl$_3$): δ=1.71 (1H), 2.04 (2H), 2.58 (2H), 3.67 (2H), 4.68 (2H), 6.71 (2H), 7.09 (2H), 7.38 (2H) ppm.

Example L13

6-(2,5-Dioxo-2,5-dihydro-pyrrol-1-yl)-hexanoic acid 4-hydroxymethyl-phenyl ester Analogously to Example L12, 4.02 g (13.8 mmol) 4-tert-butyldimethylsilanyloxymethyl-phenol are reacted with 3.56 g (13.8 mmol) of the compound prepared according to Example L5. After working-up, purification and analogous treatment with p-toluenesulfonic acid, 3.19 g (10.1 mmol, 60%) of the title compound are isolated.

$^1$H-NMR (CDCl$_3$): δ=1.42 (2H), 1.59-1.83 (5H), 2.55 (2H), 3.55 (2H), 4.68 (2H), 6.69 (2H), 7.06 (2H), 7.38 (2H) ppm.

Example L14

11-(2,5-Dioxo-2,5-dihydro-pyrrol-1-yl)-undecanoic acid 4-hydroxymethyl-phenyl ester Analogously to Example L12, 5.41 g (22.7 mmol) 4-tert-butyldimethylsilanyloxymethyl-phenol are reacted with 6.39 g (22.7 mmol) of the compound prepared according to Example L6. After working-up, purification and analogous treatment with p-toluenesulfonic acid, 5.91 g (15.3 mmol, 67%) of the title compound are isolated.

$^1$H-NMR (CDCl$_3$): δ=1.24-1.43 (12H), 1.57 (3H), 1.74 (2H), 2.55 (2H), 3.50 (2H), 4.69 (2H), 6.68 (2H), 7.06 (2H), 7.38 (2H) ppm.

Example L15

4-(2,5-Dioxo-2,5-dihydro-pyrrol-1-yl)-butanoic acid 4-hydroxymethyl-2-chloro-phenyl ester Analogously to Example L9, 5.0 g (29.6 mmol) of 4-hydroxymethyl-2-chloro-phenol are reacted with 5.42 g of the compound prepared according to Example L4. After working-up and purification, 8.49 g (26.2 mmol, 89%) of the title compound are isolated.

$^1$H-NMR (CDCl$_3$): δ=2.07 (3H), 2.64 (2H), 3.67 (2H), 4.67 (2H), 6.72 (2H), 7.14 (1H), 7.27 (1H), 7.46 (1H) ppm.

Example L16

6-(2,5-Dioxo-2,5-dihydro-pyrrol-1-yl)-hexanoic acid 4-hydroxymethyl-2-chloro-phenyl ester Analogously to Example L9, 5.0 g (29.6 mmol) of 4-hydroxymethyl-2-chloro-phenol are reacted with 6.24 g of the compound prepared according to Example L5. After working-up and purification, 5.11 g (14.5 mmol, 49%) of the title compound are isolated.

$^1$H-NMR (CDCl$_3$): δ=1.43 (2H), 1.66 (2H), 1.81 (3H), 2.61 (2H), 3.55 (2H), 4.67 (2H), 6.69 (2H), 7.10 (1H), 7.26 (1H), 7.46 (1H) ppm.

Example L17

11-(2,5-Dioxo-2,5-dihydro-pyrrol-1-yl)-undecanoic acid 4-hydroxymethyl-2-chloro-phenyl ester Analogously to Example L9, 4.61 g (29 mmol) 4-hydroxymethyl-2-chloro-phenol are reacted with 8.17 g of the compound prepared according to Example L6. After working-up and purification, 4.61 g (10.9 mmol, 38%) of the title compound are isolated.

$^1$H-NMR (CDCl$_3$): δ=1.18-1.84 (17H), 2.61 (2H), 3.51 (2H), 4.67 (2H), 6.68 (2H), 7.10 (1H), 7.27 (1H), 7.46 (1H) ppm.

Example L18

1-(6-Hydroxy-hexyl)-pyrrol-2,5-dione 26 ml of a 1.0M solution of borane-tetrahydrofurane-complex in tetrahydrofurane is added to a solution of 5.0 g (23.7 mmol) of the acid prepared according to Example L5 in 50 ml of anhydrous tetrahydrofurane and the mixture is stirred for 3 hours at 23° C. The mixture is poured into a saturated solution of sodium bicarbonate, extracted several times with ethyl acetate, and the combined organic extracts are dried over sodium sulfate. After filtration and removal of the solvent, the residue is purified by chromatography. 2.53 g (12.8 mmol, 54%) of the title compound are isolated.

$^1$H-NMR (CDCl$_3$): δ=1.24-1.65 (9H), 3.52 (2H), 3.63 (2H), 6.68 (2H) ppm.

EXAMPLES OF THE SYNTHESIS OF EFFECTOR-LINKER CONJUGATES (EL)

Example EL1

(4S,7R,8S,9S,13Z,16S)-[3-(2,5-Dioxo-2,5-dihydro-pyrrol-1-yl)-propyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester

Example EL1a

(4S,7R,8S,9S,13Z,16S)-7-Allyl-8-(tert-butyl-dimethyl-silanyloxy)-4-hydroxy-5,5,9,13-tetramethyl-16-(2-methyl-benzothiazol-5-yl)-oxacyclohexadec-13-ene-2,6-dione The solution of 6.0 g (7.93 mmol) of (4S,7R,8S,9S,13Z,16S)-7-allyl-4,8-bis(tert-butyl-dimethyl-silanyloxy)-5,5,9,13-tetramethyl-16-(2-methyl-benzothiazol-5-yl)-oxacyclohexadec-13-ene-2,6-dione, which was produced analogously to the process that is described in WO 00/66589, in 186 ml of anhydrous dichloromethane is mixed at 0° C. with 26.4 ml of a 20% solution of trifluoroacetic acid in dichloromethane, and it is stirred for 6 hours at 0° C. It is poured into saturated sodium bicarbonate solution, extracted with dichloromethane, the combined organic extracts are washed with water and dried over magnesium sulfate. The residue that is obtained after filtration and removal of the solvent is purified by chromatography on fine silica gel. 3.32 g (5.17 mmol, 65%) of the title compound is isolated as a colorless solid.

$^1$H-NMR (CDCl$_3$): δ=0.09 (3H), 0.12 (3H), 0.93 (9H), 1.00 (3H), 1.06 (3H), 1.22 (3H), 1.70 (3H), 1.03-1.77 (5H), 1.95 (1H), 2.31-2.56 (6H), 2.83 (3H), 2.87 (1H), 3.00 (1H), 3.30 (1H), 3.90 (1H), 4.09 (1H), 4.94-5.03 (2H), 5.20 (1H), 5.77 (1H), 5.88 (1H), 7.34 (1H), 7.78 (1H), 7.95 (1H) ppm.

Example EL1b

(4S,7R,8S,9S,13Z,16S)-3-(2,5-Dioxo-2,5-dihydro-pyrrol-1-yl)-propyl]-carbamic acid-7-allyl-8-tert-butyl-dimethylsilyloxy-5,5,9,13-tetramethyl-16-(2-methyl-benzothiazol-5-yl)-2,6-dioxo-oxacyclohexadec-13-en-4-yl ester 50 mg (78 µmol) of the compound that is prepared according to Example EL1a is dissolved in a mixture of 1.5 ml of trichloromethane and 1.5 ml of dimethylformamide, mixed with 144 mg of the linker that is prepared according to Example L4a, 79 mg of copper(I) chloride, and it is heated for 18 hours to 70° C. The crude mixture is purified by chromatography on thin-layer plates, and 51 mg (62 µmol, 80%) of the title compound is isolated as a colorless oil.

Example EL1

(4S,7R,8S,9S,13Z,16S)-[3-(2,5-Dioxo-2,5-dihydro-pyrrol-1-yl)-propyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester The solution of 41 mg (50 µmol) of the compound, prepared according to Example 1b, in a mixture of 0.8 ml of tetrahydrofuran and 0.8 ml of acetonitrile is mixed with 310 µl of hexafluorosilicic acid, 310 µl of hydrogen fluoride-pyridine complex, and it is stirred for 23 hours at 23° C. It is poured into a 5% sodium hydroxide solution, extracted with ethyl acetate, the combined organic extracts are washed with a saturated sodium chloride solution and dried over sodium sulfate. The residue that is obtained after filtration and removal of the solvent is purified by chromatography on thin-layer plates, and 26 mg (36.7 µmol, 73%) of the title compound is isolated as a colorless foam.

$^1$H-NMR (CDCl$_3$): δ=0.99 (3H), 1.14 (3H), 1.17 (3H), 1.20-1.51 (3H), 1.54-1.87 (6H), 1.70 (3H), 2.22 (1H), 2.28-3.02 (9H), 2.83 (3H), 3.31 (1H), 3.45 (1H), 3.68 (1H), 4.44+4.83 (1H), 4.99 (1H), 5.03 (1H), 5.15 (1H), 5.61 (1H), 5.72 (1H), 5.91 (1H), 6.68 (2H), 7.36 (1H), 7.78 (1H), 7.90 (1H) ppm.

Example EL2

(1S,3S,7S,10R,11S,12S,16R)-[3-(2,5-Dioxo-2,5-dihydro-pyrrol-1-yl)-propyl]-carbamic acid-10-allyl-11-hydroxy-8,8,12,16-tetramethyl-3-(2-methyl-benzothiazol-5-yl)-5,9-dioxo-4,17-dioxabicyclo[14.1.0] heptadec-7-yl ester (A) and

(1R,3S,7S,10R,11S,12S,16S)-[3-(2,5-Dioxo-2,5-dihydro-pyrrol-1-yl)-propyl]-carbamic acid-10-allyl-11-hydroxy-8,8,12,16-tetramethyl-3-(2-methyl-benzothiazol-5-yl)-5,9-dioxo-4,17-dioxabicyclo[14.1.0] heptadec-7-yl ester (B)

The solution of 44 mg (62.2 µmol) of the compound, prepared according to Example 1, in 2.0 ml of dichloromethane is cooled to −50° C. and mixed in portions over a period of 1.5 hours with a total of 1.7 ml of an approximately 0.1 M solution of dimethyl dioxiran in acetone. It is poured into a saturated sodium thiosulfate solution, extracted with dichloromethane, and the combined organic extracts are dried over sodium sulfate. The residue that is obtained after filtration and removal of the solvent is purified by chromatography on thin-layer plates, and 22.7 mg (31.4 µmol, 50%) of title compound A as well as 7.6 mg (10.5 µmol, 17%) of title compound B are isolated in each case as a colorless foam.

$^1$H-NMR (CDCl$_3$) of A: δ=1.01 (3H), 1.14 (3H), 1.16 (3H), 1.20-1.94 (8H), 1.32 (3H), 2.11-2.74 (9H), 2.82 (1H), 2.84 (3H), 3.30 (2H), 3.48 (2H), 3.68 (1H), 4.36+4.93 (1H), 4.99 (1H), 5.04 (1H), 5.54 (1H), 5.69 (1H), 6.05 (1H), 6.68 (2H), 7.32 (1H), 7.80 (1H), 7.88 (1H) ppm.

$^1$H-NMR (CDCl$_3$) of B: δ=1.02 (6H), 1.26 (3H), 1.33 (1H), 1.23-2.27 (12H), 2.54-2.78 (4H), 2.82 (3H), 2.91 (1H), 3.13 (1H), 3.40 (2H), 3.66 (1H), 4.11 (1H), 4.84 (1H), 4.95 (1H), 5.01 (1H), 5.70 (1H), 5.81+5.93 (1H), 6.04+6.13 (1H), 6.69 (2H), 7.35 (1H), 7.75 (1H), 7.90+7.99 (1H) ppm.

Example EL3

(4S,7R,8S,9S,13Z,16S)-[5-(2,5-Dioxo-2,5-dihydro-pyrrol-1-yl)-pentyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester Example EL3a (4S,7R,8S,9S,13Z,16S)-[5-(2,5-Dioxo-2,5-dihydro-pyrrol-1-yl)-pentyl]-carbamic acid-7-allyl-8-tert-butyl-dimethylsilyloxy-5,5,9,13-tetramethyl-16-(2-methyl-benzothiazol-5-yl)-2,6-dioxo-oxacyclohexadec-13-en-4-yl ester 50 mg (78 µmol) of the compound that is prepared according to Example EL1a is reacted analogously to Example EL1b with the linker that is produced according to Example L5a, and after purification, 39 mg (45.9 µmol, 59%) of the title compound is isolated as a colorless oil.

Example EL3

(4S,7R,8S,9S,13Z,16S)-[5-(2,5-Dioxo-2,5-dihydro-pyrrol-1-yl)-pentyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester 84 mg (98.8 µmol) of the compound that is prepared according to Example EL3a is reacted analogously to Example EL1, and after purification, 43 mg (58.4 µmol, 59%) of the title compound is isolated as a colorless foam.

$^1$H-NMR (CDCl$_3$): δ=0.89 (3H), 0.96 (3H), 0.85-1.97 (17H), 1.12 (3H), 2.16-3.01 (10H), 2.82 (3H), 3.44 (1H), 3.65 (1H), 4.41+4.53 (1H), 4.98 (1H), 5.03 (1H), 5.15 (1H), 5.60 (1H), 5.71 (1H), 5.90 (1H), 6.68 (2H), 7.35 (1H), 7.77 (1H), 7.89+7.96 (1H) ppm.

Example EL4

(1S,3S,7S,10R,11S,12S,16R)-[5-(2,5-Dioxo-2,5-dihydro-pyrrol-1-yl)-pentyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester (A) and (1R,3S,7S,10R,11S,12S,16S)-[5-(2,5-Dioxo-2,5-dihydro-pyrrol-1-yl)-pentyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester (B)

26 mg (35.3 µmol) of the compound that is prepared according to Example EL3 is reacted analogously to Example EL2, and after purification, 9.1 mg (12.1 µmol, 34%) of title compound A as well as 3.0 mg (4.0 µmol, 11%) of title compound B are isolated in each case as a colorless foam.

$^1$H-NMR (CDCl$_3$) of A: δ=0.83-1.94 (15H), 0.98 (3H), 1.14 (3H), 1.16 (3H), 1.32 (3H), 2.15-2.82 (8H), 2.84 (3H), 3.44 (2H), 3.51 (1H), 3.66 (1H), 4.46 (1H), 4.99 (1H), 5.04 (1H), 5.54 (1H), 5.69 (1H), 6.06 (1H), 6.68 (2H), 7.33 (1H), 7.80 (1H), 7.89 (1H) ppm.

$^1$H-NMR (CDCl$_3$) of B: δ=0.78-2.74 (23H), 1.01 (3H), 1.03 (3H), 1.33 (3H), 2.82 (3H), 2.91 (1H), 3.14 (1H), 3.39 (1H), 3.47 (2H), 3.67 (1H), 4.12 (1H), 4.49 (1H), 4.92-5.06 (2H), 5.53+5.80 (1H), 5.69 (1H), 6.11 (1H), 6.68 (2H), 7.34 (1H), 7.74+7.79 (1H), 7.89+8.02 (1H) ppm.

Example EL5

(4S,7R,8S,9S,13Z,16S)-[10-(2,5-Dioxo-2,5-dihydro-pyrrol-1-yl)-decyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester Example EL5a (4S,7R,8S,9S,13Z,16S)-[10-(2,5-Dioxo-2,5-dihydro-pyrrol-1-yl)-decyl]-carbamic acid-7-allyl-8-tert-butyl-dimethylsilyloxy-5,5,9,13-tetramethyl-16-(2-methyl-benzothiazol-5-yl)-2,6-dioxo-oxacyclohexadec-13-en-4-yl ester 50 mg (78 µmol) of the compound that is prepared according to Example EL1a is reacted analogously to Example EL1b with the linker that is produced according to Example L6a, and after purification, 56 mg (60.8 µmol, 78%) of the title compound is isolated as a colorless oil.

Example EL5

(4S,7R,8S,9S,13Z,16S)-[10-(2,5-Dioxo-2,5-dihydro-pyrrol-1-yl)-decyl]-carbamic acid-7-allyl-8-hydroxy-5,5,9,13-tetramethyl-16-(2-methyl-benzothiazol-5-yl)-2,6-dioxo-oxacyclohexadec-13-en-4-yl ester 20 mg (21.7 µmol) of the compound that is prepared according to Example EL5a is reacted analogously to Example EL1, and after purification, 10 mg (12.4 µmol, 57%) of the title compound is isolated as a colorless foam.

$^1$H-NMR (CDCl$_3$): δ=0.91-1.87 (22H), 0.97 (3H), 1.13 (3H), 1.17 (3H), 1.70 (3H), 2.18-2.69 (8H), 2.80 (1H), 2.82 (3H), 2.96 (1H), 3.47 (1H), 3.50 (2H), 3.66 (1H), 3.97+4.36 (1H), 4.98 (1H), 5.04 (1H), 5.16 (1H), 5.61 (1H), 5.72 (1H), 5.91 (1H), 6.68 (2H), 7.37 (1H), 7.77 (1H), 7.90+7.97 (1H) ppm.

Example EL6

(1S,3S,7S,10R,11S,12S,16R)-[10-(2,5-Dioxo-2,5-dihydro-pyrrol-1-yl)-decyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester (A) and (1R,3S,7S,10R,11S,12S,16S)-[10-(2,5-Dioxo-2,5-dihydro-pyrrol-1-yl)-decyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester (B)

18 mg (22 µmol) of the compound that is prepared according to Example EL5 is reacted analogously to Example EL2, and after purification, 9.2 mg (11.2 µmol, 51%) of title compound A as well as 3.2 mg (3.9 µmol, 18%) of title compound B are isolated in each case as a colorless foam.

¹H-NMR (CDCl₃) of A: δ=0.98 (3H), 1.14 (3H), 1.16 (3H), 1.32 (3H), 1.03-1.67 (21H), 1.71-1.94 (3H), 2.18-2.78 (9H), 2.83 (3H), 3.50 (3H), 3.66 (1H), 3.87+4.43 (1H), 4.98 (1H), 5.04 (1H), 5.53 (1H), 5.69 (1H), 6.07 (1H), 6.68 (2H), 7.33 (1H), 7.80 (1H), 7.89+7.93 (1H) ppm.

¹H-NMR (CDCl₃) of B: δ=0.80-1.64 (21H), 1.01 (3H), 1.03 (3H), 1.25 (3H), 1.33 (3H), 1.79-2.25 (5H), 2.34+3.14 (1H), 2.52-2.76 (4H), 2.81 (3H), 2.91 (1H), 3.40 (1H), 3.51 (2H), 3.67+3.82 (1H), 4.13+4.26 (1H), 4.46 (1H), 4.94 (1H), 5.01 (1H), 5.70 (1H), 5.81+5.94 (1H), 6.05+6.12 (1H), 6.68 (2H), 7.36 (1H), 7.74 (1H), 7.91+8.02 (1H) ppm.

Example EL7

(4S,7R,8S,9S,13Z,16S)-[3-(2,5-Dioxo-2,5-dihydro-pyrrol-1-yl)-propyl]-carbamic acid-7-allyl-4-hydroxy-5,5,9,13-tetramethyl-16-(2-methyl-benzothiazol-5-yl)-2,6-dioxo-oxacyclohexadec-13-en-8-yl ester Example EL7a (4S,7R,8S,9S,13Z,16S)-7-Allyl-4-(tert-butyl-dimethyl-silanyloxy)-8-hydroxy-5,5,9,13-tetramethyl-16-(2-methyl-benzothiazol-5-yl)-oxacyclohexadec-13-ene-2,6-dione The solution of 5.3 g (7.01 mmol) of (4S,7R,8S,9S,13Z,16S)-7-allyl-4,8-bis(tert-butyl-dimethyl-silanyloxy)-5,5,9,13-tetramethyl-16-(2-methyl-benzothiazol-5-yl)-oxacyclohexadec-13-ene-2,6-dione, which was produced analogously to the process described in WO 00/66589, in a mixture of 85 ml of tetrahydrofuran and 85 ml of acetonitrile, is mixed with 31.7 ml of hexafluorosilicic acid, cooled to 0° C., 8.1 ml of trifluoroacetic acid is added dropwise, and it is stirred for 20 hours at 0° C. It is poured into water, neutralized by adding a saturated sodium bicarbonate solution and extracted several times with ethyl acetate. The combined organic extracts are washed with saturated sodium chloride solution, dried over sodium sulfate, and the residue that is obtained after filtration and removal of the solvent is purified by chromatography on fine silica gel. 2.82 g (4.39 mmol, 63%) of the title compound is isolated as a colorless solid.

¹H-NMR (CDCl₃): δ=-0.09 (3H), 0.08 (3H), 0.84 (9H), 1.08 (3H), 1.10 (3H), 1.12 (3H), 1.21-1.86 (5H), 1.70 (3H), 2.15 (1H), 2.29-2.97 (8H), 2.84 (3H), 3.14 (1H), 3.96 (1H), 4.03 (1H), 4.97-5.06 (2H), 5.23 (1H), 5.61 (1H), 5.77 (1H), 7.35 (1H), 7.79 (1H), 7.93 (1H) ppm.

Example EL7b (4S,7R,8S,9S,13Z,16S)-[3-(2,5-Dioxo-2,5-dihydro-pyrrol-1-yl)-propyl]-carbamic acid-7-allyl-4-tert-butyl-dimethylsilyloxy-5,5,9,13-tetramethyl-16-(2-methyl-benzothiazol-5-yl)-2,6-dioxo-oxacyclohexadec-13-en-8-yl ester 100 mg (156 μmol) of the compound that is prepared according to Example EL7a is reacted analogously to Example EL1b with the linker that is produced according to Example L4a, and after purification, 121 mg (147 μmol, 94%) of the title compound is isolated as a colorless oil.

Example EL7

(4S,7R,8S,9S,13Z,16S)-[3-(2,5-Dioxo-2,5-dihydro-pyrrol-1-yl)-propyl]-carbamic acid-7-allyl-4-hydroxy-5,5,9,13-tetramethyl-16-(2-methyl-benzothiazol-5-yl)-2,6-dioxo-oxacyclohexadec-13-en-8-yl ester 46 mg (56 μmol) of the compound that is prepared according to Example EL7b is reacted analogously to Example EL1, and after purification, 17 mg (24 μmol, 43%) of the title compound is isolated as a colorless foam.

¹H-NMR (CDCl₃): δ=0.99-1.30 (2H), 1.03 (3H), 1.07 (3H), 1.21 (3H), 1.51-1.97 (6H), 1.72 (3H), 2.27-2.61 (6H), 2.83 (3H), 2.88 (1H), 3.09 (1H), 3.14 (2H), 3.51 (1H), 3.58 (2H), 4.04 (1H), 4.96-5.04 (2H), 5.12 (1H), 5.19 (1H), 5.28 (1H), 5.75 (1H), 5.86 (1H), 6.66 (2H), 7.35 (1H), 7.78 (1H), 7.96 (1H) ppm.

Example EL8

(1S,3S,7S,10R,11S,12S,16R)-[3-(2,5-Dioxo-2,5-dihydro-pyrrol-1-yl)-propyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]heptadec-11-yl ester (A) and (1S,3S,7S,10R,11S,12S,16R)-[3-(2,5-Dioxo-2,5-dihydro-pyrrol-1-yl)-propyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]-heptadec-11-yl ester (B)

29 mg (41 μmol) of the compound that is prepared according to Example EL7 is reacted analogously to Example EL2, and after purification, 18 mg (24.9 μmol, 61%) of title compound A as well as 3.0 mg (4.1 μmol, 10%) of title compound B are isolated in each case as a colorless foam.

¹H-NMR (CDCl₃) of A: δ=0.98 (3H), 1.05 (3H), 1.24 (3H), 1.26 (3H), 1.12-1.83 (9H), 2.12-2.46 (4H), 2.59 (2H), 2.76 (1H), 2.84 (3H), 3.14 (2H), 3.59 (3H), 3.98 (1H), 4.10 (1H), 4.95-5.02 (2H), 5.17 (2H), 5.77 (1H), 6.19 (1H), 6.70 (2H), 7.38 (1H), 7.82 (1H), 7.97 (1H) ppm.

¹H-NMR (CDCl₃) of B: δ=0.96 (3H), 1.01 (3H), 1.13-1.86 (1H), 1.28 (3H), 1.32 (3H), 2.16-2.50 (6H), 2.84 (3H), 3.02 (1H), 3.15 (2H), 3.50 (1H), 3.61 (2H), 3.88 (1H), 4.19 (1H), 4.96-5.04 (2H), 5.13 (1H), 5.28 (1H), 5.78 (1H), 6.33 (1H), 6.71 (2H), 7.36 (1H), 7.81 (1H), 7.96 (1H) ppm.

Example EL9

(4S,7R,8S,9S,13Z,16S)-[5-(2,5-Dioxo-2,5-dihydro-pyrrol-1-yl)-pentyl]-carbamic acid-7-allyl-4-hydroxy-5,5,9,13-tetramethyl-16-(2-methyl-benzothiazol-5-yl)-2,6-dioxo-oxacyclohexadec-13-en-8-yl ester Example EL9a (4S,7R,8S,9S,13Z,16S)-[5-(2,5-Dioxo-2,5-dihydro-pyrrol-1-yl)-pentyl]-carbamic acid-7-allyl-4-tert-butyl-dimethylsilyloxy-5,5,9,13-tetramethyl-16-(2-methyl-benzothiazol-5-yl)-2,6-dioxo-oxacyclohexadec-13-en-8-yl ester 100 mg (156 μmol) of the compound that is prepared according to Example EL7a is reacted analogously to Example EL1b with the linker that is produced according to Example L5a, and after purification, (65.9 µmol, 42%) of the title compound is isolated as a colorless oil.

Example EL9

(4S,7R,8S,9S,13Z,16S)-[5-(2,5-Dioxo-2,5-dihydro-pyrrol-1-yl)-pentyl]-carbamic acid-7-allyl-4-hydroxy-5,5,9,13-tetramethyl-16-(2-methyl-benzothiazol-5-yl)-2,6-dioxo-oxacyclohexadec-13-en-8-yl ester 56 mg (65.9 µmol) of the compound that is prepared according to Example EL7b is reacted analogously to Example EL1, and after purification, 24.7 mg (33.6 µmol, 51%) of the title compound is isolated as a colorless foam.
$^1$H-NMR (CDCl$_3$): δ=0.97-1.84 (11H), 1.02 (3H), 1.07 (3H), 1.20 (3H), 1.71 (3H), 1.91 (1H), 2.27-2.57 (6H), 2.84 (3H), 2.88 (1H), 2.95 (1H), 3.16 (2H), 3.51 (3H), 4.02 (1H), 4.46+4.83 (1H), 4.94-5.03 (2H), 5.15 (1H), 5.20 (1H), 5.74 (1H), 5.84 (1H), 6.68 (2H), 7.35 (1H), 7.80 (1H), 7.96 (1H) ppm.

Example EL 10

(1S,3S,7S,10R,11S,12S,16R)-[5-(2,5-Dioxo-2,5-dihydro-pyrrol-1-yl)-pentyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]heptadec-11-yl ester (A) and (1S,3S,7S,10R,11S,12S,16R)-[5-(2,5-Dioxo-2,5-dihydro-pyrrol-1-yl)-pentyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]hepta-dec-11-yl ester (B)

24.7 mg (33.6 µmol) of the compound that is prepared according to Example EL9 is reacted analogously to Example EL2, and after purification, 16.7 mg (22.2 µmol, 66%) of title compound A as well as 2.0 mg (2.7 µmol, 8%) of title compound B are isolated in each case as a colorless foam.
$^1$H-NMR (CDCl$_3$) of A: δ=0.98 (3H), 1.04 (3H), 1.10-1.75 (13H), 1.23 (3H), 1.26 (3H), 2.09-2.62 (6H), 2.75 (1H), 2.84 (3H), 3.15 (2H), 3.51 (2H), 3.57 (1H), 3.99 (1H), 4.08 (1H), 4.46+4.74 (1H), 4.93-5.02 (2H), 5.18 (1H), 5.76 (1H), 6.18 (1H), 6.68 (2H), 7.38 (1H), 7.82 (1H), 7.97 (1H) ppm.
$^1$H-NMR (CDCl$_3$) of B: δ=0.83-1.85 (13H), 0.95 (3H), 1.01 (3H), 1.27 (3H), 1.32 (3H), 2.17-2.49 (6H), 2.84 (3H), 3.03 (1H), 3.17 (2H), 3.48 (1H), 3.53 (2H), 3.86 (1H), 4.18 (1H), 4.66 (1H), 4.94-5.03 (2H), 5.27 (1H), 5.76 (1H), 6.33 (1H), 6.69 (2H), 7.35 (1H), 7.81 (1H), 7.96 (1H) ppm.

Example EL11

(1S,3S(E),7S,10R,11S,12S,16R)-[3-(2,5-Dioxo-2,5-dihydro-pyrrol-1-yl)-propyl]-carbamic acid 7-[3-(2,5-dioxo-2,5-dihydro-pyrrol-1-yl)-propylcarbamoyloxy]-8,8,10,12,16-pentamethyl-3-[1-methyl-2-(2-methyl-thiazol-4-yl)-vinyl]-5,9-dioxo-4,17-dioxabicyclo[14.1.0]heptadec-11-yl ester 10 mg (19.7 µmol) of (1S,3S(E),7S,10R,11S,12S,16R)-7,11-dihydroxy-8,8,10,12,16-pentamethyl-3-[1-methyl-2-(2-methyl-thiazol-4-yl)-vinyl]-5,9-dioxo-4,17-dioxa-bicyclo [14.1.0]heptadecane is reacted analogously to Example EL1b with the linker that is produced according to Example L4a, and after purification, 7 mg (8.06 µmol, 41%) of the title compound is isolated as a colorless oil.
$^1$H-NMR (CDCl$_3$): δ=0.88-2.20 (13H), 1.03 (3H), 1.05 (3H), 1.10 (3H), 1.24 (3H), 1.28 (3H), 2.08 (3H), 2.63-2.85 (4H), 2.71 (3H), 2.99-3.25 (3H), 3.41-3.50 (3H), 3.62 (2H), 4.88-5.70 (5H), 6.52 (1H), 6.69 (2H), 6.71 (2H), 7.02 (1H) ppm.

Example EL12

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-(2,5-dioxo-2,5-dihydro-pyrrol-1-yl)-phenyl ester

Example EL12a (4S,7R,8S,9S,13Z,16S)-Chloroformic acid-7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester The solution of 1.0 g (1.56 mmol) of the compound, prepared according to Example EL1a, in 20 ml of dichloromethane is mixed at 0° C. with the solution of 285 mg of triphosgene in 6 ml of dichloromethane, 160 µl of pyridine, and it is stirred for 2.5 hours at 23° C. It is concentrated by evaporation, the residue is dissolved in ethyl acetate, washed with water and saturated sodium chloride solution, and dried over magnesium sulfate. The residue that is obtained after filtration and removal of the solvent is purified by chromatography on fine silica gel. 1.08 g (1.53 mmol, 98%) of the title compound is isolated.

Example EL12b (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 4-(2,5-dioxo-2,5-dihydro-pyrrol-1-yl)-phenyl ester The solution of 267 mg (370 µmol) of the compound, prepared according to Example EL12a, in 16 ml of ethyl acetate, is mixed with 51 µl of triethylamine, 700 mg of the compound that is prepared according to Example L8, and it is stirred for 16 hours at 23° C. It is poured into water, extracted several times with ethyl acetate, the combined organic extracts are washed with saturated sodium chloride solution and dried over magnesium sulfate. The residue that is obtained after filtration and removal of the solvent is purified by chromatography on fine silica gel. 188 mg (219 µmol, 59%) of the title compound is isolated.

Example EL12

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-(2,5-dioxo-2,5-dihydro-pyrrol-1-yl)-phenyl ester Analogously to Example EL1, 248 mg (289 µmol) of the compound that is prepared according to Example EL12a is reacted, and after working-up and purification, 149 mg (201 µmol, 69%) of the title compound is isolated.

¹H-NMR (CDCl₃): δ=1.08 (3H), 1.14 (3H), 1.26 (3H), 1.04-1.90 (8H), 2.24-2.57 (6H), 2.68-2.99 (3H), 2.81 (3H), 3.45 (1H), 3.72 (1H), 5.02 (1H), 5.06 (1H), 5.17 (1H), 5.65 (1H), 5.74 (1H), 5.98 (1H), 6.79 (2H), 6.88 (2H), 7.21 (2H), 7.33 (1H), 7.64 (1H), 7.97 (1H) ppm.

Example EL13

(1S,3S,7S,10R,11S,12S,16R)-Carbonic acid-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-(2,5-dioxo-2,5-dihydro-pyrrol-1-yl)-phenyl ester Analogously to Example EL2, 144 mg (194 µmol) of the compound that is prepared according to Example EL12 is reacted, and after working-up and purification, 89 mg (117 µmol, 60%) of the title compound is isolated.

¹H-NMR (CDCl₃): δ=1.10 (3H), 1.14 (3H), 1.27 (3H), 1.32 (3H), 1.19-1.85 (7H), 2.08-2.89 (8H), 2.81 (3H), 3.50 (1H), 3.70 (1H), 5.02 (1H), 5.07 (1H), 5.58 (1H), 5.72 (1H), 6.10 (1H), 6.81 (2H), 6.88 (2H), 7.21 (2H), 7.31 (1H), 7.68 (1H), 7.93 (1H) ppm.

Example EL14

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-(2,5-dioxo-2,5-dihydro-pyrrol-1-yl)-phenyl ester Example EL14a (4S,7R,8S,9S,13Z,16S)-Chloroformic acid-7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester Analogously to Example EL12a, 1.0 g (1.56 mmol) of the compound that is prepared according to Example EL7a is reacted, and 1.05 g (1.49 mmol, 96%) of the title compound is isolated.

Example EL14b (4S,7R,8S,9S,13Z,16S)-Carbonic acid 7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester 4-(2,5-dioxo-2,5-dihydro-pyrrol-1-yl)-phenyl ester The solution of 313 mg (0.44 mmol) of the compound, prepared according to Example EL14a, in 19 ml of ethyl acetate is mixed with 840 mg of the compound that is prepared according to Example L8, 61.5 µl of triethylamine, and it is stirred for 16 hours at 23° C. It is mixed with water, extracted several times with ethyl acetate, the combined organic extracts are washed with saturated sodium chloride solution and dried over sodium sulfate. The residue that is obtained after filtration and removal of the solvent is purified by chromatography on fine silica gel. 298 mg (348 µmol, 79%) of the title compound is isolated.

Example EL14

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-(2,5-dioxo-2,5-dihydro-pyrrol-1-yl)-phenyl ester Analogously to Example EL1, 304 mg (355 µmol) of the compound that is prepared according to Example EL14a is reacted, and after working-up and purification, 67 mg (90 µmol, 25%) of the title compound is isolated.

¹H-NMR (CDCl₃): δ=1.09 (3H), 1.11 (3H), 0.84-2.02 (7H), 1.27 (3H), 1.72 (3H), 2.29-2.58 (6H), 2.84 (3H), 2.89 (1H), 2.96 (1H), 3.63 (1H), 4.03 (1H), 5.06 (2H), 5.23 (2H), 5.80 (1H), 5.85 (1H), 6.86 (2H), 7.30 (2H), 7.35 (1H), 7.39 (1H), 7.80 (1H), 7.96 (1H) ppm.

Example EL15

(1S,3S,7S,10R,11S,12S,16R)-Carbonic acid-10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-(2,5-dioxo-2,5-dihydro-pyrrol-1-yl)-phenyl ester Analogously to Example EL2, 67 mg (90 µmol) of the compound that is prepared according to Example EL14 is reacted, and after working-up and purification, 32 mg (42 µmol, 47%) of the title compound is isolated.

¹H-NMR (CDCl₃): δ=1.05 (3H), 1.06 (3H), 1.25 (3H), 1.35 (3H), 1.21-1.90 (7H), 2.18 (2H), 2.33-2.67 (4H), 2.73 (1H), 2.85 (3H), 3.79 (1H), 4.11 (1H), 4.33 (1H), 5.02 (1H), 5.07 (1H), 5.31 (1H), 5.81 (1H), 6.27 (1H), 6.86 (2H), 7.29 (2H), 7.35-7.41 (3H), 7.83 (1H), 7.99 (1H) ppm.

Example EL16

(1S,3S(E),7S,10R,11S,12S,16R)-N-[1-({4-[2-(7,11-Dihydroxy-8,8,10,12,16-pentamethyl-5,9-dioxo-4,17-dioxa-bicyclo[14.1.0]heptadec-3-yl)-propenyl]-thiazol-2-ylmethyl}-carbamoyl)-ethyl]-3-methyltrisulfanyl-N-methyl-propionamide The solution of 7 mg (13 µmol) of (1S,3S(E),7S,10R,11S,12S,16R)-3-[2-(2-aminomethyl-thiazol-4-yl)-1-methyl-vinyl]-7,11-dihydroxy-8,8,10,12,16-penta-methyl-4,17-dioxa-bicyclo[14.1.0]heptadecane-5,9-dione, which was produced analogously to the process described in WO 99/01124, in 0.5 ml of dichloromethane is mixed with 7 mg of the compound that is prepared according to Example L1, 0.4 mg of 4-dimethylaminopyridine and 4 mg of N,N'-dicyclohexylcarbodiimide are added, and it is stirred for 20 minutes at 23° C. Precipitated urea is filtered out, and it is purified by chromatography on a preparative thin-layer plate. 5 mg (6.5 µmol, 50%) of the title compound is isolated.

¹H-NMR (CDCl₃): δ=1.00 (3H), 1.08 (3H), 1.17 (3H), 1.23-1.77 (5H), 1.28 (3H), 1.36 (3H), 1.39 (3H), 1.88-2.13 (3H), 2.10 (3H), 2.37 (1H), 2.49-2.66 (2H), 2.55 (3H), 2.77-2.92 (4H), 2.97 (3H), 3.16 (2H), 3.31 (1H), 3.77 (1H), 4.08 (1H), 4.19 (1H), 4.62 (1H), 4.76 (1H), 5.25 (1H), 5.45 (1H), 6.57 (1H), 7.01 (1H), 7.06 (1H) ppm.

Example EL 17

(1S,3S(E),7S,10R,11S,12S,16R)-2-[Methyl-(3-methyltrisulfanyl-propionyl)-amino]-propionic acid-4-[2-(7,11-dihydroxy-8,8,10,12,16-pentamethyl-5,9-dioxo-4,17-dioxa-bicyclo [14.1.0]heptadec-3-yl)-propenyl]-thiazol-2-ylmethyl ester Analogously to Example EL16, 10 mg (19 µmol) of (1S,3S(E),7S,10R,11S, 12S,16R)-7,11-dihydroxy-3-[2-(2-hydroxymethyl-thiazol-4-yl)-1-methyl-vinyl]-8,8,10,12,16-pentamethyl-4,17-dioxa-bicyclo[14.1.0]heptadecane-5,9-dione, which was produced analogously to the process that is described in WO 99/01124, is reacted, and 2.2 mg (2.8 µmol, 15%) of the title compound is isolated.

$^1$H-NMR (CDCl$_3$): δ=1.01 (3H), 1.09 (3H), 1.18 (3H), 1.27 (1H), 1.28 (3H), 1.32-1.76 (3H), 1.37 (3H), 1.47 (3H), 1.95 (1H), 2.06 (1H), 2.12 (3H), 2.38 (1H), 2.51-2.63 (2H), 2.56 (3H), 2.78-2.92 (5H), 2.97+3.01 (3H), 3.13-3.35 (3H), 3.71 (1H), 3.77 (1H), 4.00 (1H), 4.18 (1H), 5.25 (1H), 5.39 (2H), 5.45 (1H), 6.60 (1H), 7.17 (1H) ppm.

Example EL18

4-(2,5-Dioxo-2,5-dihydro-pyrrol-1-yl)-butanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester

Example EL18a 4-(2,5-Dioxo-2,5-dihydro-pyrrol-1-yl)-butanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL12b, 200 mg (284 µmol) of the compound that is prepared according to Example EL12a is reacted with 770 mg of the compound that is prepared according to Example L9, and after working-up and purification, 129 mg (129 µmol, 45%) of the title compound is isolated.

Example EL18

4-(2,5-Dioxo-2,5-dihydro-pyrrol-1-yl)-butanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL1, 129 mg (129 µmol) of the compound that is prepared according to Example EL18a is reacted, and after working-up and purification, 71 mg (80 µmol, 62%) of the title compound is isolated.

$^1$H-NMR (CDCl$_3$): δ=0.88-2.11 (1H), 1.02 (3H), 1.14 (3H), 1.71 (3H), 2.23-2.56 (6H), 2.63-2.71 (3H), 2.74 (3H), 2.97 (1H), 3.39 (1H), 3.68 (3H), 4.58 (1H), 4.78 (1H), 5.01 (1H), 5.05 (1H), 5.18 (1H), 5.56 (1H), 5.71 (1H), 5.97 (1H), 6.73 (2H), 7.19 (1H), 7.31 (1H), 7.36 (1H), 7.75 (1H), 7.77 (1H), 7.95 (1H) ppm.

Example EL19

4-(2,5-Dioxo-2,5-dihydro-pyrrol-1-yl)-butanoic acid 4-(1S,3S,7S,10R,11S,12S,16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (A) and 4-(2,5-Dioxo-2,5-dihydro-pyrrol-1-yl)-butanoic acid 4-(1R,3S,7S,10R,11S,12S,16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (B)

Analogously to Example EL2, 71 mg (80 µmol) of the compound that is prepared according to Example EL18 is reacted, and after working-up and purification, 41 mg (45 µmol, 57%) of title compound A as well as 12 mg (13 µmol, 17%) of title compound B are isolated.

$^1$H-NMR (CDCl$_3$) of A: δ=1.04 (3H), 1.14 (3H), 1.16 (3H), 1.32 (3H), 1.34-1.84 (6H), 2.01-2.74 (12H), 2.78 (3H), 2.86 (1H), 3.44 (1H), 3.68 (3H), 4.56 (1H), 4.74 (1H), 5.01 (1H), 5.06 (1H), 5.47 (1H), 5.70 (1H), 6.07 (1H), 6.73 (2H), 7.20 (1H), 7.32 (1H), 7.36 (1H), 7.77 (1H), 7.81 (1H), 7.90 (1H) ppm.

Example EL20

6-(2,5-Dioxo-2,5-dihydro-pyrrol-1-yl)-hexanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester

Example EL20a 6-(2,5-Dioxo-2,5-dihydro-pyrrol-1-yl)-hexanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL12b, 243 mg (345 µmol) of the compound that is prepared according to Example EL12a is reacted with 1 g of the compound that is prepared according to Example L10, and after working-up and purification, 25 mg (24 µmol, 7%) of the title compound is isolated.

Example EL20

6-(2,5-Dioxo-2,5-dihydro-pyrrol-1-yl)-hexanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL1, 212 mg (206 µmol) of the compound that is prepared according to Example EL20a is reacted, and after working-up and purification, 117 mg (128 µmol, 62%) of the title compound is isolated.

$^1$H-NMR (CDCl$_3$): δ=1.01 (3H), 1.14 (6H), 1.04-2.78 (20H), 1.70 (3H), 2.74 (3H), 2.97 (1H), 3.39 (1H), 3.56 (2H), 3.68 (1H), 4.11 (1H), 4.58 (1H), 4.77 (1H), 5.00 (1H), 5.05 (1H), 5.18 (1H), 5.56 (1H), 5.71 (1H), 5.97 (1H), 6.69 (2H), 7.12 (1H), 7.29 (1H), 7.36 (1H), 7.75 (2H), 7.94 (1H) ppm.

Example EL21

6-(2,5-Dioxo-2,5-dihydro-pyrrol-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (A) and 6-(2,5-Dioxo-2,5-dihydro-pyrrol-1-yl)-hexanoic acid 4-(1R,3S,7S,10R,11S,12S,16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (B)

Analogously to Example EL2, 117 mg (128 µmol) of the compound that is prepared according to Example EL20 is reacted, and after working-up and purification, 63 mg (68 µmol, 53%) of title compound A as well as 19 mg (20 µmol, 16%) of title compound B are isolated.
$^1$H-NMR (CDCl$_3$) of A: δ=1.03 (3H), 1.14 (3H), 1.15 (3H), 1.32 (3H), 1.07-2.75 (22H), 2.77 (3H), 2.86 (1H), 3.44 (1H), 3.55 (2H), 3.69 (1H), 4.55 (1H), 4.77 (1H), 5.01 (1H), 5.06 (1H), 5.47 (1H), 5.70 (1H), 6.08 (1H), 6.70 (2H), 7.14 (1H), 7.31 (1H), 7.35 (1H), 7.76 (1H), 7.80 (1H), 7.90 (1H) ppm.

Example EL22

11-(2,5-Dioxo-2,5-dihydro-pyrrol-1-yl)-undecanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester

Example EL22a 11-(2,5-Dioxo-2,5-dihydro-pyrrol-1-yl)-undecanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL12b, 243 mg (345 µmol) of the compound that is prepared according to Example EL12a is reacted with 1.19 g of the compound that is prepared according to Example L11, and after working-up and purification, 171 mg (155 µmol, 45%) of the title compound is isolated.

Example EL22

11-(2,5-Dioxo-2,5-dihydro-pyrrol-1-yl)-undecanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenyl ester Analogously to Example EL1, 171 mg (155 µmol) of the compound that is prepared according to Example EL22a is reacted, and after working-up and purification, 108 mg (110 µmol, 71%) of the title compound is isolated.
$^1$H-NMR (CDCl$_3$): δ=1.02 (3H), 1.14 (6H), 0.88-2.56 (28H), 1.70 (3H), 2.63 (2H), 2.71 (1H), 2.74 (3H), 2.98 (1H), 3.39 (1H), 3.50 (2H), 3.69 (1H), 4.58 (1H), 4.77 (1H), 5.00 (1H), 5.05 (1H), 5.17 (1H), 5.56 (1H), 5.71 (1H), 5.97 (1H), 6.68 (2H), 7.11 (1H), 7.29 (1H), 7.36 (1H), 7.75 (1H), 7.76 (1H), 7.94 (1H) ppm.

Example EL23

11-(2,5-Dioxo-2,5-dihydro-pyrrol-1-yl)-undecanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (A) and 11-(2,5-Dioxo-2,5-dihydro-pyrrol-1-yl)-undecanoic acid 4-(1R,3S,7S,10R,11S,12S,16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester (B)

Analogously to Example EL2, 108 mg (110 µmol) of the compound that is prepared according to Example EL22 is reacted, and after working-up and purification, 65.9 mg (65.8 µmol, 60%) of title compound A as well as 19.8 mg (20 µmol, 18%) of title compound B are isolated.
$^1$H-NMR (CDCl$_3$) of A: δ=1.04 (3H), 1.14 (3H), 1.15 (3H), 1.63 (3H), 0.92-1.85 (23H), 2.10-2.81 (9H), 2.77 (3H), 2.86 (1H), 3.45 (1H), 3.51 (2H), 3.69 (1H), 4.55 (1H), 4.74 (1H), 5.01 (1H), 5.06 (1H), 5.47 (1H), 5.70 (1H), 6.08 (1H), 6.68 (2H), 7.13 (1H), 7.31 (1H), 7.35 (1H), 7.77 (1H), 7.80 (1H), 7.90 (1H) ppm.

Example EL24

4-(2,5-Dioxo-2,5-dihydro-pyrrol-1-yl)-butanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester

Example EL24a 4-(2,5-Dioxo-2,5-dihydro-pyrrol-1-yl)-butanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL12b, 271 mg (385 µmol) of the compound that is prepared according to Example EL14a is reacted with 1.04 g of the compound that is prepared according to Example L9, and after working-up and purification, 193 mg (193 µmol, 50%) of the title compound is isolated.

Example EL24

4-(2,5-Dioxo-2,5-dihydro-pyrrol-1-yl)-butanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL1, 193 mg (193 µmol) of the compound that is prepared according to Example EL24a is reacted, and after working-up and purification, 107 mg (120 µmol, 62%) of the title compound is isolated.
$^1$H-NMR (CDCl$_3$): δ=1.02 (3H), 1.07 (3H), 1.23 (3H), 0.97-2.13 (8H), 1.71 (3H), 2.28-2.54 (6H), 2.67 (2H), 2.84 (3H), 2.88 (1H), 2.95 (1H), 3.56 (1H), 3.67 (2H), 4.01 (1H), 4.93 (1H), 4.98 (1H), 5.17 (1H), 5.22 (3H), 5.70 (1H), 5.84 (1H), 6.72 (2H), 7.30 (1H), 7.34 (1H), 7.69 (1H), 7.80 (1H), 7.95 (1H), 8.13 (1H) ppm.

Example EL25

4-(2,5-Dioxo-2,5-dihydro-pyrrol-1-yl)-butanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester (A) and 4-(2,5-Dioxo-2,5-dihydro-pyrrol-1-yl)-butanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester (B)

Analogously to Example EL2, 102 mg (115 μmol) of the compound that is prepared according to Example EL19 is reacted, and after working-up and purification, 65 mg (72 μmol, 63%) of title compound A as well as 3 mg (3.3 μmol, 3%) of title compound B are isolated.

$^1$H-NMR (CDCl$_3$) of A: δ=0.97 (3H), 1.04 (3H), 1.23 (3H), 1.31 (3H), 1.10-2.75 (18H), 2.85 (3H), 3.68 (2H), 3.71 (1H), 4.09 (1H), 4.28 (1H), 4.92 (1H), 4.97 (1H), 5.20 (2H), 5.23 (1H), 5.72 (1H), 6.26 (1H), 6.72 (2H), 7.30 (1H), 7.37 (1H), 7.68 (1H), 7.83 (1H), 7.98 (1H), 8.13 (1H) ppm.

Example EL26

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester

Example EL26a 6-(2,5-Dioxo-2,5-dihydro-pyrrol-1-yl)-hexanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL12b, 273 mg (387 μmol) of the compound that is prepared according to Example EL14a is reacted with 1.12 g of the compound that is prepared according to Example L10, and after working-up and purification, 69 mg (67 μmol, 17%) of the title compound is isolated.

Example EL26

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL1, 69 mg (67 μmol) of the compound that is prepared according to Example EL26a is reacted, and after working-up and purification, 26 mg (28 μmol, 42%) of the title compound is isolated.

$^1$H-NMR (CDCl$_3$): δ=0.93 (3H), 0.95 (3H), 1.16 (3H), 1.60 (3H), 0.98-2.61 (20H), 2.73 (3H), 2.77 (1H), 3.45 (3H), 3.83 (1H), 4.05 (1H), 4.83 (1H), 4.88 (1H), 5.05 (1H), 5.13 (3H), 5.62 (1H), 5.74 (1H), 6.61 (2H), 7.16 (1H), 7.26 (1H), 7.60 (1H), 7.70 (1H), 7.88 (1H), 8.03 (1H) ppm.

Example EL27

6-(2,5-Dioxo-2,5-dihydro-pyrrol-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester (A) and 6-(2,5-Dioxo-2,5-dihydro-pyrrol-1-yl)-hexanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0] heptadec-11-yloxycarbonyloxymethyl]-2-nitro-phenyl ester (B)

Analogously to Example EL2, 38 mg (41 μmol) of the compound that is prepared according to Example EL19 is reacted, and after working-up and purification, 14 mg (15 μmol, 37%) of title compound A as well as 2 mg (2 μmol, 5%) of title compound B are isolated.

$^1$H-NMR (CDCl$_3$) of A: δ=0.96 (3H), 1.03 (3H), 1.08-1.86 (13H), 1.23 (3H), 1.30 (3H), 2.16 (2H), 2.23-2.78 (7H), 2.83 (3H), 3.54 (2H), 3.71 (1H), 4.09 (1H), 4.27 (1H), 4.91 (1H), 4.96 (1H), 5.21 (3H), 5.72 (1H), 6.25 (1H), 6.69 (2H), 7.23 (1H), 7.36 (1H), 7.67 (1H), 7.82 (1H), 7.96 (1H), 8.11 (1H) ppm.

Example EL28

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester

Example EL28a 11-(2,5-Dioxo-2,5-dihydro-pyrrol-1-yl)-undecanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL12b, 273 mg (387 μmol) of the compound that is prepared according to Example EL14a is reacted with 1.34 g of the compound that is prepared according to Example L11, and after working-up and purification, 196 mg (178 μmol, 46%) of the title compound is isolated.

Example EL28

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenyl ester Analogously to Example EL1, 196 mg (178 μmol) of the compound that is prepared according to Example EL28a is reacted, and after working-up and purification, 100 mg (101 μmol, 57%) of the title compound is isolated.

$^1$H-NMR (CDCl$_3$): δ=1.03 (3H), 1.06 (3H), 1.23 (3H), 1.70 (3H), 0.99-1.81 (21H), 1.91 (1H), 2.27-2.53 (6H), 2.63 (2H), 2.83 (3H), 2.88 (1H), 2.95 (1H), 3.51 (2H), 3.56 (1H), 4.00 (1H), 4.92 (1H), 4.98 (1H), 5.13-5.26 (4H), 5.71 (1H), 5.83 (1H), 6.68 (2H), 7.23 (1H), 7.34 (1H), 7.67 (1H), 7.79 (1H), 7.95 (1H), 8.13 (1H) ppm.

Example EL29

11-(2,5-Dioxo-2,5-dihydro-pyrrol-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester (A) and 11-(2,5-Dioxo-2,5-dihydro-pyrrol-1-yl)-undecanoic acid 4-(1R,3S,7S,10R,11S, 12S,16S)-[10-allyl-7-hydroxy-8,8,12,16-tetramethyl-3-(2-methyl-benzothiazol-5-yl)-5,9-dioxo-4,17-dioxa-bicyclo [14.1.0]heptadec-11-yloxycarbonyloxymethyl]-2-nitro-phenyl ester (B)

Analogously to Example EL2, 100 mg (101 μmol) of the compound that is prepared according to Example EL19 is reacted, and after working-up and purification, 21 mg (21 μmol, 21%) of title compound A as well as 2 mg (2 μmol, 2%) of title compound B are isolated.

$^1$H-NMR (CDCl$_3$) of A: δ=0.97 (3H), 1.04 (3H), 1.23 (3H), 0.84-1.84 (24H), 1.71 (3H), 2.15 (2H), 2.23-2.68 (5H), 2.71 (1H), 2.83 (3H), 3.50 (2H), 3.71 (1H), 4.09 (1H), 4.27 (1H), 4.91 (1H), 4.96 (1H), 5.19 (2H), 5.23 (1H), 5.72 (1H), 6.26 (1H), 6.68 (2H), 7.23 (1H), 7.36 (1H), 7.66 (1H), 7.83 (1H), 7.97 (1H), 8.12 (1H) ppm.

Example EL30

4-(2,5-Dioxo-2,5-dihydro-pyrrol-1-yl)-butanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester

Example EL30a 4-(2,5-Dioxo-2,5-dihydro-pyrrol-1-yl)-butanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL12b, 218 mg (309 μmol) of the compound prepared according to Example EL12a are reacted with 314 mg of the compound prepared according to Example L12. After working-up and purification, 103 mg (118 μmol, 35%) of the title compound are isolated.

Example EL30

4-(2,5-Dioxo-2,5-dihydro-pyrrol-1-yl)-butanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL1, 103 mg (118 μmol) of the compound prepared according to Example EL30a are reacted. After working-up and purification, 13 mg (15 μmol, 13%) of the title compound are isolated.

$^1$H-NMR (CDCl$_3$): δ=0.88-1.84 (7H), 1.00 (3H), 1.12 (3H), 1.14 (3H), 1.71 (3H), 2.04 (2H), 2.23-2.71 (8H), 2.74 (3H), 2.99 (1H), 3.40 (1H), 3.67 (3H), 4.48 (1H), 4.76 (1H), 5.00 (1H), 5.04 (1H), 5.18 (1H), 5.55 (1H), 5.71 (1H), 5.98 (1H), 6.72 (2H), 7.01 (2H), 7.08 (2H), 7.37 (1H), 7.76 (1H), 7.96 (1H) ppm.

Example EL31

4-(2,5-Dioxo-2,5-dihydro-pyrrol-1-yl)-butanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-phenyl ester Analogously to Example EL2, 13 mg (15 μmol) of the compound prepared according to Example EL30 are reacted. After working-up and purification, 5.7 mg (6.6 μmol, 44%) of the title compound are isolated.

$^1$H-NMR (CDCl$_3$) of A: δ=1.04 (3H), 1.14 (3H), 1.16 (3H), 1.32 (3H), 1.34-1.84 (6H), 2.04 (2H), 2.15-2.75 (10H), 2.78 (3H), 2.85 (1H), 3.44 (1H), 3.67 (3H), 4.48 (1H), 4.73 (1H), 5.01 (1H), 5.05 (1H), 5.47 (1H), 5.70 (1H), 6.07 (1H), 6.72 (2H), 7.02 (2H), 7.13 (2H), 7.31 (1H), 7.77 (1H), 7.93 (1H) ppm.

Example EL32

6-(2,5-Dioxo-2,5-dihydro-pyrrol-1-yl)-hexanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester

Example EL32a 6-(2,5-Dioxo-2,5-dihydro-pyrrol-1-yl)-hexanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL12b, 218 mg (309 μmol) of the compound prepared according to Example EL12a are reacted with 396 mg of the compound prepared according to Example L13. After working-up and purification, 157 mg (159 μmol, 51%) of the title compound are isolated.

Example EL32

6-(2,5-Dioxo-2,5-dihydro-pyrrol-1-yl)-hexanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL1, 157 mg (159 μmol) of the compound prepared according to Example EL32a are reacted. After working-up and purification, 32 mg (37 μmol, 23%) of the title compound are isolated.

$^1$H-NMR (CDCl$_3$): δ=0.99 (3H), 1.12 (3H), 1.14 (3H), 1.04-2.84 (20H), 1.70 (3H), 2.75 (3H), 3.00 (1H), 3.40 (1H), 3.55 (2H), 3.68 (1H), 4.48 (1H), 4.76 (1H), 5.00 (1H), 5.04 (1H), 5.18 (1H), 5.55 (1H), 5.71 (1H), 5.98 (1H), 6.69 (2H), 6.98 (2H), 7.07 (2H), 7.37 (1H), 7.76 (2H), 7.96 (1H) ppm.

Example EL33

6-(2,5-Dioxo-2,5-dihydro-pyrrol-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-phenyl ester Analogously to Example EL2, 30 mg (34 µmol) of the compound prepared according to Example EL32 are reacted. After working-up and purification, 13 mg (15 µmol, 44%) of the title compound are isolated.
$^1$H-NMR (CDCl$_3$) of A: δ=1.01 (3H), 1.13 (3H), 1.14 (3H), 1.32 (3H), 1.07-2.75 (22H), 2.78 (3H), 2.85 (1H), 3.44 (1H), 3.55 (2H), 3.69 (1H), 4.48 (1H), 4.73 (1H), 5.01 (1H), 5.05 (1H), 5.45 (1H), 5.70 (1H), 6.08 (1H), 6.69 (2H), 6.99 (2H), 7.12 (2H), 7.32 (1H), 7.77 (1H), 7.92 (1H) ppm.

Example EL34

11-(2,5-Dioxo-2,5-dihydro-pyrrol-1-yl)-undecanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester

Example EL34a 11-(2,5-Dioxo-2,5-dihydro-pyrrol-1-yl)-undecanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL12b, 218 mg (309 µmol) of the compound prepared according to Example EL12a are reacted with 422 mg of the compound prepared according to Example L14. After working-up and purification, 77 mg (73 µmol, 24%) of the title compound are isolated.

Example EL34

11-(2,5-Dioxo-2,5-dihydro-pyrrol-1-yl)-undecanoic acid 4-(4S,7R,8S,9S,13Z,16S)-[7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenyl ester Analogously to Example EL1, 77 mg (73 µmol) of the compound prepared according to Example EL34a are reacted. After working-up and purification, 14 mg (15 µmol, 20%) of the title compound are isolated.
$^1$H-NMR (CDCl$_3$): δ=0.99 (3H), 1.11 (3H), 1.14 (3H), 0.88-1.88 (22H), 1.70 (3H), 2.24-2.58 (8H), 2.67 (1H), 2.75 (3H), 3.00 (1H), 3.40 (1H), 3.51 (2H), 3.68 (1H), 4.48 (1H), 4.76 (1H), 5.00 (1H), 5.04 (1H), 5.18 (1H), 5.55 (1H), 5.71 (1H), 5.98 (1H), 6.68 (2H), 6.98 (2H), 7.07 (2H), 7.37 (1H), 7.76 (1H), 7.96 (1H) ppm.

Example EL35

11-(2,5-Dioxo-2,5-dihydro-pyrrol-1-yl)-undecanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-phenyl ester Analogously to Example EL2, 14 mg (15 µmol) of the compound prepared according to Example EL34 are reacted. After working-up and purification, 6 mg (6 µmol, 42%) of the title compound are isolated.
$^1$H-NMR (CDCl$_3$) von A: δ=1.01 (3H), 1.14 (6H), 1.20-1.90 (26H), 2.12-2.58 (8H), 2.71 (1H), 2.77 (3H), 2.85 (1H), 3.44 (1H), 3.51 (2H), 3.69 (1H), 4.48 (1H), 4.73 (1H), 5.01 (1H), 5.05 (1H), 5.45 (1H), 5.70 (1H), 6.08 (1H), 6.68 (2H), 6.99 (2H), 7.12 (2H), 7.31 (1H), 7.77 (1H), 7.92 (1H) ppm.

Example EL36

4-(2,5-Dioxo-2,5-dihydro-pyrrol-1-yl)-butanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester

Example EL36a 4-(2,5-Dioxo-2,5-dihydro-pyrrol-1-yl)-butanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-phenyl ester Analogously to Example EL12b, 330 mg (470 µmol) of the compound prepared according to Example EL14a are reacted with 544 mg of the compound prepared according to Example L12. After working-up and purification, 170 mg (178 µmol, 38%) of the title compound are isolated.

Example EL36

4-(2,5-Dioxo-2,5-dihydro-pyrrol-1-yl)-butanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester Analogously to Example EL1, 170 mg (178 µmol) of the compound prepared according to Example EL36a are reacted. After working-up and purification, 21 mg (24 µmol, 14%) of the title compound are isolated.
$^1$H-NMR (CDCl$_3$): δ=1.02 (3H), 1.07 (3H), 1.22 (3H), 0.97-2.13 (8H), 1.70 (3H), 2.28-2.63 (8H), 2.84 (3H), 2.82-2.95 (2H), 3.55 (1H), 3.67 (2H), 3.97 (1H), 4.92 (1H), 4.96 (1H), 5.15 (1H), 5.16 (2H), 5.22 (1H), 5.70 (1H), 5.82 (1H), 6.68 (2H), 7.08 (2H), 7.34 (1H), 7.41 (2H), 7.79 (1H), 7.94 (1H) ppm.

Example EL37

4-(2,5-Dioxo-2,5-dihydro-pyrrol-1-yl)-butanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-1-yloxycarbonyloxymethyl]-2-nitro-phenyl ester (A)
and 4-(2,5-Dioxo-2,5-dihydro-pyrrol-1-yl)-butanoic acid 4-(1R,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester (B)

32 mg (38 µmol) of the compound prepared according to Example EL36 are reacted. After working-up and purification, 10.1 mg (12 µmol, 31%) of title compound A as well as 1.2 mg (1.4 µmol, 3.7%) of title compound B are isolated.

$^1$H-NMR (CDCl$_3$) of A: δ=0.96 (3H), 1.04 (3H), 1.24 (3H), 1.29 (3H), 0.90-1.78 (7H), 2.04 (2H), 2.16 (2H), 2.20-2.62 (6H), 2.72 (1H), 2.84 (3H), 3.67 (2H), 3.69 (1H), 4.07 (1H), 4.20 (1H), 4.91 (1H), 4.95 (1H), 5.14 (2H), 5.22 (1H), 5.72 (1H), 6.24 (1H), 6.71 (2H), 7.10 (2H), 7.37 (1H), 7.40 (2H), 7.88 (1H), 7.97 (1H) ppm.

Example EL38

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester

Example EL38a 6-(2,5-Dioxo-2,5-dihydro-pyrrol-1-yl)-hexanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-phenyl ester Analogously to Example EL12b, 450 mg (640 µmol) of the compound prepared according to Example EL14a are reacted with 811 mg of the compound prepared according to Example L13. After working-up and purification, 108 mg (110 µmol, 17%) of the title compound are isolated.

Example EL38

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester 108 mg (110 µmol) of the compound prepared according to Example EL38a in 22 ml dichloromethane are mixed with 1.06 ml (2.74 mmol) of a 20% solution of trifluoroacetic acid in dichloromethane. After 16 hours the mixture is diluted with dichloromethane and poured into a saturated solution of sodium bicarbonate. The mixture is extracted several times with dichloromethane and the combined organic extracts are dried over sodium sulfate. The residue obtained by filtration and removal of the solvent is purified by chromatography on fine silica gel. 64 mg (73 µmmol, 67%) of the title compound are isolated.

$^1$H-NMR (CDCl$_3$): δ=1.02 (3H), 1.07 (3H), 1.16 (3H), 1.70 (3H), 0.98-1.96 (12H), 2.25-2.58 (8H), 2.83 (3H), 2.90 (2H), 3.55 (3H), 3.97 (1H), 4.92 (1H), 4.96 (1H), 5.15 (1H), 5.16 (2H), 5.22 (1H), 5.70 (1H), 5.82 (1H), 6.69 (2H), 7.08 (2H), 7.34 (1H), 7.41 (2H), 7.79 (1H), 7.94 (1H) ppm.

Example EL39

6-(2,5-Dioxo-2,5-dihydro-pyrrol-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester (A) und 6-(2,5-Dioxo-2,5-dihydro-pyrrol-1-yl)-hexanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester (B)

Analogously to Example EL2, 64 mg (73 µmol) of the compound prepared according to Example EL38 are reacted.

After working-up and purification, 25 mg (28 µmol, 39%) of the title compound A as well as 5.4 mg (6.1 µmol, 8.3%) of the title compound B are isolated.

$^1$H-NMR (CDCl$_3$) of A: δ=0.96 (3H), 1.04 (3H), 1.13-1.82 (13H), 1.23 (3H), 1.29 (3H), 2.15 (2H), 2.22-2.64 (6H), 2.71 (1H), 2.84 (3H), 3.54 (2H), 3.69 (1H), 4.08 (1H), 4.20 (1H), 4.91 (1H), 4.95 (1H), 5.14 (2H), 5.22 (1H), 5.72 (1H), 6.24 (1H), 6.69 (2H), 7.07 (2H), 7.37 (1H), 7.40 (2H), 7.82 (1H), 7.97 (1H) ppm.

Example EL40

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester

Example EL40a 11-(2,5-Dioxo-2,5-dihydro-pyrrol-1-yl)-undecanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-phenyl ester Analogously to Example EL12b, 450 mg (640 µmol) of the compound prepared according to Example EL14a are reacted with 992 mg of the compound prepared according to Example L14. After working-up and purification, 67 mg (63 µmol, 10%) of the title compound are isolated.

Example EL40

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenyl ester Analogously to Example EL38, 67 mg (63 µmol) of the compound prepared according to Example EL40a are reacted. After working-up and purification, 23 mg (24 µmol, 38%) of the title compound are isolated.

$^1$H-NMR (CDCl$_3$): δ=1.02 (3H), 1.07 (3H), 1.21 (3H), 1.70 (3H), 0.99-1.81 (21H), 1.91 (1H), 2.27-2.58 (8H), 2.83 (3H), 2.89 (2H), 3.50 (2H), 3.55 (1H), 3.97 (1H), 4.92 (1H), 4.96 (1H), 5.15 (1H), 5.16 (2H), 5.20 (1H), 5.70 (1H), 5.82 (1H), 6.68 (2H), 7.08 (2H), 7.34 (1H), 7.41 (2H), 7.79 (1H), 7.94 (1H) ppm.

Example EL41

11-(2,5-Dioxo-2,5-dihydro-pyrrol-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester (A) and 11-(2,5-Dioxo-2,5-dihydro-pyrrol-1-yl)-undecanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester (B)

Analogously to Example EL2, 33 mg (35 µmol) of the compound prepared according to Example EL40 are reacted.

After working-up and purification, 13 mg (14 µmol, 38%) of the title compound A as well as 4 mg (4 µmol, 12%) of the title compound B are isolated.

$^1$H-NMR (CDCl$_3$) of A: δ=0.96 (3H), 1.04 (3H), 1.23 (3H), 0.91-1.78 (27H), 2.16 (2H), 2.23-2.68 (5H), 2.71 (1H), 2.84 (3H), 3.50 (2H), 3.69 (1H), 4.07 (1H), 4.20 (1H), 4.91 (1H), 4.95 (1H), 5.14 (2H), 5.22 (1H), 5.72 (1H), 6.24 (1H), 6.68 (2H), 7.07 (2H), 7.37 (1H), 7.40 (2H), 7.82 (1H), 7.97 (1H) ppm.

Example EL42

4-(2,5-Dioxo-2,5-dihydro-pyrrol-1-yl)-butanoic acid 4-(4S,7R,8S,9S,13Z,16S)-[7-allyl-8-hydroxy-5,5,9, 13-tetramethyl-16-(2-methyl-benzothiazol-5-yl)-2,6-dioxo-oxacyclohexadec-13-en-4-yloxycarbonyloxymethyl]-2-chlor-phenyl ester Example EL42a 4-(2,5-Dioxo-2,5-dihydro-pyrrol-1-yl)-butanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-chlor-phenyl ester Analogously to Example EL12b, 329 mg (467 µmol) of the compound prepared according to Example EL12a are reacted with 885 mg of the compound prepared according to Example L15. After working-up and purification, 126 mg (127 µmol, 27%) of the title compound are isolated.

Example EL42

4-(2,5-Dioxo-2,5-dihydro-pyrrol-1-yl)-butanoic acid 4-(4S,7R,8S,9S,13Z,16S)-[7-allyl-8-hydroxy-5,5,9, 13-tetramethyl-16-(2-methyl-benzothiazol-5-yl)-2,6-dioxo-oxacyclohexadec-13-en-4-yloxycarbonyloxymethyl]-2-chlor-phenyl ester Analogously to Example EL1, 126 mg (127 µmol) of the compound prepared according to Example EL42a are reacted. After working-up and purification, 79 mg (90 µmol, 71%) of the title compound are isolated.

$^1$H-NMR (CDCl$_3$): δ=1.01 (3H), 1.13 (3H), 1.14 (3H), 1.70 (3H), 1.31-1.72 (17H), 2.75 (3H), 2.99 (1H), 3.40 (1H), 3.68 (3H), 4.49 (1H), 4.70 (1H), 5.00 (1H), 5.05 (1H), 5.18 (1H), 5.55 (1H), 5.71 (1H), 5.98 (1H), 6.72 (2H), 6.99 (1H), 7.07 (1H), 7.10 (1H), 7.36 (1H), 7.75 (1H), 7.95 (1H) ppm.

Example EL43

4-(2,5-Dioxo-2,5-dihydro-pyrrol-1-yl)-butanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-chlor-phenyl ester (A) and 4-(2,5-Dioxo-2,5-dihydro-pyrrol-1-yl)-butanoic acid 4-(1R,3S,7S,10R,11S,12S, 16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-chlor-phenyl ester (B)

Analogously to Example EL2, 66 mg (75 µmol) of the compound prepared according to Example EL42 are reacted. After working-up and purification, 29.4 mg (32.9 µmol, 44%) of the title compound A as well as 9.7 mg (10.9 µmol, 14%) of the title compound B are isolated.

$^1$H-NMR (CDCl$_3$) of A: δ=1.03 (3H), 1.13 (3H), 1.15 (3H), 1.23 (1H), 1.31 (3H), 1.34-2.74 (17H), 2.78 (3H), 2.86 (1H), 3.44 (1H), 3.67 (3H), 4.46 (1H), 4.67 (1H), 5.01 (1H), 5.05 (1H), 5.46 (1H), 5.70 (1H), 6.08 (1H), 6.72 (2H), 7.01 (1H), 7.08 (1H), 7.16 (1H), 7.31 (1H), 7.77 (1H), 7.92 (1H) ppm.

Example EL44

6-(2,5-Dioxo-2,5-dihydro-pyrrol-1-yl)-hexanoic acid 4-(4S,7R,8S,9S,13Z,16S)-[7-allyl-8-hydroxy-5,5,9, 13-tetramethyl-16-(2-methyl-benzothiazol-5-yl)-2,6-dioxo-oxacyclohexadec-13-en-4-yloxycarbonyloxymethyl]-2-chloro-phenyl ester Example EL44a 6-(2,5-Dioxo-2,5-dihydro-pyrrol-1-yl)-hexanoic acid 4-(4S,7R,8S,9S,13Z,16S)-[7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-chloro-phenyl ester Analogously to Example EL12b, 329 mg (467 µmol) of the compound prepared according to Example EL12a are reacted with 821 mg of the compound prepared according to Example L16. After working-up and purification, 120 mg (118 µmol, 25%) of the title compound are isolated.

Example EL44

6-(2,5-Dioxo-2,5-dihydro-pyrrol-1-yl)-hexanoic acid 4-(4S,7R,8S,9S,13Z,16S)-[7-allyl-8-hydroxy-5,5,9, 13-tetramethyl-16-(2-methyl-benzothiazol-5-yl)-2,6-dioxo-oxacyclohexadec-13-en-4-yloxycarbonyloxymethyl]-2-chloro-phenyl ester Analogously to Example EL1, 120 mg (118 µmol) of the compound prepared according to Example EL44a are reacted. After working-up and purification, 60 mg (66 µmol, 56%) of the title compound are isolated.

$^1$H-NMR (CDCl$_3$): δ=1.01 (3H), 1.05 (1H), 1.13 (3H), 1.14 (3H), 1.33-1.89 (12H), 1.71 (3H), 2.24-2.70 (8H), 2.74 (3H), 3.00 (1H), 3.40 (1H), 3.55 (2H), 3.69 (1H), 4.49 (1H), 4.71 (1H), 5.00 (1H), 5.05 (1H), 5.18 (1H), 5.56 (1H), 5.71 (1H), 5.99 (1H), 6.70 (2H), 6.95 (1H), 7.03 (1H), 7.11 (1H), 7.37 (1H), 7.75 (1H), 7.95 (1H), ppm.

Example EL45

6-(2,5-Dioxo-2,5-dihydro-pyrrol-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-chlor-phenyl ester (A) and 6-(2,5-Dioxo-2,5-dihydro-pyrrol-1-yl)-hexanoic acid 4-(1R,3S,7S,10R,11S,12S,16S)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-chloro-phenyl ester (B)

Analogously to Example EL2, 60 mg (66 µmol) of the compound prepared according to Example EL44 is reacted.

After working-up and purification, 32 mg (34.7 μmol, 53%) of the title compound A as well as 11 mg (11.9 μmol, 18%) of the title compound B are isolated.

$^1$H-NMR (CDCl$_3$) von A: δ=1.02 (3H), 1.14 (3H), 1.15 (3H), 1.24 (1H), 1.32 (3H), 1.34-2.74 (21H), 2.77 (3H), 2.86 (1H), 3.44 (1H), 3.55 (2H), 3.69 (1H), 4.46 (1H), 4.67 (1H), 5.01 (1H), 5.05 (1H), 5.46 (1H), 5.70 (1H), 6.09 (1H), 6.69 (2H), 6.99 (1H), 7.04 (1H), 7.16 (1H), 7.32 (1H), 7.77 (1H), 7.92 (1H) ppm.

Example EL46

11-(2,5-Dioxo-2,5-dihydro-pyrrol-1-yl)-undecanoic acid 4-(4S,7R,8S,9S,13Z,16S)-[7-allyl-8-hydroxy-5, 5,9,13-tetramethyl-16-(2-methyl-benzothiazol-5-yl)- 2,6-dioxo-oxacyclohexadec-13-en-4-yloxycarbony- loxymethyl]-2-chloro-phenyl ester Example EL46a 11-(2,5-Dioxo-2,5-dihydro-pyrrol-1-yl)-undecanoic acid 4-(4S,7R,8S,9S,13Z,16S)-[7-allyl-8-(tert-butyl- dimethyl-silanyloxy)-5,5,9,13-tetramethyl-16-(2- methyl-benzothiazol-5-yl)-2,6-dioxo-oxacyclohexa- dec-13-en-4-yloxycarbonyloxymethyl]-2-chloro- phenyl ester Analogously to Example EL12b, 323 mg (459 μmol) of the compound prepared according to Example EL12a are reacted with 790 mg of the compound prepared according to Example L17. After working-up and purification, 96 mg (88 μmol, 19%) of the title compound are isolated.

Example EL46

11-(2,5-Dioxo-2,5-dihydro-pyrrol-1-yl)-undecanoic acid 4-(4S,7R,8S,9S,13Z,16S)-[7-allyl-8-hydroxy-5, 5,9,13-tetramethyl-16-(2-methyl-benzothiazol-5-yl)- 2,6-dioxo-oxacyclohexadec-13-en-4-yloxycarbony- loxymethyl]-2-chlor-phenyl ester Analogously to Example EL1, 59 mg (54 μmol) of the compound prepared according to Example EL46a are reacted. After working-up and purification, 27 mg (27.7 μmol, 51%) of the title compound are isolated.

$^1$H-NMR (CDCl$_3$): δ=1.01 (3H), 1.13 (3H), 1.15 (3H), 1.23-2.70 (31H), 1.71 (3H), 2.74 (3H), 2.99 (1H), 3.40 (1H), 3.51 (2H), 3.68 (1H), 4.49 (1H), 4.70 (1H), 5.00 (1H), 5.04 (1H), 5.18 (1H), 5.56 (1H), 5.71 (1H), 5.99 (1H), 6.68 (2H), 6.95 (1H), 7.03 (1H), 7.11 (1H), 7.36 (1H), 7.75 (1H), 7.95 (1H) ppm.

Example EL47

11-(2,5-Dioxo-2,5-dihydro-pyrrol-1-yl)-undecanoic acid 4-(1S,3S,7S,10R,11S,12S,16R)-[10-allyl-11- hydroxy-8,8,12,16-tetramethyl-3-(2-methyl-ben- zothiazol-5-yl)-5,9-dioxo-4,17-dioxa-bicyclo[14.1.0] heptadec-7-yloxycarbonyloxymethyl]-2-chloro- phenyl ester (A) and 11-(2,5-Dioxo-2,5-dihydro- pyrrol-1-yl)-undecanoic acid 4-(1R,3S,7S,10R,11S, 12S,16S)-[10-allyl-11-hydroxy-8,8,12,16- tetramethyl-3-(2-methyl-benzothiazol-5-yl)-5,9- dioxo-4,17-dioxa-bicyclo[14.1.0]heptadec-7- yloxycarbonyloxymethyl]-2-chloro-phenyl ester (B)

Analogously to Example EL2, 27 mg (27 μmol) of the compound prepared according to Example EL46 are reacted. After working-up and purification, 14 mg (14.1 μmol, 52%) of the title compound A as well as 5 mg (5.0 μmol, 19%) of the title compound B are isolated.

$^1$H-NMR (CDCl$_3$) of A: δ=1.02 (3H), 1.13 (3H), 1.15 (3H), 1.19-1.84 (27H), 2.09-2.74 (8H), 2.77 (3H), 2.85 (1H), 3.44 (1H), 3.50 (2H), 3.69 (1H), 4.46 (1H), 4.67 (1H), 5.01 (1H), 5.06 (1H), 5.45 (1H), 5.70 (1H), 6.08 (1H), 6.68 (2H), 6.99 (1H), 7.04 (1H), 7.16 (1H), 7.31 (1H), 7.76 (1H), 7.91 (1H) ppm.

Example EL48

4-(2,5-Dioxo-2,5-dihydro-pyrrol-1-yl)-butanoic acid 4-(4S,7R,8S,9S,13Z,16S)-[7-allyl-4-hydroxy-5,5,9, 13-tetramethyl-16-(2-methyl-benzothiazol-5-yl)-2,6- dioxo-oxacyclohexadec-13-en-8-yloxycarbony- loxymethyl]-2-chloro-phenyl ester Example EL48a 4-(2,5-Dioxo-2,5-dihydro-pyrrol-1-yl)-butanoic acid 4-(4S,7R,8S,9S,13Z,16S)-[7-allyl-4-(tert-butyl-dim- ethyl-silanyloxy)-5,5,9,13-tetramethyl-16-(2-methyl- benzothiazol-5-yl)-2,6-dioxo-oxacyclohexadec-13- en-8-yloxycarbonyloxymethyl]-2-chloro-phenyl ester Analogously to Example EL12b, 340 mg (482 μmol) of the compound prepared according to Example EL14a are reacted with 885 mg of the compound prepared according to Example L15. After working-up and purification, 151 mg (152 μmol, 32%) of the title compound are isolated.

Example EL48

4-(2,5-Dioxo-2,5-dihydro-pyrrol-1-yl)-butanoic acid 4-(4S,7R,8S,9S,13Z,16S)-[7-allyl-4-hydroxy-5,5,9, 13-tetramethyl-16-(2-methyl-benzothiazol-5-yl)-2,6- dioxo-oxacyclohexadec-13-en-8-yloxycarbony- loxymethyl]-2-chloro-phenyl ester Analogously to Example EL1, 151 mg (152 μmol) of the compound prepared according to Example EL48a are reacted. After working-up and purification, 46 mg (52 μmol, 34%) of the title compound are isolated.

$^1$H-NMR (CDCl$_3$): δ=1.02 (3H), 1.07 (3H), 1.26 (3H), 1.71 (3H), 1.15-2.44 (13H), 2.51 (2H), 2.65 (2H), 2.84 (3H), 2.91 (1H), 3.55 (1H), 3.68 (2H), 3.99 (1H), 4.92 (1H), 4.98 (1H), 5.06-5.25 (4H), 5.70 (1H), 5.83 (1H), 6.72 (2H), 7.17 (1H), 7.31 (1H), 7.34 (1H), 7.49 (1H), 7.80 (1H), 7.96 (1H) ppm.

Example EL49

4-(2,5-Dioxo-2,5-dihydro-pyrrol-1-yl)-butanoic acid 4-(1S,3S,7S,10R,11S,12S,16R)-[10-allyl-7-hydroxy- 8,8,12,16-tetramethyl-3-(2-methyl-benzothiazol-5- yl)-5,9-dioxo-4,17-dioxa-bicyclo [14.1.0]heptadec- 11-yloxycarbonyloxymethyl]-2-chloro-phenyl ester (A) and 4-(2,5-Dioxo-2,5-dihydro-pyrrol-1-yl)-bu- tanoic acid 4-(1R,3S,7S,10R,11S,12S,16S)-[10- allyl-7-hydroxy-8,8,12,16-tetramethyl-3-(2-methyl- benzothiazol-5-yl)-5,9-dioxo-4,17-dioxa-bicyclo [14.1.0]heptadec-11-yloxycarbonyloxymethyl]-2- chloro-phenyl ester (B)

Analogously to Example EL2, 46 mg (52 μmol) of the compound prepared according to Example EL48 are reacted.

After working-up and purification, 6 mg (6.7 µmol, 13%) of the title compound A as well as 1 mg (1.1 µmol, 2%) of the title compound B are isolated.

$^1$H-NMR (CDCl$_3$) of A: δ=0.97 (3H), 1.04 (3H), 1.24 (3H), 1.30 (3H), 1.14-2.76 (21H), 2.85 (3H), 3.68 (3H), 4.09 (1H), 4.23 (1H), 4.91 (1H), 4.97 (1H), 5.11 (2H), 5.22 (1H), 5.72 (1H), 6.25 (1H), 6.72 (2H), 7.16 (1H), 7.30 (1H), 7.37 (1H), 7.48 (1H), 7.83 (1H), 7.99 (1H) ppm.

Example EL50

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester

Example EL50a 6-(2,5-Dioxo-2,5-dihydro-pyrrol-1-yl)-hexanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester Analogously to Example EL12b, 340 mg (482 µmol) of the compound prepared according to Example EL14a are reacted with 848 mg of the compound prepared according to Example L16. After working-up and purification, 158 mg (155 µmol, 32%) of the title compound are isolated.

Example EL50

6-(2,5-Dioxo-2,5-dihydro-pyrrol-1-yl)-hexanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester Analogously to Example EL1, 158 mg (155 µmol) of the compound prepared according to Example EL50a are reacted. After working-up and purification, 58 mg (64 µmol, 41%) of the title compound are isolated.

$^1$H-NMR (CDCl$_3$): δ=1.02 (3H), 1.08 (3H), 1.22 (3H), 1.71 (3H), 0.90-2.45 (17H), 2.51 (2H), 2.61 (2H), 2.83 (3H), 2.88 (1H), 3.55 (3H), 3.97 (1H), 4.92 (1H), 4.98 (1H), 5.10-5.25 (4H), 5.71 (1H), 5.83 (1H), 6.69 (2H), 7.12 (1H), 7.30 (1H), 7.34 (1H), 7.49 (1H), 7.79 (1H), 7.95 (1H) ppm.

Example EL51

6-(2,5-Dioxo-2,5-dihydro-pyrrol-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chloro-phenyl ester (A) and 6-(2,5-Dioxo-2,5-dihydro-pyrrol-1-yl)-hexanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chloro-phenyl ester (B)

Analogously to Example EL2, 58 mg (64 µmol) of the compound prepared according to Example EL50 are reacted. After working-up and purification, 25 mg (27 µmol, 42%) of the title compound A as well as 7 mg (7.6 µmol, 12%) of the title compound B are isolated.

$^1$H-NMR (CDCl$_3$) of A: δ=0.97 (3H), 1.04 (3H), 1.24 (3H), 1.31 (3H), 1.12-2.65 (21H), 2.72 (1H), 2.84 (3H), 3.55 (2H), 3.71 (1H), 4.08 (1H), 4.22 (1H), 4.91 (1H), 4.96 (1H), 5.12 (2H), 5.23 (1H), 5.72 (1H), 6.24 (1H), 6.69 (2H), 7.13 (1H), 7.30 (1H), 7.37 (1H), 7.48 (1H), 7.83 (1H), 7.97 (1H) ppm.

Example EL52

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester

Example EL52a 11-(2,5-Dioxo-2,5-dihydro-pyrrol-1-yl)-undecanoic acid 4-(4S,7R,8S,9S,13Z,16S)-[7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester Analogously to Example EL12b, 355 mg (476 µmol) of the compound prepared according to Example EL14a are reacted with 790 mg of the compound prepared according to Example L17. After working-up and purification, 122 mg (112 µmol, 24%) of the title compound are isolated.

Example EL52

11-(2,5-Dioxo-2,5-dihydro-pyrrol-1-yl)-undecanoic acid 4-(4S,7R,8S,9S,13Z,16S)-[7-allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenyl ester Analogously to Example EL1, 122 mg (112 µmol) of the compound prepared according to Example EL52a are reacted. After working-up and purification, 28 mg (29 µmol, 26%) of the title compound are isolated.

$^1$H-NMR (CDCl$_3$): δ=1.02 (3H), 1.08 (3H), 1.22 (3H), 1.11-2.48 (26H), 1.71 (3H), 2.51 (2H), 2.61 (2H), 2.83 (3H), 2.89 (1H), 3.46-3.58 (3H), 3.98 (1H), 4.61 (2H), 4.92 (1H), 4.98 (1H), 5.11-5.25 (3H), 5.70 (1H), 5.83 (1H), 6.68 (2H), 7.00 (1H), 7.18 (1H), 7.29 (1H), 7.36 (1H), 7.79 (1H), 7.95 (1H) ppm.

Example EL53

11-(2,5-Dioxo-2,5-dihydro-pyrrol-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chloro-phenyl ester (A) and 11-(2,5-Dioxo-2,5-dihydro-pyrrol-1-yl)-undecanoic acid 4-(1R,3S,7S,10R,11S,12S,16S)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chloro-phenyl ester (B)

Analogously to Example EL2, 28 mg (29 µmol) of the compound prepared according to Example EL52 are reacted.

After working-up and purification, 6.2 mg (6.3 µmol, 22%) of the title compound A as well as 0.3 mg (0.3 µmol, 1%) of the title compound B are isolated.

$^1$H-NMR (CDCl$_3$) of A: δ=0.97 (3H), 1.04 (3H), 1.23 (3H), 0.82-1.83 (25H), 2.16 (2H), 2.24-2.65 (7H), 2.72 (1H), 2.84 (3H), 3.50 (2H), 3.70 (1H), 4.08 (1H), 4.21 (1H), 4.92 (1H), 4.97 (1H), 5.11 (2H), 5.22 (1H), 5.72 (1H), 6.25 (1H), 6.67 (2H), 7.12 (1H), 7.30 (1H), 7.37 (1H), 7.49 (1H), 7.83 (1H), 7.98 (1H) ppm.

Example EL54

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[4-(2,5-dioxo-2,5-dihydro-pyrrol-1-yl)-3-nitro-butyrylamino]-benzyl ester

Example EL54a (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 4-amino-benzyl ester Analogously to Example EL12b, 160 mg (227 µmol) of the compound prepared according to Example EL12a are reacted with 191 mg (4-amino-3-nitro-phenyl)-methanol. After working-up and purification, 51 mg (61 µmol, 27%) of the title compound are isolated.

$^1$H-NMR (CDCl$_3$): δ=0.07 (3H), 0.12 (3H), 0.92 (9H), 0.99 (3H), 1.03 (3H), 1.23 (3H), 0.85-1.74 (8H), 1.93 (1H), 2.28 (1H), 2.38 (2H), 2.49 (1H), 2.66 (1H), 2.77 (3H), 2.82 (1H), 2.97 (1H), 3.22 (1H), 3.87 (1H), 4.85-5.03 (4H), 5.22 (1H), 5.42 (1H), 5.74 (1H), 5.89 (1H), 6.10 (2H), 6.68 (1H), 7.19 (1H), 7.32 (1H), 7.73 (1H), 7.90 (1H), 7.98 (1H) ppm.

Example EL54b (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 4-[4-(2,5-dioxo-2,5-dihydro-pyrrol-1-yl)-butyrylamino]-3-nitro-benzyl ester 153 mg (837 µmol) of the compound prepared according to Example L4 are mixed with 1.82 ml thionyl chloride and refluxed for 3.5 hours. The mixture is diluted with toluene and evaporated. A solution of 130 mg (156 µmol) of the compound prepared according to Example 54a in 6 ml dichloromethane is added, 75 µl pyridine are admixed, and the mixture is stirred at 23° C. for 16 hours. It is poured into water, extracted several times with dichloromethane, the combined organic extracts are washed with water and dried over sodium sulfate. After filtration and removal of the solvent, the residue is purified by chromatography. 101 mg (101 µmol, 65%) of the title compound are isolated.

Example EL54

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[4-(2,5-dioxo-2,5-dihydro-pyrrol-1-yl)-butyrylamino]-3-nitro-benzyl ester Analogously to Example EL1, 101 mg (101 µmol) of the compound prepared according to Example EL54a are reacted. After working-up and purification, 62 mg (70 µmol, 69%) of the title compound are isolated.

$^1$H-NMR (CDCl$_3$): δ=1.01 (3H), 1.14 (6H), 1.39 (2H), 1.64 (2H), 1.71 (3H), 1.80 (2H), 2.07 (2H), 2.23-2.54 (8H), 2.69 (1H), 2.77 (3H), 2.96 (1H), 3.39 (1H), 3.65 (2H), 3.69 (1H), 4.52 (1H), 4.75 (1H), 5.00 (1H), 5.05 (1H), 5.18 (1H), 5.55 (1H), 5.71 (1H), 5.98 (1H), 6.71 (2H), 7.31 (1H), 7.36 (1H), 7.77 (1H), 7.91 (1H), 7.93 (1H), 8.67 (1H), 10.28 (1H) ppm.

Example EL55

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[4-(2,5-dioxo-2,5-dihydro-pyrrol-1-yl)-butyrylamino]-3-nitro-benzyl ester (A) and (1R,3S,7S,10R,11S,12S,16S)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[4-(2,5-dioxo-2,5-dihydro-pyrrol-1-yl)-butyrylamino]-3-nitro-benzyl ester (B)

Analogously to Example EL2, 62 mg (70 µmol) of the compound prepared according to Example EL54 are reacted. After working-up and purification, 38 mg (42 µmol, 60%) of the title compound A as well as 11 mg (12 µmol, 17%) of the title compound B are isolated.

$^1$H-NMR (CDCl$_3$) of A: δ=1.03 (3H), 1.13 (3H), 1.17 (3H), 1.32 (3H), 1.20-2.58 (17H), 2.70 (1H), 2.79 (3H), 2.85 (1H), 3.43 (1H), 3.65 (2H), 3.69 (1H), 4.52 (1H), 4.72 (1H), 5.01 (1H), 5.05 (1H), 5.45 (1H), 5.70 (1H), 6.07 (1H), 6.71 (2H), 7.31 (1H), 7.35 (1H), 7.78 (1H), 7.88 (1H), 7.95 (1H), 8.68 (1H), 10.28 (1H) ppm.

Example EL56

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[6-(2,5-dioxo-2,5-dihydro-pyrrol-1-yl)-hexanoylamino]-3-nitro-benzyl ester

Example EL56a (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 4-[6-(2,5-dioxo-2,5-dihydro-pyrrol-1-yl)-hexanoylamino]-3-nitro-benzyl ester Analogously to Example EL54b, 50 mg (60 µmol) of the compound prepared according to Example EL54a are reacted with the compound prepared according to Example L5. After working-up and purification, 58 mg (56 µmol, 94%) of the title compound are isolated.

Example EL56

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[6-(2,5-dioxo-2,5-dihydro-pyrrol-1-yl)-hexanoylamino]-3-nitro-benzyl ester Analogously to Example EL1, 82 mg (80 µmol) of the compound prepared according to Example EL56a are reacted. After working-up and purification, 34 mg (37 µmol, 46%) of the title compound are isolated.

¹H-NMR (CDCl₃): δ=1.01 (3H), 1.14 (6H), 1.70 (3H), 1.31-2.57 (20H), 2.69 (1H), 2.78 (3H), 2.97 (1H), 3.39 (1H), 3.54 (2H), 3.69 (1H), 4.51 (1H), 4.74 (1H), 5.00 (1H), 5.05 (1H), 5.18 (1H), 5.55 (1H), 5.78 (1H), 5.98 (1H), 6.69 (2H), 7.31 (1H), 7.36 (1H), 7.76 (1H), 7.92 (1H), 7.93 (1H), 8.71 (1H), 10.32 (1H) ppm.

Example EL57

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[6-(2,5-dioxo-2,5-dihydro-pyrrol-1-yl)-hexanoylamino]-3-nitro-benzyl ester (A) and (1R,3S,7S,10R,11S,12S,16S)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[6-(2,5-dioxo-2,5-dihydro-pyrrol-1-yl)-hexanoylamino]-3-nitro-benzyl ester (B)

Analogously to Example EL2, 34 mg (37 µmol) of the compound prepared according to Example EL56 are reacted. After working-up and purification, 19 mg (20.4 µmol, 55%) of the title compound A as well as 6 mg (6.4 µmol, 17%) of the title compound B are isolated.

¹H-NMR (CDCl₃) of A: δ=1.02 (3H), 1.14 (3H), 1.15 (3H), 1.39 (2H), 1.70 (3H), 1.65 (2H), 1.80 (2H), 2.06 (2H), 2.23-2.55 (8H), 2.69 (1H), 2.77 (3H), 2.97 (1H), 3.39 (1H), 3.65 (2H), 3.69 (1H), 4.52 (1H), 4.75 (1H), 5.00 (1H), 5.05 (1H), 5.18 (1H), 5.55 (1H), 5.71 (1H), 5.97 (1H), 6.71 (2H), 7.31 (1H), 7.36 (1H), 7.76 (1H), 7.91 (1H), 7.93 (1H), 8.68 (1H), 10.28 (1H) ppm.

Example EL58

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[11-(2,5-dioxo-2,5-dihydro-pyrrol-1-yl)-undecanoylamino]-3-nitro-benzyl ester Example EL58a (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 4-[11-(2,5-dioxo-2,5-dihydro-pyrrol-1-yl)-undecanoylamino]-3-nitro-benzyl ester Analogously to Example EL54b, 130 mg (156 µmol) of the compound prepared according to Example EL54a are reacted with the compound prepared according to Example L6. After working-up and purification, 120 mg (109 µmol, 70%) of the title compound are isolated.

Example EL58

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 4-[11-(2,5-dioxo-2,5-dihydro-pyrrol-1-yl)-undecanoylamino]-3-nitro-benzyl ester Analogously to Example EL1, 120 mg (109 µmol) of the compound prepared according to Example EL58a are reacted. After working-up and purification, 89 mg (90 µmol, 83%) of the title compound are isolated.

¹H-NMR (CDCl₃): δ=1.01 (3H), 1.13 (3H), 1.14 (3H), 1.70 (3H), 1.04-2.56 (30H), 2.69 (1H), 2.78 (3H), 2.97 (1H), 3.39 (1H), 3.50 (2H), 3.69 (1H), 4.52 (1H), 4.74 (1H), 5.01 (1H), 5.05 (1H), 5.18 (1H), 5.55 (1H), 5.71 (1H), 5.97 (1H), 6.67 (2H), 7.31 (1H), 7.36 (1H), 7.76 (1H), 7.91 (1H), 7.93 (1H), 8.72 (1H), 10.33 (1H) ppm.

Example EL59

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[11-(2,5-dioxo-2,5-dihydro-pyrrol-1-yl)-undecanoylamino]-3-nitro-benzyl ester (A) and (1R,3S,7S,10R,11S,12S,16S)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[11-(2,5-dioxo-2,5-dihydro-pyrrol-1-yl)-undecanoylamino]-3-nitro-benzyl ester (B)

Analogously to Example EL2, 89 mg (90 µmol) of the compound prepared according to Example EL58 are reacted. After working-up and purification, 45 mg (µmol, %) of the title compound A as well as 15 mg (µmol, %) of the title compound B are isolated.

¹H-NMR (CDCl₃) of A: δ=1.03 (3H), 1.13 (3H), 1.16 (3H), 1.20-1.83 (26H), 2.09-2.57 (8H), 2.72 (1H), 2.79 (3H), 2.86 (1H), 3.44 (1H), 3.50 (2H), 3.69 (1H), 4.51 (1H), 4.72 (1H), 5.01 (1H), 5.05 (1H), 5.45 (1H), 5.71 (1H), 6.08 (1H), 6.68 (2H), 7.32 (1H), 7.35 (1H), 7.78 (1H), 7.88 (1H), 7.96 (1H), 8.73 (1H), 10.33 (1H) ppm.

Example EL60

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 6-(2,5-dioxo-2,5-dihydro-pyrrol-1-yl)-hexyl ester Example EL60a (4S,7R,8S,9S,13Z,16S)-Carbonic acid 7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester 6-(2,5-dioxo-2,5-dihydro-pyrrol-1-yl)-hexyl ester Analogously to Example EL12b, 1.25 g (1.77 mmol) of the compound prepared according to Example EL12a are reacted with 1.75 g of the compound prepared according to L18. After working-up and purification, 119 mg (138 µmol, 8%) of the title compound are isolated.

Example EL60

(4S,7R,8S,9S,13Z,16S)-Carbonic acid 7-allyl-8-hydroxy-5,5,9,13-tetramethyl-16-(2-methyl-benzothiazol-5-yl)-2,6-dioxo-oxacyclohexadec-13-en-4-yl ester 6-(2,5-dioxo-2,5-dihydro-pyrrol-1-yl)-hexyl ester Analogously to Example EL1, 101 mg (117 µmol) of the compound prepared according to Example EL60a are reacted. After working-up and purification, 68 mg (91 µmol, 77%) of the title compound are isolated.

¹H-NMR (CDCl₃): δ=1.02 (3H), 1.12-1.87 (19H), 1.70 (3H), 2.23-2.56 (6H), 2.66 (1H), 2.83 (3H), 2.97 (1H), 3.40 (2H), 3.48 (2H), 3.68 (1H), 3.75 (1H), 5.01 (1H), 5.05 (1H), 5.17 (2H), 5.51 (1H), 5.72 (1H), 5.97 (1H), 6.68 (2H), 7.35 (1H), 7.78 (1H), 7.92 (1H) ppm.

Example EL61

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo [14.1.0]heptadec-7-yl ester 6-(2,5-dioxo-2,5-dihydro-pyrrol-1-yl)-hexyl ester (A) and (1R,3S,7S, 10R,11S,12S,16S)-Carbonic acid 10-allyl-11-hydroxy-8,8,12,16-tetramethyl-3-(2-methyl-benzothiazol-5-yl)-5,9-dioxo-4,17-dioxa-bicyclo [14.1.0]heptadec-7-yl ester 6-(2,5-dioxo-2,5-dihydro-pyrrol-1-yl)-hexyl ester (B)

Analogously to Example EL2, 68 mg (91 μmol) of the compound prepared according to Example EL60 are reacted. After working-up and purification, 26 mg (34 μmol, 37%) of the title compound A as well as 10 mg (13 μmol, 14%) of the title compound B are isolated.

¹H-NMR (CDCl₃) of A: δ=1.03 (3H), 1.14 (3H), 1.18 (3H), 1.32 (3H), 1.10-1.85 (15H), 2.11-2.43 (5H), 2.52 (1H), 2.70 (1H), 2.84 (3H), 2.86 (1H), 3.38-3.51 (4H), 3.69 (1H), 3.74 (1H), 5.01 (1H), 5.05 (1H), 5.42 (1H), 5.72 (1H), 6.07 (1H), 6.69 (2H), 7.32 (1H), 7.80 (1H), 7.90 (1H) ppm.

Example EL62

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-butyrylamino]-benzyl ester Example EL62a (4S,7R,8S,9S,13Z,16S)-Carbonic acid 7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester 4-amino-benzyl ester Analogously to Example EL12b, 1.73 g (2.46 mmol) of the compound prepared according to Example EL14a are reacted with 2.06 g (4-amino-3-nitro-phenyl)-methanol. After working-up and purification, 420 mg (502 μmol, 20%) of the title compound are isolated.

¹H-NMR (CDCl₃): δ=−0.10 (3H), 0.09 (3H), 0.84 (9H), 0.96-1.21 (2H), 1.01 (3H), 1.12 (3H), 1.15 (3H), 1.70 (3H), 1.61-1.85 (4H), 2.11 (1H), 2.29 (2H), 2.54-2.78 (3H), 2.83 (3H), 2.90 (1H), 3.31 (1H), 3.93 (1H), 4.86 (1H), 4.96 (1H), 5.04 (1H), 5.11 (1H), 5.25 (2H), 5.55 (1H), 5.72 (1H), 6.14 (2H), 6.82 (1H), 7.35 (1H), 7.43 (1H), 7.79 (1H), 7.91 (1H), 8.18 (1H) ppm.

Example EL62b (4S,7R,8S,9S,13Z,16S)-Carbonic acid 7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester 4-[4-(2,5-dioxo-2, 5-dihydro-pyrrol-1-yl)-butyrylamino]-3-nitro-benzyl ester Analogously to Example EL54b, 140 mg (167 μmol) of the compound prepared according to Example EL62a are reacted with the compound prepared according to Example L4. After working-up and purification, 150 mg (150 μmol, 90%) of the title compound are isolated.

Example EL62

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-butyrylamino]-benzyl ester Analogously to Example EL1, 145 mg (145 μmol) of the compound prepared according to Example EL62a are reacted. After working-up and purification, 67 mg (76 μmol, 52%) of the title compound are isolated.

¹H-NMR (CDCl₃): δ=1.02 (3H), 1.08 (3H), 1.22 (3H), 1.70 (3H), 1.09-2.12 (8H), 2.27-2.55 (8H), 2.83 (3H), 2.87 (2H), 3.56 (1H), 3.65 (2H), 3.99 (1H), 4.93 (1H), 4.98 (1H), 5.12-5.26 (4H), 5.71 (1H), 5.83 (1H), 6.70 (2H), 7.33 (1H), 7.67 (1H), 7.79 (1H), 7.94 (1H), 8.25 (1H), 8.79 (1H), 10.32 (1H) ppm.

Example EL63

(1S,3S,7S,10R,11S,12S,16R)-Carbonic acid 10-allyl-7-hydroxy-8,8,12,16-tetramethyl-3-(2-methyl-benzothiazol-5-yl)-5,9-dioxo-4,17-dioxa-bicyclo [14.1.0]heptadec-11-yl ester 4-[4-(2,5-dioxo-2,5-dihydro-pyrrol-1-yl)-butyrylamino]-3-nitro-benzyl ester (A) and (1R,3S,7S,10R,11S,12S,16S)-Carbonic acid 10-allyl-7-hydroxy-8,8,12,16-tetramethyl-3-(2-methyl-benzothiazol-5-yl)-5,9-dioxo-4,17-dioxa-bicyclo [14.1.0]heptadec-11-yl ester 4-[4-(2,5-dioxo-2,5-dihydro-pyrrol-1-yl)-butyrylamino]-3-nitro-benzyl ester (B)

Analogously to Example EL2, 67 mg (76 μmol) of the compound prepared according to Example EL62 are reacted. After working-up and purification, 37 mg (41 μmol, 54%) of the title compound A as well as 12 mg (13 μmol, 18%) of the title compound B are isolated.

Example EL64

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-hexanoylamino]-benzyl ester Example EL64a (4S,7R,8S,9S,13Z,16S)-Carbonic acid 7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester 4-[4-(2,5-dioxo-2, 5-dihydro-pyrrol-1-yl)- hexanoylamino]-3-nitro-benzyl ester Analogously to Example EL54b, 140 mg (167 μmol) of the compound prepared according to Example EL62a are reacted with the compound prepared according to Example L5. After working-up and purification, 155 mg (150 μmol, 90%) of the title compound are isolated.

Example EL64

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-hexanoylamino]-benzyl ester Analogously to Example EL1, 150 mg (151 mol) of the compound prepared according to Example EL64a are reacted. After working-up and purification, 68 mg (74 μmol, 49%) of the title compound are isolated.

$^1$H-NMR (CDCl$_3$): δ=1.02 (3H), 1.07 (3H), 1.23 (3H), 1.70 (3H), 1.16-2.54 (20H), 2.84 (3H), 2.87 (2H), 3.54 (3H), 3.98 (1H), 4.92 (1H), 4.98 (1H), 5.13-5.26 (4H), 5.71 (1H), 5.83 (1H), 6.68 (2H), 7.33 (1H), 7.67 (1H), 7.79 (1H), 7.94 (1H), 8.26 (1H), 8.82 (1H), 10.37 (1H) ppm.58

Example EL65

(1S,3S,7S,10R,11S,12S,16R)-Carbonic acid 10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-[4-(2,5-dioxo-2,5-dihydro-pyrrol-1-yl)-hexanoylamino]-3-nitro-benzyl ester (A) and (1R,3S,7S,10R,11S,12S,16S)-Carbonic acid 10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-[4-(2,5-dioxo-2,5-dihydro-pyrrol-1-yl)-hexanoylamino]-3-nitro-benzyl ester (B)

Analogously to Example EL2, 68 mg (74 μmol) of the compound prepared according to Example EL64 are reacted. After working-up and purification, 44 mg (47 μmol, 64%) of the title compound A as well as 3 mg (3 μmol, 4%) of the title compound B are isolated.

Example EL66

(4S,7R,8S,9S,13Z,16S)-Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-undecanoylamino]-benzyl ester

Example EL66a (4S,7R,8S,9S,13Z,16S)-Carbonic acid 7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-undecanoylamino]-3-nitro-benzyl ester Analogously to Example EL54b, 140 mg (167 μmol) of the compound prepared according to Example EL62a are reacted with the compound prepared according to Example L6. After working-up and purification, 165 mg (150 μmol, 90%) of the title compound are isolated.

Example EL66

(4S,7R,8S,9S,13Z,16S) Carbonic acid 7-allyl-4-hydroxy-5,5,9,13-tetramethyl-16-(2-methyl-benzothiazol-5-yl)-2,6-dioxo-oxacyclohexadec-13-en-8-yl ester 4-[4-(2,5-dioxo-2,5-dihydro-pyrrol-1-yl)-3-nitro-undecanoylamino]-benzyl ester Analogously to Example EL1, 145 mg (132 μmol) of the compound prepared according to Example EL66a are reacted. After working-up and purification, 106 mg (108 μmol, 82%) of the title compound are isolated.

$^1$H-NMR (CDCl$_3$): δ=1.01 (3H), 1.06 (3H), 1.24 (3H), 1.70 (3H), 1.14-2.57 (30H), 2.82 (3H), 2.89 (2H), 3.50 (2H), 3.55 (1H), 4.01 (1H), 4.92 (1H), 4.99 (1H), 5.11-5.28 (4H), 5.70 (1H), 5.83 (1H), 6.69 (2H), 7.34 (1H), 7.67 (1H), 7.79 (1H), 7.96 (1H), 8.26 (1H), 8.85 (1H), 10.38 (1H) ppm.

Example EL67

(1S,3S,7S,10R,11S,12S,16R)-Carbonic acid 10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-[4-(2,5-dioxo-2,5-dihydro-pyrrol-1-yl)-undecanoylamino]-3-nitro-benzyl ester (A) and (1R,3S,7S,10R,11S,12S,16S)-Carbonic acid 10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-[4-(2,5-dioxo-2,5-dihydro-pyrrol-1-yl)-undecanoylamino]-3-nitro-benzyl ester (B)

Analogously to Example EL2, 106 mg (108 μmol) of the compound prepared according to Example EL66 are reacted. After working-up and purification, 58 mg (58 μmol, 54%) of the title compound A as well as 6 mg (6 μmol, 6%) of the title compound B are isolated.

$^1$H-NMR (CDCl$_3$) of A: δ=0.96 (3H), 1.04 (3H), 1.23 (3H), 1.31 (3H), 0.81-1.83 (23H), 2.16 (2H), 2.23-2.66 (6H), 2.71 (1H), 2.85 (3H), 3.5 (2H), 3.72 (1H), 4.08 (1H), 4.24 (1H), 4.92 (1H), 4.97 (1H), 5.15 (2H), 5.22 (1H), 5.72 (1H), 6.25 (1H), 6.68 (2H), 7.36 (1H), 7.66 (1H), 7.83 (1H), 7.97 (1H), 8.25 (1H), 8.83 (1H), 10.37 (1H) ppm.

EXAMPLES OF THE SYNTHESIS OF EFFECTOR-LINKER RECOGNITION UNITS (ELE)

Example ELE1

[3-(3-(AP39r)-Sulfanyl-2,5-dioxo-pyrrolidin-1-yl)-propyl]-carbamic acid-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester

Example ELE1a

Reduction of an Antibody Fragment with Terminal Cysteine

A single-strand protein that consists of the variable domains of the heavy and light antibody chains (single-chain Fv, scFv) of the amino acid sequence EVQLLESGGGLVQPGGSLRLSCAASG-FTFSSFSMSWVRQAPGKGLEWVSSISGSS GTTYY-ADSVKGRFTISRDNSKNTLYLQMNSL-RAEDTAVYYCAKPFPYFDYWGQ GTLVTVSSGDGSSGGSGGASEIV-LTQSPGTLSLSPGERATLSCRASQSVSSSFLAW YQQK-PGQAPRLLIYYASSRATGIPDRFSGSGS-GTDFTLTISRLEPEDFAVYYCQQT GRIPPTFGQGTKVEIKGGGCA (SEQ ID NO: 1), which specifically recognizes the fibronectin domain B (ED-B) and is referred to as AP39, is used for coupling after reduction of the c-terminal cysteine.

For reduction, the solution of 661 μg of tri(2-carboxyethyl)phosphine-hydrochloride in 236 μl of PBS is mixed with the solution of 1.54 mg of AP39 in 1.12 ml of PBS, and it is incubated for 1.5 hours at 25° C. Desalination is done with a pre-equilibrated NAP-5 column at a concentration of 450 μl of AP39r and 50 μl of PBS. After elution with 1 ml of PBS, the reduced antibody fragment AP39r is isolated in a concentration of 0.7 mg/ml.

Example ELE1

(1S,3S,7S(3RS),10R,11S,12S,16R)-[3-(3-(AP39r)-Sulfanyl-2,5-dioxo-pyrrolidin-1-yl)-propyl]-carbamic acid-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 22.5 μl of a 1.38 mmol solution of effector-linker conjugate A in DMSO, prepared according to Example EL2, is added to 400 μl of the solution, prepared according to Example ELE1a, of the reduced antibody fragment, mixed with 77.5 μl of PBS and incubated at 25° C. for 1 hour. Desalination is done with a pre-equilibrated NAP5 column at a concentration of 500 μl of the reaction solution. After elution with PBS, the solution of the title compound is isolated The dilution factor relative to the antibody fragment is approximately 2.5.
m/z (Calc.): 26203.1 m/z (exp.): 26218±20

Example ELE2

(1S,3S,7S(3RS),10R,11S,12S,16R)-[5-(3-(AP39r)-Sulfanyl-2,5-dioxo-pyrrolidin-1-yl)-pentyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester Analogously to Example ELE1, the antibody fragment that is reduced according to Example ELE1a is reacted with effector-linker conjugate A that is prepared according to Example EL4, and the solution of the title compound is isolated. The dilution factor relative to the antibody fragment is approximately 2.5.
m/z (Calc.): 26231.2 m/z (exp.): 26236±20

Example ELE3

(1S,3S,7S(3RS),10R,11S,12S,16R)-[10-(3-(AP39r)-Sulfanyl-2,5-dioxo-pyrrolidin-1-yl)-decyl]-carbamic acid-10-allyl-11-hydroxy-8,8,12,16-tetramethyl-3-(2-methyl-benzothiazol-5-yl)-5,9-dioxo-4,17-dioxabicyclo[14.1.0]heptadec-7-yl ester Analogously to Example ELE1, the antibody fragment that is reduced according to Example ELE1a is reacted with effector-linker conjugate A that is prepared according to Example EL6, and the solution of the title compound is isolated. The dilution factor relative to the antibody fragment is approximately 2.5.
m/z (Calc.): 26301.4 m/z (exp.): 26303±20

Example ELE4

(1S,3S,7S,10R,11S(3RS),12S,16R)-[3-(3-(AP39r)-Sulfanyl-2,5-dioxo-pyrrolidin-1-yl)-propyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]heptadec-11-yl ester Analogously to Example ELE1, the antibody fragment that is reduced according to Example ELE1a is reacted with effector-linker conjugate A that is prepared according to Example EL8, and the solution of the title compound is isolated. The dilution factor relative to the antibody fragment is approximately 2.5.
m/z (Calc.): 26203.2 m/z (exp.): 26206±20

Example ELE5

(1S,3S,7S,10R,11S(3RS),12S,16R)-[5-(3-(AP39r)-Sulfanyl-2,5-dioxo-pyrrolidin-1-yl)-pentyl]-carbamic acid-10-allyl-7-hydroxy-8,8,12,16-tetramethyl-3-(2-methyl-benzothiazol-5-yl)-5,9-dioxo-4,17-dioxabicyclo[14.1.0]heptadec-11-yl ester Analogously to Example ELE1, the antibody fragment that is reduced according to Example ELE1a is reacted with effector-linker conjugate A that is prepared according to Example EL10, and the solution of the title compound is isolated. The dilution factor relative to the antibody fragment is approximately 2.5.
m/z (Calc.): 26231.2 m/z (exp.): 26225±20

Example ELE6

(1S,3S(E),7S,10R,11S,12S,16R)-[3-(3-(AP39r)-Sulfanyl-2,5-dioxo-pyrrolidin-1-yl)-propyl]-carbamic acid-7-[3-(2,5-dioxo-2,5-dihydro-pyrrol-1-yl)-propylcarbamoyloxy]-8,8,10,12,16-pentamethyl-3-[1-methyl-2-(2-methyl-thiazol-4-yl)-vinyl]-5,9-dioxo-4,17-dioxa-bicyclo[14.1.0]heptadec-11-yl ester (A) and (1S,3S(E),7S,10R,11S,12S,16R)-[3-(3-(AP39r)-Sulfanyl-2,5-dioxo-pyrrolidin-1-yl)-propyl]-carbamic acid-11-[3-(2,5-dioxo-2,5-dihydro-pyrrol-1-yl)-propylcarbamoyloxy]-8,8,10,12,16-pentamethyl-3-[1-methyl-2-(2-methyl-thiazol-4-yl)-vinyl]-5,9-dioxo-4,17-dioxa-bicyclo[14.1.0]heptadec-7-yl ester (B)

Analogously to Example ELE1, the antibody fragment that is reduced according to Example ELE1a is reacted with the effector-linker conjugate that is prepared according to Example EL11, and the solution of the title compounds is isolated. The dilution factor relative to the antibody fragment is approximately 2.5.
m/z (Calc.): 26347.3 m/z (exp.): 26358±20

Example ELE7

(1S,3S(E),7S,10R,11S,12S,16R)-N-[1-({4-[2-(7,11-Dihydroxy-8,8,10,12,16-pentamethyl-5,9-dioxo-4,17-dioxa-bicyclo[14.1.0]heptadec-3-yl)-propenyl]-thiazol-2-ylmethyl}-carbamoyl)-ethyl]-3-(AP39r)-disulfanyl-N-methyl-propionamide Analogously to Example ELE1, the antibody fragment that is reduced according to Example ELE1a is reacted with effector-linker conjugate A that is prepared according to Example EL16, and the solution of the title compound is isolated. The dilution factor relative to the antibody fragment is approximately 2.5.
m/z (Calc.): 26173 m/z (exp.): 26174±20

Example ELE8

(1S,3S(E),7S,10R,11S,12S,16R)-2-[Methyl-(3-(AP39r)-disulfanyl-propionyl)-amino]-propionic acid-4-[2-(7,11-dihydroxy-8,8,10,12,16-pentamethyl-5,9-dioxo-4,17-dioxa-bicyclo[14.1.0]heptadec-3-yl)-propenyl]-thiazol-2-ylmethyl ester Analogously to Example ELE1, the antibody fragment that is reduced according to Example ELE1a is reacted with effector-linker conjugate A that is prepared according to Example EL17, and the solution of the title compound is isolated. The dilution factor relative to the antibody fragment is approximately 2.5.

m/z (Calc.): 26174 m/z (exp.): 26163±20

Example ELE9

(1S,3S,7S,10R,11S,12S,16R)-Carbonic acid-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-(3-(AP39r)-sulfanyl-2,5-dioxo-pyrrolidin-1-yl)-phenyl ester Analogously to Example ELE1, the antibody fragment that is reduced according to Example ELE1a is reacted with effector-linker conjugate A that is prepared according to Example EL13, and the solution of the title compound is isolated. The dilution factor relative to the antibody fragment is approximately 2.5.

m/z (Calc.): 26238 m/z (exp.): 26224±20

Example ELE10

(1S,3S,7S,10R,11S,12S,16R)-Carbonic acid-10-allyl-7-hydroxy-8,8,12,16-tetramethyl-3-(2-methyl-benzothiazol-5-yl)-5,9-dioxo-4,17-dioxa-bicyclo[14.1.0]heptadec-11-yl ester 4-(3-(AP39r)-sulfanyl-2,5-dioxo-pyrrolidin-1-yl)-phenyl ester Analogously to Example ELE1, the antibody fragment that is reduced according to Example ELE1a is reacted with effector-linker conjugate A that is prepared according to Example EL15, and the solution of the title compound is isolated. The dilution factor relative to the antibody fragment is approximately 2.5.

m/z (Calc.): 26238 m/z (exp.): 26243±20

Example ELE11

4-(3-(AP39r)-Sulfanyl-2,5-dioxo-pyrrolidin-1-yl)-butanoic acid 4-(1S,3S,7S,10R,11S, 12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester Analogously to Example ELE1, the antibody fragment that is reduced according to Example ELE1a is reacted with effector-linker conjugate A that is prepared according to Example EL19, and the solution of the title compound is isolated. The dilution factor relative to the antibody fragment is approximately 2.5.

m/z (Calc.): 26383 m/z (exp.): 26377±20

Example ELE12

4-(3-(AP39r)-Sulfanyl-2,5-dioxo-pyrrolidin-1-yl)-butanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester Analogously to Example ELE1, the antibody fragment that is reduced according to Example ELE1a is reacted with effector-linker conjugate A that is prepared according to Example EL25, and the solution of the title compound is isolated. The dilution factor relative to the antibody fragment is approximately 2.5.

m/z (Calc.): 26383 m/z (exp.): 26381±20

Example ELE13

6-(3-(AP39r)-sulfanyl-2,5-dioxo-pyrrolidin-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester Analogously to Example ELE1, the antibody fragment that is reduced according to Example ELE1a is reacted with the effector-linker conjugate A that is prepared according to Example EL21, and the solution of the title compound is isolated. The dilution factor relative to the antibody fragment is approximately 2.5.

m/z (Calc.): 26411 m/z (exp.): 26384±30 m/z (Calc.): 25673 m/z (exp.): 25657±20 (6-(3-(AP39r)-sulfanyl-2,5-dioxo-pyrrolidin-1-yl)-hexanoic acid fragment)

Example ELE14

11-(3-(AP39r)-sulfanyl-2,5-dioxo-pyrrolidin-1-yl)-undecanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenyl ester Analogously to Example ELE1, the antibody fragment that is reduced according to Example ELE1a is reacted with the effector-linker conjugate A that is prepared according to Example EL23 and the solution of the title compound is isolated. The dilution factor relative to the antibody fragment is approximately 2.5.

m/z (Calc.): 26482 m/z (exp.): 26477±20 m/z (Calc.): 25744 m/z (exp.): 26752±20 (11-(3-(AP39r)-sulfanyl-2,5-dioxo-pyrrolidin-1-yl)-undecanoic acid fragment)

Example ELE15

6-(3-(AP39r)-sulfanyl-2,5-dioxo-pyrrolidin-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester Analogously to Example ELE1, the antibody fragment that is reduced according to Example ELE1a is reacted with the effector-linker conjugate A that is prepared according to Example EL27 and the solution of the title compound is isolated. The dilution factor relative to the antibody fragment is approximately 2.5.

m/z (Calc.): 26411 m/z (exp.): 26398±20 m/z (Calc.): 25673 m/z (exp.): 25665±20 (6-(3-(AP39r)-sulfanyl-2,5-dioxo-pyrrolidin-1-yl)-hexanoic acid fragment)

Example ELE16

11-(3-(AP39r)-sulfanyl-2,5-dioxo-pyrrolidin-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenyl ester Analogously to Example ELE1, the antibody fragment that is reduced according to Example ELE1a is reacted with the effector-linker conjugate A that is prepared according to Example EL29 and the solution of the title compound is isolated. The dilution factor relative to the antibody fragment is approximately 2.5.

m/z (Calc.): 26482 m/z (exp.): 26491±20 m/z (Calc.): 25744 m/z (exp.): 25757±20 (11-(3-(AP39r)-sulfanyl-2,5-dioxo-pyrrolidin-1-yl)-undecanoic acid fragment)

Example ELE17

4-(3-(AP39r)-sulfanyl-2,5-dioxo-pyrrolidin-1-yl)-butanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo [14.1.0]heptadec-7-yloxycarbonyloxymethyl]-phenyl ester Analogously to Example ELE1, the antibody fragment that is reduced according to Example ELE1a is reacted with the effector-linker conjugate A that is prepared according to Example EL31 and the solution of the title compound is isolated. The dilution factor relative to the antibody fragment is approximately 2.5.

m/z (Calc.): 26338 m/z (exp.): 26304±30

Example ELE18

6-(3-(AP39r)-sulfanyl-2,5-dioxo-pyrrolidin-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo [14.1.0]heptadec-7-yloxycarbonyloxymethyl]-phenyl ester Analogously to Example ELE1, the antibody fragment that is reduced according to Example ELE1a is reacted with the effector-linker conjugate A that is prepared according to Example EL33 and the solution of the title compound is isolated. The dilution factor relative to the antibody fragment is approximately 2.5.

m/z (Calc.): 26366 m/z (exp.): 26347±30

Example ELE19

11-(3-(AP39r)-sulfanyl-2,5-dioxo-pyrrolidin-1-yl)-undecanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-phenyl ester Analogously to Example ELE1, the antibody fragment that is reduced according to Example ELE1a is reacted with the effector-linker conjugate A that is prepared according to Example EL35 and the solution of the title compound is isolated. The dilution factor relative to the antibody fragment is approximately 2.5.

m/z (Calc.): 26437 m/z (exp.): 26412±30

Example ELE20

4-(3-(AP39r)-sulfanyl-2,5-dioxo-pyrrolidin-1-yl)-butanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo [14.1.0]heptadec-11-yloxycarbonyloxymethyl]-2-nitro-phenyl ester Analogously to Example ELE1, the antibody fragment that is reduced according to Example ELE1a is reacted with the effector-linker conjugate A that is prepared according to Example EL37 and the solution of the title compound is isolated. The dilution factor relative to the antibody fragment is approximately 2.5.

m/z (Calc.): 26338 m/z (exp.): 26338±20

Example ELE21

6-(3-(AP39r)-sulfanyl-2,5-dioxo-pyrrolidin-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo [14.1.0]heptadec-11-yloxycarbonyloxymethyl]-phenyl ester Analogously to Example ELE1, the antibody fragment that is reduced according to Example ELE1a is reacted with the effector-linker conjugate A that is prepared according to Example EL39 and the solution of the title compound is isolated. The dilution factor relative to the antibody fragment is approximately 2.5.

m/z (Calc.): 26366 m/z (exp.): 26384±30

Example ELE22

11-(3-(AP39r)-sulfanyl-2,5-dioxo-pyrrolidin-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-phenyl ester Analogously to Example ELE1, the antibody fragment that is reduced according to Example ELE1a is reacted with the effector-linker conjugate A that is prepared according to Example EL41 and the solution of the title compound is isolated. The dilution factor relative to the antibody fragment is approximately 2.5.

m/z (Calc.): 26437 m/z (exp.): 26421±30

Example ELE23

4-(3-(AP39r)-sulfanyl-2,5-dioxo-pyrrolidin-1-yl)-butanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo [14.1.0]heptadec-7-yloxycarbonyloxymethyl]-2-chloro-phenyl ester Analogously to Example ELE1, the antibody fragment that is reduced according to Example ELE1a is reacted with the effector-linker conjugate A that is prepared according to Example EL43 and the solution of the title compound is isolated. The dilution factor relative to the antibody fragment is approximately 2.5.

m/z (Calc.) 26373 m/z (exp.): 26358±20 m/z (Calc.) 25645 m/z (exp.): 25627±20 (4-(3-(AP39r)-sulfanyl-2,5-dioxo-pyrrolidin-1-yl)-butanoic acid fragment)

Example ELE24

6-(3-(AP39r)-sulfanyl-2,5-dioxo-pyrrolidin-1-yl)-hexanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo [14.1.0]heptadec-7-yloxycarbonyloxymethyl]-2-chloro-phenyl ester Analogously to Example ELE1, the antibody fragment that is reduced according to Example ELE1a is reacted with the effector-linker conjugate A that is prepared according to Example EL45 and the solution of the title compound is isolated. The dilution factor relative to the antibody fragment is approximately 2.5.

m/z (Calc.): 26401 m/z (exp.): 26395±20

Example ELE25

11-(3-(AP39r)-sulfanyl-2,5-dioxo-pyrrolidin-1-yl)-undecanoic acid 4-(1S,3S,7S,10R,11S,12S,16R)-[10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-chlor-phenyl ester Analogously to Example ELE1, the antibody fragment that is reduced according to Example ELE1a is reacted with the effector-linker conjugate A that is prepared according to Example EL47 and the solution of the title compound is isolated. The dilution factor relative to the antibody fragment is approximately 2.5.

m/z (Calc.): 26471 m/z (exp.): 26463±20

Example ELE26

4-(3-(AP39r)-sulfanyl-2,5-dioxo-pyrrolidin-1-yl)-butanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chloro-phenyl ester Analogously to Example ELE1, the antibody fragment that is reduced according to Example ELE1a is reacted with the effector-linker conjugate A that is prepared according to Example EL49 and the solution of the title compound is isolated. The dilution factor relative to the antibody fragment is approximately 2.5.

m/z (Calc.): 26373 m/z (exp.): 26341±30

Example ELE27

6-(3-(AP39r)-sulfanyl-2,5-dioxo-pyrrolidin-1-yl)-hexanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chlor-phenyl ester Analogously to Example ELE1, the antibody fragment that is reduced according to Example ELE1a is reacted with the effector-linker conjugate A that is prepared according to Example EL51 and the solution of the title compound is isolated. The dilution factor relative to the antibody fragment is approximately 2.5.

m/z (Calc.): 26401 m/z (exp.): 26391±20

Example ELE28

11-(3-(AP39r)-sulfanyl-2,5-dioxo-pyrrolidin-1-yl)-undecanoic acid 4-(1S,3S,7S,10R,11S,12S,16R)-[10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-chlor-phenyl ester Analogously to Example ELE1, the antibody fragment that is reduced according to Example ELE1a is reacted with the effector-linker conjugate A that is prepared according to Example EL53 and the solution of the title compound is isolated. The dilution factor relative to the antibody fragment is approximately 2.5.

m/z (Calc.): 26471 m/z (exp.): 26466±20

Example ELE29

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[4-(3-(AP39r)-sulfanyl-2,5-dioxo-pyrrolidin-1-yl)-butyrylamino]-3-nitro-benzyl ester Analogously to Example ELE1, the antibody fragment that is reduced according to Example ELE1a is reacted with the effector-linker conjugate A that is prepared according to Example EL55 and the solution of the title compound is isolated. The dilution factor relative to the antibody fragment is approximately 2.5.

m/z (Calc.): 26337 m/z (exp.):±20

Example ELE30

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[6-(3-(AP39r)-sulfanyl-2,5-dioxo-pyrrolidin-1-yl)-hexanoylamino]-3-nitro-benzyl ester Analogously to Example ELE1, the antibody fragment that is reduced according to Example ELE1a is reacted with the effector-linker conjugate A that is prepared according to Example EL57 and the solution of the title compound is isolated. The dilution factor relative to the antibody fragment is approximately 2.5.

m/z (Calc.): 26365 m/z (exp.):±20

Example ELE31

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 4-[11-(3-(AP39r)-sulfanyl-2,5-dioxo-pyrrolidin-1-yl)-undecanoylamino]-3-nitro-benzyl ester Analogously to Example ELE1, the antibody fragment that is reduced according to Example ELE1a is reacted with the effector-linker conjugate A that is prepared according to Example EL59 and the solution of the title compound is isolated. The dilution factor relative to the antibody fragment is approximately 2.5.

m/z (Calc.): 26436 m/z (exp.):±20

Example ELE32

(1S,3S,7S,10R,11S,12S,16R)-Carbonic acid 10-allyl-11-hydroxy-8,8,12,16-tetramethyl-3-(2-methyl-benzothiazol-5-yl)-5,9-dioxo-4,17-dioxa-bicyclo[14.1.0]heptadec-7-yl ester 6-(3-(AP39r)-sulfanyl-2,5-dioxo-pyrrolidin-1-yl)-hexyl ester Analogously to Example ELE1, the antibody fragment that is reduced according to Example ELE1a is reacted with the effector-linker conjugate A that is prepared according to Example EL61 and the solution of the title compound is isolated. The dilution factor relative to the antibody fragment is approximately 2.5.

m/z (Calc.): 26246 m/z (exp.):+20

Example ELE33

4-(3-(2H8-Ab)x-sulfanyl-2,5-dioxo-pyrrolidin-1-yl)-butanoic acid 4-(1S,3S,7S,10R,118S,12S,16R)-[10-allyl-7-hydroxy-8,8,12,16-tetramethyl-3-(2-methyl-benzothiazol-5-yl)-5,9-dioxo-4,17-dioxa-bicyclo [14.1.0]heptadec-11-yloxycarbonyloxymethyl]-2-nitro-phenyl ester 100 μl of a solution of the thionylated antibody prepared according to Example ELE33a (about 3 nmol, about 6 thiol groups) are mixed with 42.3 μl of a 1.1 mM solution of the effector-linker conjugate A prepared according to Example EL25 in PBS, and the mixture is incubated at 23° C. for 1 hour. Desalination is performed by using a pre-equilibrated NAP5 column with a loading of 150 μl of the reaction solution. After elution with PBS, the solution of the title compound is isolated. The loading factor x of antibody 2H8-A in relation to effector-linker is about 1:4 to 1:5.

Example ELE33a

Thionylation of a Complete Immunoglobuline (IgG), e.g., the 2H8 Antibody

For the introduction of thionyl groups an amine-free solution of the 2H8 antibody in phosphate buffer having a concentration in the range of about 1-10 mg/ml at a pH of 7.2 is mixed with the 10- to 100-fold excess of 2-iminothiolane and is allowed to react for 1 hour at 23° C. The number of the introduced thiol groups is 1 to about 15 depending on the excess of reagent.

The invention claimed is:
1. An effector conjugate of formula (I):

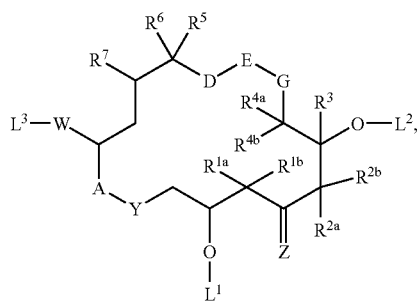

in which
R$^{1a}$, R$^{1b}$, independently of one another, are hydrogen, C$_1$-C$_{10}$ alkyl, aryl, aralkyl, or together a —(CH$_2$)$_m$ group, in which m is 2 to 5,
R$^{2a}$, R$^{2b}$, independently of one another, are hydrogen, C$_1$-C$_{10}$ alkyl, aryl, aralkyl, or together a —(CH$_2$)$_n$ group, in which n is 2 to 5, or C$_2$-C$_{10}$ alkenyl, or C$_2$-C$_{10}$ alkynyl,
R$^3$ is hydrogen, C$_1$-C$_{10}$ alkyl, aryl or aralkyl, and
R$^{4a}$, R$^{4b}$, independently of one another, are hydrogen, C$_1$-C$_{10}$ alkyl, aryl, aralkyl, or together a —(CH$_2$)$_p$ group, in which p is 2 to 5,
R$^5$ is hydrogen, C$_1$-C$_{10}$ alkyl, aryl, aralkyl, CO$_2$H, CO$_2$alkyl, CH$_2$OH, CH$_2$Oalkyl, CH$_2$Oacyl, CN, CH$_2$NH$_2$, CH$_2$N(alkyl, acyl)$_{1,2}$, or CH$_2$Hal,
Hal is a halogen atom,
R$^6$, R$^7$ in each case are hydrogen, or together an additional bond, or together an oxygen atom, or together an NH group, or together an N-alkyl group, or together a CH$_2$ group, and
G is an oxygen atom or CH$_2$,
D-E is a group H$_2$C—CH$_2$, HC═CH, C≡C, CH(OH)—CH(OH), CH(OH)—CH$_2$, CH$_2$—CH(OH),

O—CH$_2$, or, if G represents a CH$_2$ group, D-E is CH$_2$—O,
W is a group C(═X)R$^8$, or a bicyclic or tricyclic aromatic or heteroaromatic radical,
L$^3$ is hydrogen, or, if a radical in W contains a hydroxyl group, forms a group O-L$^4$ with the latter, or, if a radical in W contains an amino group, forms a group NR$^{25}$-L$^4$ with the latter,
R$^{25}$ is hydrogen or C$_1$-C$_{10}$ alkyl, X is an oxygen atom, or two OR$^{20}$ groups, or a C$_2$-C$_{10}$ alkylenedioxy group that may be straight or branched, or H and OR$^9$, or a CR$^{10}$R$^{11}$ group,
R$^8$ is hydrogen, C$_1$-C$_{10}$ alkyl, aryl, aralkyl, halogen or CN, and
R$^9$ is hydrogen or a protective group PG$^X$,
R$^{10}$, R$^{11}$, in each case independently of one another, are hydrogen, C$_1$-C$_{20}$ alkyl, aryl, aralkyl, or together with a methylene carbon atom form a 5- to 7-membered carbocyclic ring,
Z can represent oxygen or H and OR$^{12}$,
R$^{12}$ can represent hydrogen or a protective group PG$^Z$,
A-Y can represent a group O—C(═O), O—CH$_2$, CH$_2$—C(═O), NR$^{21}$—C(═O) or NR$^{21}$—SO$_2$,
R$^{20}$ represent C$_1$-C$_{20}$ alkyl,
R$^{21}$ represent a hydrogen atom or C$_1$-C$_{10}$ alkyl,
PG$^X$, PG$^Y$, and PG$^Z$ represent a protective group PG, and
L$^1$, L$^2$, and L$^4$, independently of one another, represent hydrogen, a group C(═O)Cl, a group C(═S)Cl, a group PG$^Y$ or a linker of general formula (III) or (IV); provided that at least one substituent L$^1$, L$^2$ or L$^4$ represents a linker of general formula (III) or (IV);
the linker of general formula (III) has the following structure,

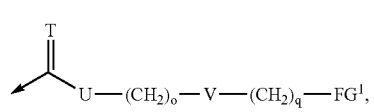

in which
T represent oxygen or sulfur,
U represent oxygen, CHR$^{22}$, CHR$^{22}$—NR$^{23}$—C(═O)—, O—C(═O)—CHR$^{22}$—NR$^{23}$—C(═O)—, O—C(═O)—CHR$^{22}$—NR$^{23}$—C(═S)—, CHR$^{22}$—NR$^{23}$—C(═S)— or NR$^{24a}$,
o can represent 0 to 15,
V can represent a bond, aryl, a group

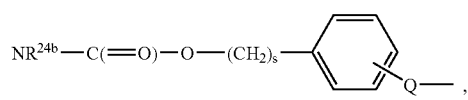

or a group

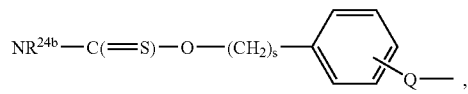

s represent 0 to 4,

Q represent a bond, O—C(=O)—NR$^{24c}$, O—C(=S)—NR$^{24c}$,

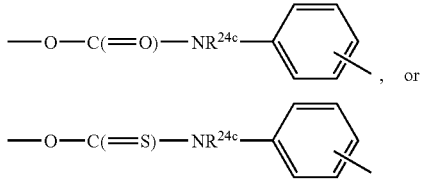

R$^{22}$ represent hydrogen, C$_1$-C$_{10}$ alkyl, aryl or aralkyl,

R$^{23}$ represent hydrogen or C$_1$-C$_{10}$ alkyl,

R$^{24a}$, R$^{24b}$, and R$^{24c}$, independently of one another, represent hydrogen or C$_1$-C$_{10}$ alkyl, q represent 0 to 15, FG$^1$ represent C$_1$-C$_{10}$ alkyl-S$_3$,

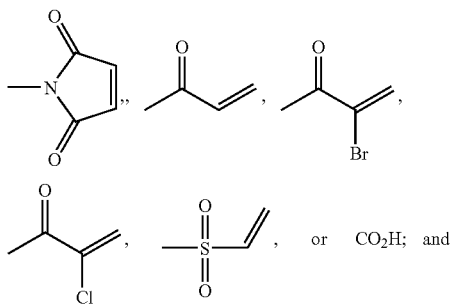

the linker of general formula (IV) has the following structure,

IV

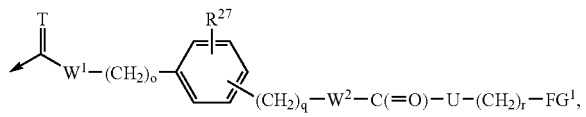

in which

T represent oxygen or sulfur,

W$^1$, W$^2$ are the same or different and represent oxygen or NR$^{24a}$, o represent 0 to 5, R$^{24a}$ represent hydrogen or C$_1$-C$_{10}$ alkyl, R$^{27}$ represent halogen, CN, NO$_2$, CO$_2$R$^{28}$, or OR$^{28}$, R$^{28}$ represent hydrogen, C$_1$-C$_{10}$ alkyl, aryl or aralkyl, q represent 0 to 5, U represent oxygen, CHR$^{22}$, CHR$^{22}$—NR$^{23}$—C(=O)—, CHR$^{22}$—NR$^{23}$—C(=S)— or C$_1$-C$_{20}$ alkyl, R$^{22}$ represent hydrogen, C$_1$-C$_{10}$ alkyl, aryl or aralkyl, R$^{23}$ represent hydrogen or C$_1$-C$_{10}$ alkyl, r can represent 0 to 20, FG$^1$ represent C$_1$-C$_{10}$ alkyl-S$_3$,

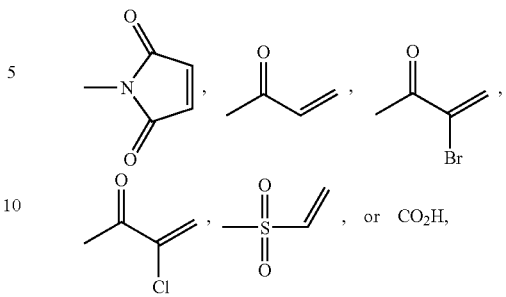

as a single isomer or a mixture of different isomers and/or as a pharmaceutically acceptable salt thereof.

2. An effector conjugate according to claim 1, wherein:
A-Y represents O—C(=O) or NR$^{21}$—C(=O),
D-E represents an H$_2$C—CH$_2$ group,
G represents a CH$_2$ group,
Z represents an oxygen atom,
R$^{1a}$, R$^{1b}$ in each case represent C$_1$-C$_{10}$ alkyl or together a —(CH$_2$)$_p$ group with p equal to 2 or 3 or 4,
R$^{2a}$, R$^{2b}$, independently of one another, represent hydrogen, C$_1$-C$_{10}$ alkyl, C$_2$-C$_{10}$ alkenyl, or C$_2$-C$_{10}$ alkynyl,
R$^3$ represents hydrogen,
R$^{4a}$, R$^{4b}$, independently of one another, represent hydrogen or C$_1$-C$_{10}$ alkyl;
R$^5$ represents hydrogen, or C$_1$-C$_4$ alkyl or CH$_2$OH or CH$_2$NH$_2$ or CH$_2$N(alkyl, acyl)$_{1,2}$ or CH$_2$Hal,
R$^6$ and R$^7$ together represent an additional bond or together an NH group, or together an N-alkyl group, or together a CH$_2$ group, or together an oxygen atom,
W represents a group C(=X)R$^8$ or a 2-methylbenzothiazol-5-yl radical or a 2-methylbenzoxazol-5-yl radical or a quinolin-7-yl radical or a 2-aminomethylbenzothiazol-5-yl radical or a 2-hydroxymethylbenzothiazol-5-yl radical or a 2-aminomethyl-benzoxazol-5-yl radical or a 2-hydroxymethylbenzoxazol-5-yl radical,
X represents a CR$^{10}$R$^{11}$ group,
R$^8$ represents hydrogen or C$_1$-C$_4$ alkyl or a fluorine atom or a chlorine atom or a bromine atom,
R$^{10}$/R$^{11}$ represent hydrogen/2-methylthiazol-4-yl or hydrogen/2-pyridyl or hydrogen/2-methyloxazol-4-yl or hydrogen/2-aminomethylthiazol-4-yl or hydrogen/2-aminomethyloxazol-4-yl or hydrogen/2-hydroxymethylthiazol-4-yl or hydrogen/2-hydroxymethyloxazol-4-yl.

3. An effector conjugate according to claim 1, wherein the effector element is
(4S,7R,8S,9S,13Z,16S(E))-4,8-Dihydroxy-5,5,7,9,13-pentamethyl-16-[1-methyl-2-(2-methyl-thiazol-4-yl)-vinyl]-oxacyclohexadec-13-ene-2,6-dione;
(4S,7R,8S,9S,13Z,16S(E))-4,8-Dihydroxy-16-[2-(2-hydroxymethyl-thiazol-4-yl)-1-methyl-vinyl]-5,5,7,9,13-pentamethyl-oxacyclohexadec-13-ene-2,6-dione;
(4S,7R,8S,9S,13Z,16S(E))-16-[2-(2-Aminomethyl-thiazol-4-yl)-1-methyl-vinyl]-4,8-dihydroxy-5,5,7,9,13-pentamethyl-oxacyclohexadec-13-ene-2,6-dione;
(1S,3S(E),7S,10R,11S,12S,16R)-7,11-Dihydroxy-8,8,10,12,16-pentamethyl-3-[1-methyl-2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-8,8,10,12,16-pentamethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-1-methyl-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(E),-4,8-Dihydroxy-7-ethyl-5,5,9,13-tetramethyl-16-[1-methyl-2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-1-methyl-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-1-methyl-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-10-ethyl-8,8,12,16-tetramethyl-4,17-dioxa-bicyclo[14.1.0]hepta-decane-5,9-dione;

(1S,3S(E),7S,10R,11S,12S,16R)-3-[2-(2-Aminomethyl-thiazol-4-yl)-1-methyl-vinyl]-7,11-dihydroxy-10-ethyl-8,8,12,16-tetramethyl-4,17-dioxa-bicyclo[14.1.0]hepta-decane-5,9-dione;

(4S,7R,8S,9S,13Z,16S(Z))-4,8-Dihydroxy-5,5,7,9,13-pentamethyl-16-[1-fluoro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-fluoro-vinyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-8,8,10,12,16-pentamethyl-4,17-dioxa-bicyclo[14.1.0]heptadecane-5,9-dione;

(1S,3S(Z),7S,10R,11S,12S,16R)-3-[2-(2-Aminomethyl-thiazol-4-yl)-1-fluoro-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-chloro-vinyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-8,8,10,12,16-pentamethyl-4,17-dioxa-bicyclo[14.1.0]heptadecane-5,9-dione;

(1S,3S(Z),7S,10R,11S,12S,16R)-3-[2-(2-Aminomethyl-thiazol-4-yl)-1-chloro-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(Z))-4,8-Dihydroxy-7-ethyl-5,5,9,13-tetramethyl-16-[1-fluoro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-fluoro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-10-ethyl-8,8,12,16-tetramethyl-4,17-dioxa-bicyclo[14.1.0]hepta-decane-5,9-dione;

(1S,3S(Z),7S,10R,11S,12S,16R)-3-[2-(2-Aminomethyl-thiazol-4-yl)-1-fluoro-vinyl]-7,11-dihydroxy-10-ethyl-8,8,12,16-tetramethyl-4,17-dioxa-bicyclo[14.1.0]hepta-decane-5,9-dione;

(4S,7R,8S,9S,13Z,16S(Z))-4,8-Dihydroxy-7-ethyl-5,5,9,13-tetramethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-chloro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-10-ethyl-8,8,12,16-tetramethyl-4,17-dioxa-bicyclo[14.1.0]hepta-decane-5,9-dione;

(1S,3S(Z),7S,10R,11S,12S,16R)-3-[2-(2-Aminomethyl-thiazol-4-yl)-1-chloro-vinyl]-7,11-dihydroxy-10-ethyl-8,8,12,16-tetramethyl-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-fluoro-2-(2-pyridyl)-vinyl]-oxacyclohexadec-13-ene-2,6-dione;

(1S,3S(Z),7S,10R,11S,12S,16R)-7,11-Dihydroxy-8,8,10,
12,16-pentamethyl-3-[1-fluoro-2-(2-pyridyl)-vinyl]-4,
17-dioxa-bicyclo[14.1.0]heptadecane-5,9-dione;

(4S,7R,8S,9S,13Z,16S(Z))-4,8-Dihydroxy-5,5,7,9,13-
pentamethyl-16-[1-chloro-2-(2-pyridyl)-vinyl]-oxacy-
clohexadec-13-ene-2,6-dione;

(1S,3S(Z),7S,10R,11S,12S,16R)-7,11-Dihydroxy-8,8,10,
12,16-pentamethyl-3-[1-chloro-2-(2-pyridyl)-vinyl]-4,
17-dioxa-bicyclo[14.1.0]heptadecane-5,9-dione;

(4S,7R,8S,9S,13Z,16S(Z))-4,8-Dihydroxy-7-ethyl-5,5,9,
13-tetramethyl-16-[1-fluoro-2-(2-pyridyl)-vinyl]-ox-
acyclohexadec-13-ene-2,6-dione;

(1S,3S(Z),7S,10R,11S,12S,16R)-7,11-Dihydroxy-10-
ethyl-8,8,12,16-tetramethyl-3-[1-fluoro-2-(2-pyridyl)-
vinyl]-4,17-dioxa-bicyclo[14.1.0]heptadecane-5,9-di-
one;

(4S,7R,8S,9S,13Z,16S(Z))-4,8-Dihydroxy-7-ethyl-5,5,9,
13-tetramethyl-16-[1-chloro-2-(2-pyridyl)-vinyl]-ox-
acyclohexadec-13-ene-2,6-dione;

(1S,3S(Z),7S,10R,11S,12S,16R)-7,11-Dihydroxy-10-
ethyl-8,8,12,16-tetramethyl-3-[1-chloro-2-(2-pyridyl)-
vinyl]-4,17-dioxa-bicyclo[14.1.0]heptadecane-5,9-di-
one;

(4S,7R,8S,9S,13Z,16S(E))-4,8-Dihydroxy-5,5,7,9,13-
pentamethyl-16-[1-methyl-2-(2-methyl-oxazol-4-yl)-
vinyl]-oxacyclohexadec-13-ene-2,6-dione;

(4S,7R,8S,9S,13Z,16S(E))-4,8-Dihydroxy-16-[2-(2-hy-
droxymethyl-oxazol-4-yl)-1-methyl-vinyl]-5,5,7,9,13-
pentamethyl-oxacyclohexadec-13-ene-2,6-dione;

(4S,7R,8S,9S,13Z,16S(E))-16-[2-(2-Aminomethyl-ox-
azol-4-yl)-1-methyl-vinyl]-4,8-dihydroxy-5,5,7,9,13-
pentamethyl-oxacyclohexadec-13-ene-2,6-dione;

(1S,3S(E),7S,10R,11S,12S,16R)-7,11-Dihydroxy-8,8,10,
12,16-pentamethyl-3-[1-methyl-2-(2-methyl-oxazol-4-
yl)-vinyl]-4,17-dioxa-bicyclo[14.1.0]heptadecane-5,9-
dione;

(1S,3S(E),7S,10R,11S,12S,16R)-7,11-Dihydroxy-3-[2-
(2-hydroxymethyl-oxazol-4-yl)-1-methyl-vinyl]-8,8,
10,12,16-pentamethyl-4,17-dioxa-bicyclo[14.1.0]hep-
tadecane-5,9-dione;

(1S,3S(E),7S,10R,11S,12S,16R)-3-[2-(2-Aminomethyl-
oxazol-4-yl)-1-methyl-vinyl]-7,11-dihydroxy-8,8,10,
12,16-pentamethyl-4,17-dioxa-bicyclo[14.1.0]hepta-
decane-5,9-dione;

(4S,7R,8S,9S,13Z,16S(E))-4,8-Dihydroxy-7-ethyl-5,5,9,
13-tetramethyl-16-[1-methyl-2-(2-methyl-oxazol-4-
yl)-vinyl]-oxacyclohexadec-13-ene-2,6-dione;

(4S,7R,8S,9S,13Z,16S(E))-4,8-Dihydroxy-16-[2-(2-hy-
droxymethyl-oxazol-4-yl)-1-methyl-vinyl]-7-ethyl-5,
5,9,13-tetramethyl-oxacyclohexadec-13-ene-2,6-di-
one;

(4S,7R,8S,9S,13Z,16S(E))-16-[2-(2-Aminomethyl-ox-
azol-4-yl)-1-methyl-vinyl]-4,8-dihydroxy-7-ethyl-5,5,
9,13-tetramethyl-oxacyclohexadec-13-ene-2,6-dione;

(1S,3S(E),7S,10R,11S,12S,16R)-7,11-Dihydroxy-10-
ethyl-8,8,12,16-tetramethyl-3-[1-methyl-2-(2-methyl-
oxazol-4-yl)-vinyl]-4,17-dioxa-bicyclo[14.1.0]hepta-
decane-5,9-dione;

(1S,3S(E),7S,10R,11S,12S,16R)-7,11-Dihydroxy-3-[2-
(2-hydroxymethyl-oxazol-4-yl)-1-methyl-vinyl]-10-
ethyl-8,8,12,16-tetramethyl-4,17-dioxa-bicyclo
[14.1.0]hepta-decane-5,9-dione;

(1S,3S(E),7S,10R,11S,12S,16R)-3-[2-(2-Aminomethyl-
oxazol-4-yl)-1-methyl-vinyl]-7,11-dihydroxy-10-
ethyl-8,8,12,16-tetramethyl-4,17-dioxa-bicyclo
[14.1.0]hepta-decane-5,9-dione;

(4S,7R,8S,9S,13Z,16S(Z))-4,8-Dihydroxy-5,5,7,9,13-
pentamethyl-16-[1-fluoro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-fluoro-vinyl]-5,5,7,9,13-
pentamethyl-oxacyclohexadec-13-ene-2,6-dione;

(4S,7R,8S,9S,13Z,16S(Z))-16-[2-(2-Aminomethyl-ox-
azol-4-yl)-1-fluoro-vinyl]-4,8-dihydroxy-5,5,7,9,13-
pentamethyl-oxacyclohexadec-13-ene-2,6-dione;

(1S,3S(Z),7S,10R,11S,12S,16R)-7,11-Dihydroxy-8,8,10,
12,16-pentamethyl-3-[1-fluoro-2-(2-methyl-oxazol-4-
yl)-vinyl]-4,17-dioxa-bicyclo[14.1.0]heptadecane-5,9-
dione;

(1S,3S(Z),7S,10R,11S,12S,16R)-7,11-Dihydroxy-3-[2-
(2-hydroxymethyl-oxazol-4-yl)-1-fluoro-vinyl]-8,8,10,
12,16-pentamethyl-4,17-dioxa-bicyclo[14.1.0]hepta-
decane-5,9-dione;

(1S,3S(Z),7S,10R,11S,12S,16R)-3-[2-(2-Aminomethyl-
oxazol-4-yl)-1-fluoro-vinyl]-7,11-dihydroxy-8,8,10,
12,16-pentamethyl-4,17-dioxa-bicyclo[14.1.0]hepta-
decane-5,9-dione;

(4S,7R,8S,9S,13Z,16S(Z))-4,8-Dihydroxy-5,5,7,9,13-
pentamethyl-16-[1-chloro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-chloro-vinyl]-5,5,7,9,13-
pentamethyl-oxacyclohexadec-13-ene-2,6-dione;

(4S,7R,8S,9S,13Z,16S(Z))-16-[2-(2-Aminomethyl-ox-
azol-4-yl)-1-chloro-vinyl]-4,8-dihydroxy-5,5,7,9,13-
pentamethyl-oxacyclohexadec-13-ene-2,6-dione;

(1S,3S(Z),7S,10R,11S,12S,16R)-7,11-Dihydroxy-8,8,10,
12,16-pentamethyl-3-[1-chloro-2-(2-methyl-oxazol-4-
yl)-vinyl]-4,17-dioxa-bicyclo[14.1.0]heptadecane-5,9-
dione;

(1S,3S(Z),7S,10R,11S,12S,16R)-7,11-Dihydroxy-3-[2-
(2-hydroxymethyl-oxazol-4-yl)-1-chloro-vinyl]-8,8,
10,12,16-pentamethyl-4,17-dioxa-bicyclo[14.1.0]hep-
tadecane-5,9-dione;

(1S,3S(Z),7S,10R,11S,12S,16R)-3-[2-(2-Aminomethyl-
oxazol-4-yl-1-chloro-vinyl]-7,11-dihydroxy-8,8,10,12,
16-pentamethyl-4,17-dioxa-bicyclo[14.1.0]heptade-
cane-5,9-dione;

(4S,7R,8S,9S,13Z,16S(Z))-4,8-Dihydroxy-7-ethyl-5,5,9,
13-tetramethyl-16-[1-fluoro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-fluoro-vinyl]-7-ethyl-5,5,
9,13-tetramethyl-oxacyclohexadec-13-ene-2,6-dione;

(4S,7R,8S,9S,13Z,16S(Z))-16-[2-(2-Aminomethyl-ox-
azol-4-yl)-1-fluoro-vinyl]-4,8-dihydroxy-7-ethyl-5,5,
9,13-tetramethyl-oxacyclohexadec-13-ene-2,6-dione;

(1S,3S(Z),7S,10R,11S,12S,16R)-7,11-Dihydroxy-10-
ethyl-8,8,12,16-tetramethyl-3-[1-fluoro-2-(2-methyl-
oxazol-4-yl)-vinyl]-4,17-dioxa-bicyclo[14.1.0]hepta-
decane-5,9-dione;

(1S,3S(Z),7S,10R,11S,12S,16R)-7,11-Dihydroxy-3-[2-
(2-hydroxymethyl-oxazol-4-yl)-1-fluoro-vinyl]-10-
ethyl-8,8,12,16-tetramethyl-4,17-dioxa-bicyclo
[14.1.0]hepta-decane-5,9-dione;

(1S,3S(Z),7S,10R,18S,12S,16R)-3-[2-(2-Aminomethyl-
oxazol-4-yl)-1-fluoro-vinyl]-7,11-dihydroxy-10-ethyl-
8,8,12,16-tetramethyl-4,17-dioxa-bicyclo[14.1.0]
hepta-decane-5,9-dione;

(4S,7R,8S,9S,13Z,16S(Z))-4,8-Dihydroxy-7-ethyl-5,5,9,
13-tetramethyl-16-[1-chloro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hydroxymethyl-oxazol-4-yl)-1-chloro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-oxazol-4-yl)-1-chloro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-methyl-oxazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-oxazol-4-yl)-1-chloro-vinyl]-10-ethyl-8,8,12,16-tetramethyl-4,17-dioxa-bicyclo[14.1.0]hepta-decane-5,9-dione;

(1S,3S(Z),7S,10R,11S,12S,16R)-3-[2-(2-Aminomethyl-oxazol-4-yl)-1-chloro-vinyl]-7,11-dihydroxy-10-ethyl-8,8,12,16-tetramethyl-4,17-dioxa-bicyclo[14.1.0]hepta-decane-5,9-dione;

(4S,7R,8S,9S,13Z,16S(E))-4,8-Dihydroxy-5,5,7,9,13-pentamethyl-16-[2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-vinyl]-5,5,7,9,13-pentamethyl-oxacyclohexadec-13-ene-2,6-dione;

(4S,7R,8S,9S,13Z,16S(E))-16-[2-(2-Aminomethyl-thiazol-4-yl)-vinyl]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,12,16-pentamethyl-3-[2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-vinyl]-8,8,10,12,16-pentamethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-vinyl]-10-ethyl-8,8,12,16-tetramethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-vinyl]-7,11-dihydroxy-10-ethyl-8,8,12,16-tetramethyl-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-pyridyl)-vinyl]-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-5,5,7,9,13-pentamethyl-oxacyclohexadec-13-ene-2,6-dione;

(4S,7R,8S,9S,13Z,16S)-16-(2-Aminomethyl-benzothiazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-8,8,10,12,16-pentamethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-ethyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-propyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-propyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-butyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-butyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-butyl-8,8,12,16-tetramethyl-4,17-dioxa-bicyclo[14.1.0]heptadecane-5,9-dione;

(4S,7R,8S,9S,13Z,16S)-4,8-Dihydroxy-7-allyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-allyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-allyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-prop-2-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-prop-2-inyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-enyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-enyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzothiazol-5-yl)oxacyclohexadec-13-ene-2,6-dione;

(4S,7R,8S,9S,13Z,16S)-4,8-Dihydroxy-16-(2-hydroxymethyl-benzothiazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-but-3-inyl-8,8,12,16-tetramethyl-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-5,5,7,9,13-pentamethyl-oxacyclohexadec-13-ene-2,6-dione;

(4S,7R,8S,9S,13Z,16S)-16-(2-Aminomethyl-benzoxazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-8,8,10,12,16-pentamethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-ethyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-propyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-propyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-butyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-butyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-butyl-8,8,12,16-tetramethyl-4,17-dioxa-bicyclo[14.1.0]heptadecane-5,9-dione;

(4S,7R,8S,9S,13Z,16S)-4,8-Dihydroxy-7-allyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-allyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-allyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-prop-2-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-prop-2-inyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-enyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-enyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-inyl-8,8,12,16-tetramethyl-4,17-dioxa-bicyclo[14.1.0]heptadecane-5,9-dione; or (1S,3S,7S,10R,11S,12S,16R)-3-(2-Aminomethyl-benzoxazol-5-yl)-7,11-dihydroxy-10-but-3-inyl-8,8,12,16-tetramethyl-4,17-dioxa-bicyclo[14.1.0]heptadecane-5,9-dione, wherein the hydrogen atoms in the above-mentioned effector elements are replaced in the positions indicated in formula (I) by radicals $L^1$-$L^3$.

4. An effector conjugate according to claim 1, wherein the linker is a compound of formula (III), wherein V represents a bond or an aryl radical, o is zero, and T is an oxygen atom.

5. An effector conjugate according to claim 1, wherein the linker is a compound of formula (III), wherein V represents a bond or an aryl radical or a group

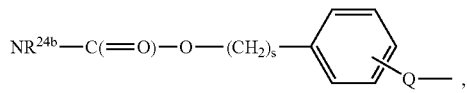

o is 0 to 4, and

Q is a bond or a group

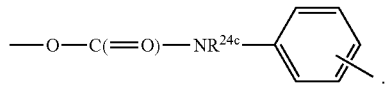

6. An effector conjugate according to claim 5, wherein V is a bond or a group

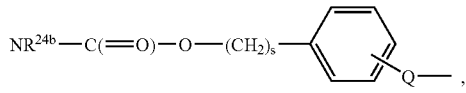

Q is a bond or a group

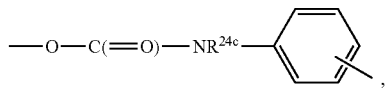

o is 0, 2 or 3, s is 1, and

T is an oxygen atom.

7. An effector conjugate according to claim 1, wherein the linker is a compound of formula (IV), wherein o is 0 to 4, and q is 0 to 3.

* * * * *

UNITED STATES PATENT AND TRADEMARK OFFICE
CERTIFICATE OF CORRECTION

PATENT NO. : 7,335,775 B2 Page 1 of 1
APPLICATION NO. : 11/509557
DATED : February 26, 2008
INVENTOR(S) : Markus Berger It is certified that error appears in the above-identified patent and that said Letters Patent is hereby corrected as shown below:

Column 92, line 4, claim 3 reads "-7,1-" should read -- -7,11- --

Signed and Sealed this

Eighth Day of July, 2008

JON W. DUDAS
*Director of the United States Patent and Trademark Office*